US012667345B2

(12) United States Patent
Nock et al.

(10) Patent No.: US 12,667,345 B2
(45) Date of Patent: *Jun. 30, 2026

(54) CORE NEEDLE BIOPSY DEVICE FOR COLLECTING MULTIPLE SAMPLES IN A SINGLE INSERTION

(71) Applicant: Devicor Medical Products, Inc., Cincinnati, OH (US)

(72) Inventors: Andrew Paul Nock, Dayton, OH (US); David C. McBreen, West Chester, OH (US); Justin Rebellino, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 1001 days.

This patent is subject to a terminal disclaimer.

(21) Appl. No.: 17/729,453

(22) Filed: Apr. 26, 2022

(65) Prior Publication Data

US 2022/0249075 A1     Aug. 11, 2022

Related U.S. Application Data

(63) Continuation-in-part of application No. 16/381,573, filed on Apr. 11, 2019, now Pat. No. 11,602,335, (Continued)

(51) Int. Cl.
*A61B 10/02* (2006.01)

(52) U.S. Cl.
CPC .. *A61B 10/0275* (2013.01); *A61B 2010/0208* (2013.01)

(58) Field of Classification Search
CPC .................... A61B 10/0275; A61B 2010/0208
See application file for complete search history.

(56) References Cited

U.S. PATENT DOCUMENTS

| | | | |
|---|---|---|---|
| 5,511,556 A | 4/1996 | DeSantis |
| 5,526,822 A | 6/1996 | Burbank et al. |

(Continued)

FOREIGN PATENT DOCUMENTS

| | | |
|---|---|---|
| EP | 3103397 | 12/2016 |
| EP | 3669789 | 6/2020 |

(Continued)

OTHER PUBLICATIONS

Chinese Office Action dated Nov. 3, 2021 for Application No. 201780070564.4, 17 pages.

(Continued)

*Primary Examiner* — Charles A Marmor, II
*Assistant Examiner* — Severo Antonio P Lopez
(74) *Attorney, Agent, or Firm* — FBT Gibbons LLP

(57) ABSTRACT

A core needle biopsy device includes a needle assembly, a cutter drive assembly, a piercer drive assembly and an actuation mechanism. The needle assembly includes a piercer and a hollow cutter. The piercer includes a sharp distal tip and a notch proximal to the distal tip. The piercer is slidably disposed within the cutter to sever a tissue sample into the notch. The cutter drive assembly is configured to move the cutter. The piercer drive assembly is configured to move the piercer. The piercer drive assembly includes a lead screw configured to move both a portion of the cutter drive assembly and a portion of the piercer drive assembly. The actuation mechanism is configured to engage bot the cutter drive assembly and the piercer drive assembly to initiate firing of the piercer and the cutter sequentially using the cut drive assembly and the piercer drive assembly.

18 Claims, 42 Drawing Sheets

Related U.S. Application Data which is a continuation of application No. PCT/US2017/056123, filed on Oct. 11, 2017.

(60) Provisional application No. 62/407,201, filed on Oct. 12, 2016.

(56) References Cited

U.S. PATENT DOCUMENTS

| | | | |
|---|---|---|---|
| 5,560,373 | A | 10/1996 | DeSantis |
| 5,817,033 | A | 10/1998 | DeSantis et al. |
| 5,971,939 | A | 10/1999 | DeSantis et al. |
| 6,017,316 | A | 1/2000 | Ritchart et al. |
| 6,086,544 | A | 7/2000 | Hibner et al. |
| 6,162,187 | A | 12/2000 | Buzzard et al. |
| 6,432,065 | B1 | 8/2002 | Burdorff et al. |
| 6,626,849 | B2 | 9/2003 | Huitema et al. |
| 6,752,768 | B2 | 6/2004 | Burdorff et al. |
| 6,860,860 | B2 | 3/2005 | Viola |
| 7,226,459 | B2 | 6/2007 | Cesarini et al. |
| 7,442,171 | B2 | 10/2008 | Stephens et al. |
| 7,648,466 | B2 | 1/2010 | Stephens et al. |
| 7,837,632 | B2 | 11/2010 | Stephens et al. |
| 7,854,706 | B2 | 12/2010 | Hibner |
| 7,914,464 | B2 | 3/2011 | Burdorff et al. |
| 7,938,786 | B2 | 5/2011 | Ritchie et al. |
| 8,083,687 | B2 | 12/2011 | Parihar |
| 8,118,755 | B2 | 2/2012 | Hibner et al. |
| 8,206,316 | B2 | 6/2012 | Hibner et al. |
| 8,241,226 | B2 | 8/2012 | Hibner et al. |
| 8,282,574 | B2 | 10/2012 | Coonahan et al. |
| 8,337,415 | B2 * | 12/2012 | Trezza, II ...... A61B 17/320016 606/80 |
| 8,454,531 | B2 | 6/2013 | Speeg et al. |
| 8,485,989 | B2 | 7/2013 | Videbaek |
| 8,486,989 | B2 | 7/2013 | Videbaek |
| 8,622,924 | B2 | 1/2014 | Speeg et al. |
| 8,702,623 | B2 | 4/2014 | Parihar et al. |
| 8,764,680 | B2 | 7/2014 | Rhad et al. |
| 8,801,742 | B2 | 8/2014 | Rhad et al. |
| 8,858,465 | B2 | 10/2014 | Fiebig |
| 8,938,285 | B2 | 1/2015 | Fiebig et al. |
| 9,095,326 | B2 | 8/2015 | Ritchie et al. |
| 9,326,755 | B2 | 5/2016 | Fiebig et al. |
| 9,345,457 | B2 | 5/2016 | Speeg et al. |
| 10,368,849 | B2 | 8/2019 | Coonahan et al. |
| 11,013,499 | B2 | 5/2021 | Shabaz |
| 11,602,335 | B2 * | 3/2023 | Nock ................. A61B 10/0275 |
| 2002/0065474 | A1 | 5/2002 | Viola |
| 2006/0074345 | A1 | 4/2006 | Hibner |
| 2009/0131821 | A1 | 5/2009 | Speeg et al. |
| 2010/0152610 | A1 | 6/2010 | Parihar et al. |
| 2010/0160819 | A1 | 6/2010 | Parihar et al. |
| 2011/0054350 | A1 * | 3/2011 | Videbaek ........... A61B 10/0275 600/568 |
| 2013/0324882 | A1 | 12/2013 | Mescher |
| 2014/0371585 | A1 | 12/2014 | Thompson et al. |
| 2016/0089121 | A1 * | 3/2016 | Stand, III ............... F16H 25/20 74/89.23 |
| 2019/0231325 | A1 | 8/2019 | Nock |
| 2019/0321009 | A1 | 10/2019 | Nevo et al. |
| 2020/0187919 | A1 | 6/2020 | Long et al. |
| 2021/0153850 | A1 | 5/2021 | Kjeldsen et al. |

FOREIGN PATENT DOCUMENTS

| | | |
|---|---|---|
| JP | H11-506634 | 6/1995 |
| JP | 2004-535837 | 12/2004 |
| JP | 2005-103276 | 4/2005 |
| JP | 2009-505696 | 2/2009 |
| JP | 2009-532081 | 9/2009 |
| WO | WO 2007/112751 A2 | 10/2007 |

OTHER PUBLICATIONS

Chinese Office Action dated May 23, 2022 for Application No. 201780070564.4, 14 pages.

European Communication dated Nov. 26, 2020 for Application No. 17791244.1, 8 pages.

European Communication dated Apr. 9, 2021 for Application No. 17791244.1, 6 pages.

Japanese Office Action dated Jun. 29, 2021 for Application No. 2019-519761, 8 pages.

Japanese Office Action dated Dec. 21, 2021 for Application No. 2019-519761, 6 pages.

International Search Report and Written Opinion dated Mar. 14, 2018 for International Application No. PCT/US2017/056123, 14 pages.

Hahn, M., et al., "Diagnostic Primer: Vacuum-Assisted Breast Biopsy with Mammotome®," Devicor Medical Germany GmBh, Nov. 11, 2012, Germany, Springer Medizin Verlag, copyright 2013, 130 pgs.

Chinese Office Action dated Nov. 3, 2022 for Application No. 201780070564.4, 5 pages.

European Communication dated Sep. 29, 2022 for Application No. 17791244.1, 4 pages.

Korean Office Action dated Oct. 28, 2022 for Application No. 10-2019-7013614, 4 pages.

International Search Report and Written Opinion dated Nov. 18, 2022 for Application No. PCT/US2022/026314, 17 pages.

* cited by examiner

CORE NEEDLE BIOPSY DEVICE FOR COLLECTING MULTIPLE SAMPLES IN A SINGLE INSERTION

PRIORITY

The present application is a continuation-in-part of U.S. patent application Ser. No. 16/381,573, entitled "CORE NEEDLE BIOPSY DEVICE FOR COLLECTING MULTIPLE SAMPLES IN A SINGLE INSERTION," filed Apr. 11, 2019 and published as U.S. Patent Pub. No. 2019/0231325 on Aug. 1, 2019, which is a continuation of International App. No. PCT/US2017/056123, entitled "CORE NEEDLE BIOPSY DEVICE FOR COLLECTING MULTIPLE SAMPLES IN A SINGLE INSERTION," filed Oct. 11, 2017, which claims priority to U.S. Provisional Patent App. No. 62/407,201, entitled "CORE NEEDLE BIOPSY DEVICE FOR COLLECTING MULTIPLE SAMPLES IN A SINGLE INSERTION," filed on Oct. 12, 2016, the disclosure of which is hereby incorporated by reference.

BACKGROUND

A biopsy is the removal of a tissue sample from a patient to enable examination of the tissue for signs of cancer or other disorders. Tissue samples may be obtained in a variety of ways using various medical procedures involving a variety of the sample collection devices. For example, biopsies may be open procedures (surgically removing tissue after creating an incision) or percutaneous procedures (e.g. by fine needle aspiration, core needle biopsy, or vacuum assisted biopsy). After the tissue sample is collected, the tissue sample is typically analyzed at a lab (e.g. a pathology lab, biomedical lab, etc.) that is set up to perform the appropriate tests (such as histological analysis).

Biopsy samples have been obtained in a variety of ways in various medical procedures including open and percutaneous methods using a variety of devices. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

One technique for collecting a breast biopsy is to use a core needle biopsy device. One such device is the MAX-CORE disposable core biopsy instrument manufactured by Bard Biopsy Systems. Core needle biopsy devices frequently use a sharp, solid piercer equipped with a lateral tissue receiving notch positioned adjacent to the distal end of the piercer. When tissue is received within the notch, an elongate hollow cutting sheath is translated over the notch to sever a tissue sample. The severed tissue sample is then stored within the notch until both the piercer and the cutting sheath are removed from the patient. Thus, in core-needle biopsy devices, only one tissue sample can be collected per insertion of the piercer and cutting sheath.

Another technique for conducting a breast biopsy is to conduct a breast biopsy using a vacuum-assisted breast biopsy device. In contrast to core needle breast biopsy procedures, vacuum-assisted breast biopsy devices permit the probe to remove multiple samples without requiring the probe be removed from the breast after every sample is collected. For instance, in a vacuum assisted breast biopsy device, a hollow needle is used to penetrate tissue. The hollow needle includes a lateral aperture adjacent to a sharp distal tip. A hollow cutter is disposed within the hollow needle and is moved axially relative to the lateral aperture of the needle to sever tissue samples. Once a tissue sample is severed by the hollow cutter, the tissue sample is transported axially though the cutter and collected in a tissue collection feature.

Examples of vacuum assisted biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; U.S. Pat. No. 8,118,755, entitled "Biopsy Sample Storage," issued Feb. 1, 2012; U.S. Pat. No. 8,206,316, entitled "Tetherless Biopsy Device with Reusable Portion," issued on Jun. 26, 2012; U.S. Pat. No. 8,702,623, entitled "Biopsy Device with Discrete Tissue Chambers," issued on Apr. 22, 2014; U.S. Pat. No. 8,858,465, entitled "Biopsy Device with Motorized Needle Firing," issued Oct. 14, 2014; and U.S. Pat. No. 9,326,755, entitled "Biopsy Device Tissue Sample Holder with Bulk Chamber and Pathology Chamber," issued May 3, 2016. The disclosure of each of the above-cited U.S. patents is incorporated by reference herein.

Additional examples of vacuum assisted biopsy devices and biopsy system components are disclosed in U.S. Pub. No. 2006/0074345, entitled "Biopsy Apparatus and Method," published Apr. 6, 2006 and now abandoned; U.S. Pub. No. 2009/0131821, entitled "Graphical User Interface for Biopsy System Control Module," published May 21, 2009, now abandoned; U.S. Pub. No. 2010/0152610, entitled "Hand Actuated Tetherless Biopsy Device with Pistol Grip," published Jun. 17, 2010, now abandoned; U.S. Pub. No. 2010/0160819, entitled "Biopsy Device with Central Thumbwheel," published Jun. 24, 2010, now abandoned; and U.S. Pub. No. 2013/0324882, entitled "Control for Biopsy Device," published Dec. 5, 2013. The disclosure of each of the above-cited U.S. patent application Publications is incorporated by reference herein.

Exemplary core needle biopsy devices are disclosed in U.S. Pat. No. 5,560,373, entitled "Needle Core Biopsy Instrument with Durable or Disposable Cannula Assembly," issued on Oct. 1, 1996; U.S. Pat. No. 5,817,033, entitled "Needle Core Biopsy Device," issued on Oct. 6, 1998; U.S. Pat. No. 5,971,939, entitled "Needle Core Biopsy Device," issued on Oct. 26, 1999; and U.S. Pat. No. 5,511,556, entitled "Needle Core Biopsy Instrument," issued on Apr. 30, 1996. The disclosure of each of the above-cited U.S. patents is incorporated by reference herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1:
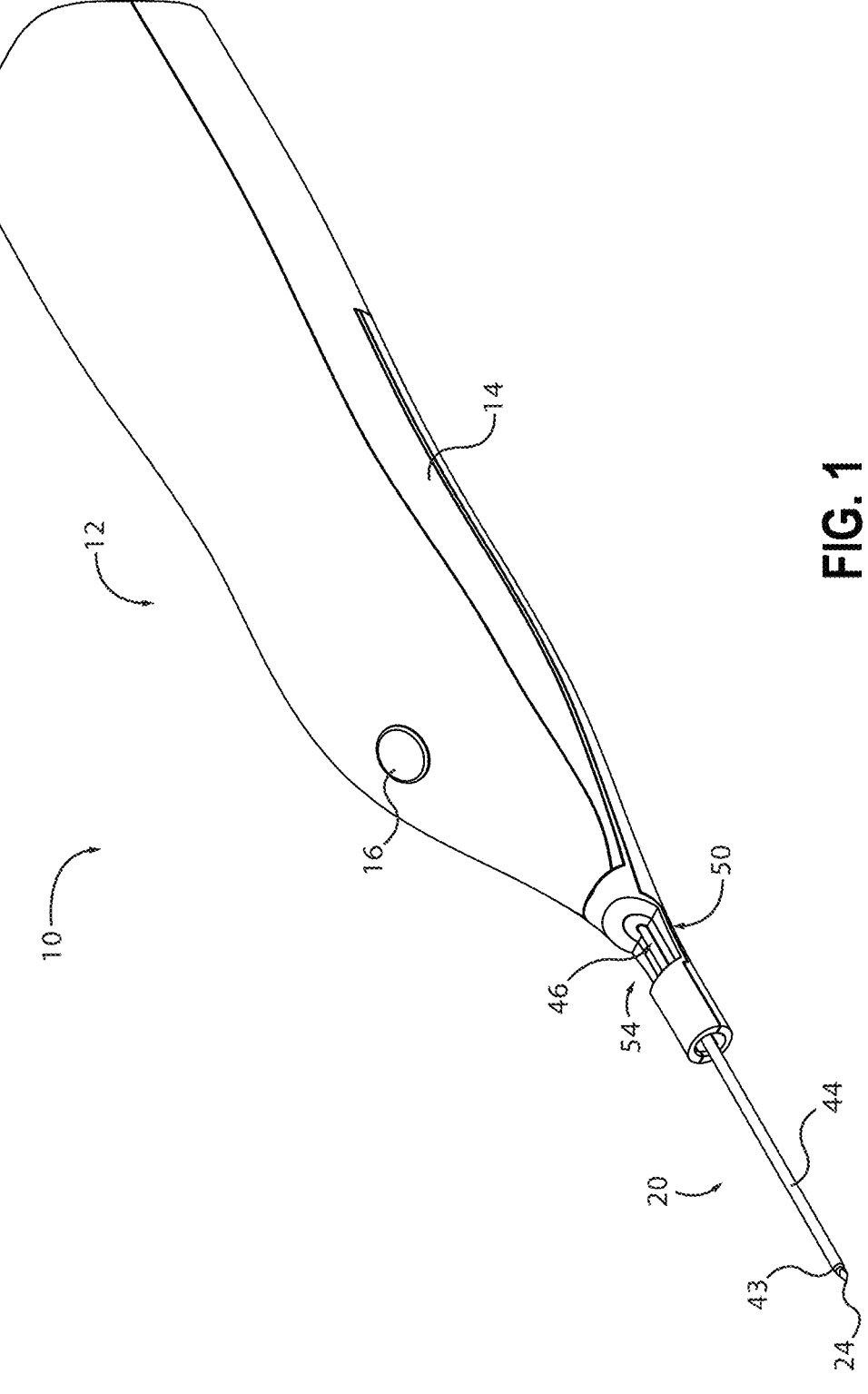
FIG. 1 depicts a perspective view of an exemplary core needle biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Biopsy devices may be used to collect tissue samples in a variety of ways. For example, in some instances tissue samples are collected into a single tissue basket such that all tissue samples collected during a given biopsy procedure are deposited into the single tissue sample basket. In some other instances, tissue samples are collected into a tissue sample holder having separate compartments for each collected tissue sample. Such a multi-compartment tissue sample holder may additionally include trays or strips that individually hold each tissue sample separately from the other tissue samples. Such trays or strips may be removable or otherwise separable from the tissue sample holder at the conclusion of a biopsy procedure.

Regardless of the structure in which the tissue samples are stored, tissue samples may be collected using biopsy devices under the guidance of various imaging modalities such as ultrasound image guidance, stereotactic (X-ray) guidance, MRI guidance, Positron Emission Mammography ("PEM" guidance), Breast-Specific Gamma Imaging ("BSGI") guidance, or otherwise. Each procedure has its own methodology based on the form of imaging guidance used. The following text briefly describes ultrasound image guided biopsy procedures, stereotactic guided biopsy procedures and MRI guided biopsy procedures.

In an ultrasound image guided breast biopsy procedure, the operator may position an ultrasound transducer on the patient's breast and maneuver the transducer while viewing an ultrasound image display screen to locate suspicious tissue in the patient's breast. Once the operator locates the suspicious tissue, the operator may anesthetize the target region of the breast. Once the breast has been anesthetized, the operator may create an initial incision using a scalpel at a location on the exterior of the breast offset from the transducer. A needle of a breast biopsy probe disposed coaxially within an introducer cannula is then inserted into the breast through the initial incision. The operator continues to hold the ultrasound transducer with one hand while maneuvering the biopsy probe with the other hand. While viewing the ultrasound image on the display screen, the operator guides the needle to a position adjacent to the suspicious tissue. A cutter within the needle of the probe is used to remove tissue which is then conveyed either to a manual pick-up location on the breast biopsy device or to a tissue sample chamber. The needle of the breast biopsy device is then removed, leaving the introducer cannula disposed within the breast. The introducer cannula may then be used to introduce a biopsy marker cannula for deploying a biopsy site marker at the biopsy site. Once a marker has been deployed at the biopsy site, the biopsy marker cannula and the introducer cannula are both removed from the breast and the incision is closed using a medically acceptable way to close breaks in the skin.

In a stereotactic image guided breast biopsy procedure, the patient is first positioned relative to x-ray equipment, which includes a breast localization assembly. In some procedures, the patient is oriented in a prone position, with the patient lying face down on a procedure table with at least one breast hanging pendulously through an aperture in the procedure table. The breast is then compressed between a compression paddle and an x-ray receptor of a localization assembly that is positioned under the procedure table. A breast biopsy device is positioned on an automatic guide device in front of the compression paddle and between the breast and an x-ray source. Once positioning of the patient and localization of the breast are complete, a scout image is acquired with the x-ray receptor in a zero-degree angular position (i.e., the x-rays are emitted along an axis normal relative to the x-ray receptor). If the scout image indicates that the patient has been positioned in a desired position, the procedure may proceed with the acquisition of stereotactic image pairs. Stereotactic image pairs are acquired by orienting the x-ray source at various complementary angular positions relative to the x-ray receptor (e.g., +15° and −15°), with at least one x-ray image acquired at each position.

Further in the stereotactic image guided breast biopsy procedure, once a suitable stereotactic image pair is acquired, an operator may identify a target site where biopsy sampling is desired by examining the stereotactic image pair. The target site is marked on each stereotactic image and a precise location of the target site on a Cartesian coordinate system is computed using an image processing module. The computed location of the target site is then communicated to the automatic guide device. The automatic guide device is responsive to this information to position the breast biopsy probe into a position that aligns with the target site. With the breast biopsy device positioned, an operator may then fire a needle of the biopsy probe into the breast of the patient, thereby positioning the needle at the target site. A cutter within the needle of the probe is used to remove tissue, which is then conveyed either to a manual pick-up location on the breast biopsy device or to a tissue sample chamber. After the biopsy tissue is removed, a biopsy marker cannula is inserted into the needle and is used to deploy a biopsy site marker at the biopsy site. Once a marker has been deployed at the biopsy site, the needle is removed from the breast and the incision is closed using a medically acceptable way to close breaks in the skin.

In an MRI guided breast biopsy procedure, after the patient is properly positioned on the table and a targeting device (e.g., a grid and cube combination or a pillar, post and cradle support combination) has been deployed and used, a baseline MRI image is taken to verify the target location. After that, a scalpel is used to incise the skin of the breast. Next, an assembly, formed by an obturator disposed in a sleeve, is inserted through the incision to penetrate the breast tissue under the skin. In some acceptable surgical techniques, the obturator is removed and an imaging rod is inserted into the sleeve in place of the obturator. An imaging rod is defined simply as an appropriately shaped rod that includes a feature that is detectable by an imaging technique being used for the biopsy procedure. The MRI image of the imaging rod is used to locate the site to which the sleeve/ obturator assembly has penetrated. In some other acceptable surgical techniques, the obturator cooperates with the breast tissue to provide a visually observable artifact in an MRI image. With both of these techniques, after the location within the breast where the biopsy is to be taken is confirmed, the obturator or the imaging rod is removed.

Further in the MRI guided breast biopsy procedure, after the obturator or imaging rod has been removed, it is replaced in the sleeve with the needle of a breast biopsy probe. A cutter within the needle of the probe is used to remove tissue, which is then conveyed either to a manual pick up location on the breast biopsy device or to a breast biopsy device sample chamber. After the biopsy tissue is removed, a biopsy marker cannula is inserted into the needle and is used to deploy a biopsy site marker at the biopsy site. The needle is then removed from the sleeve. Optionally, the imaging rod or the obturator is put back into the breast for reimaging of the biopsy site. Then the imaging rod or obturator and the sleeve are removed.

Vacuum assisted biopsy devices and core needle biopsy devices both may have various advantages over the other, depending on context. For instance, one advantage of vacuum assisted biopsy devices is that vacuum assistance permits removal of multiple tissue samples using a single insertion. However, while core needle biopsy devices lack this feature, use of core needle biopsy devices may still be desirable. For instance, core needle biopsy devices are generally capable of having smaller needles relative to core needle biopsy devices, thereby reducing patient anxiety and increasing the capacity of the needle to penetrate a lesion. Therefore, in some instances it may be desirable to incorporate the feature of multiple sample removal of a vacuum assisted biopsy device into a core needle biopsy device to achieve the benefits present in both styles of biopsy device.

A desirable feature of the device described herein, which is a core needle biopsy device is that the device allows for single insertion with multiple samples being obtained while using a core needle type device. Currently, it is believed that only vacuum assisted biopsy devices have this ability.

I. EXAMPLE OF CORE NEEDLE BIOPSY DEVICE

FIG. 1 shows an exemplary core needle biopsy device (10) for use in a breast biopsy procedure. Core needle biopsy device (10) of the present example comprises a body (12) and a needle assembly (20) extending distally from body (12). Body (12) includes an outer housing (14) and an actuation member (16) disposed on outer housing (14). As will be describe in greater detail below, outer housing (14) encloses various components of biopsy device (10), which are used to drive needle assembly (20) through a cutting cycle and a tissue acquisition cycle. To this end, outer housing (14) of the present example is sized and shaped for grasping by an operator using a single hand. Although not shown, it should be understood that in some examples outer housing (14) may comprise multiple parts such that each part interconnects to form outer housing (14).

Figure 2:
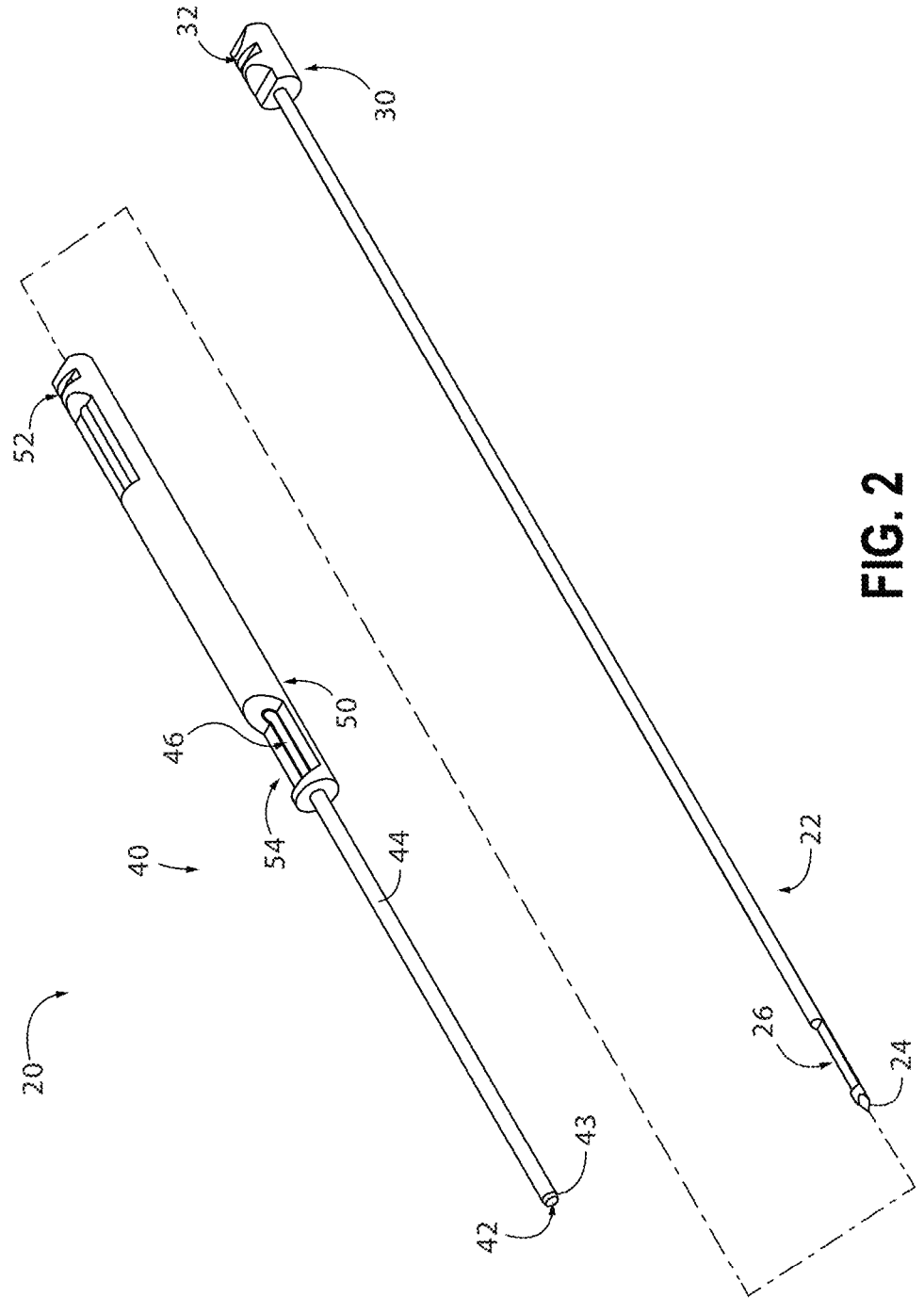
FIG. 2 depicts an exploded view of a needle assembly of the core needle biopsy device of FIG. 1.
Figure 3:
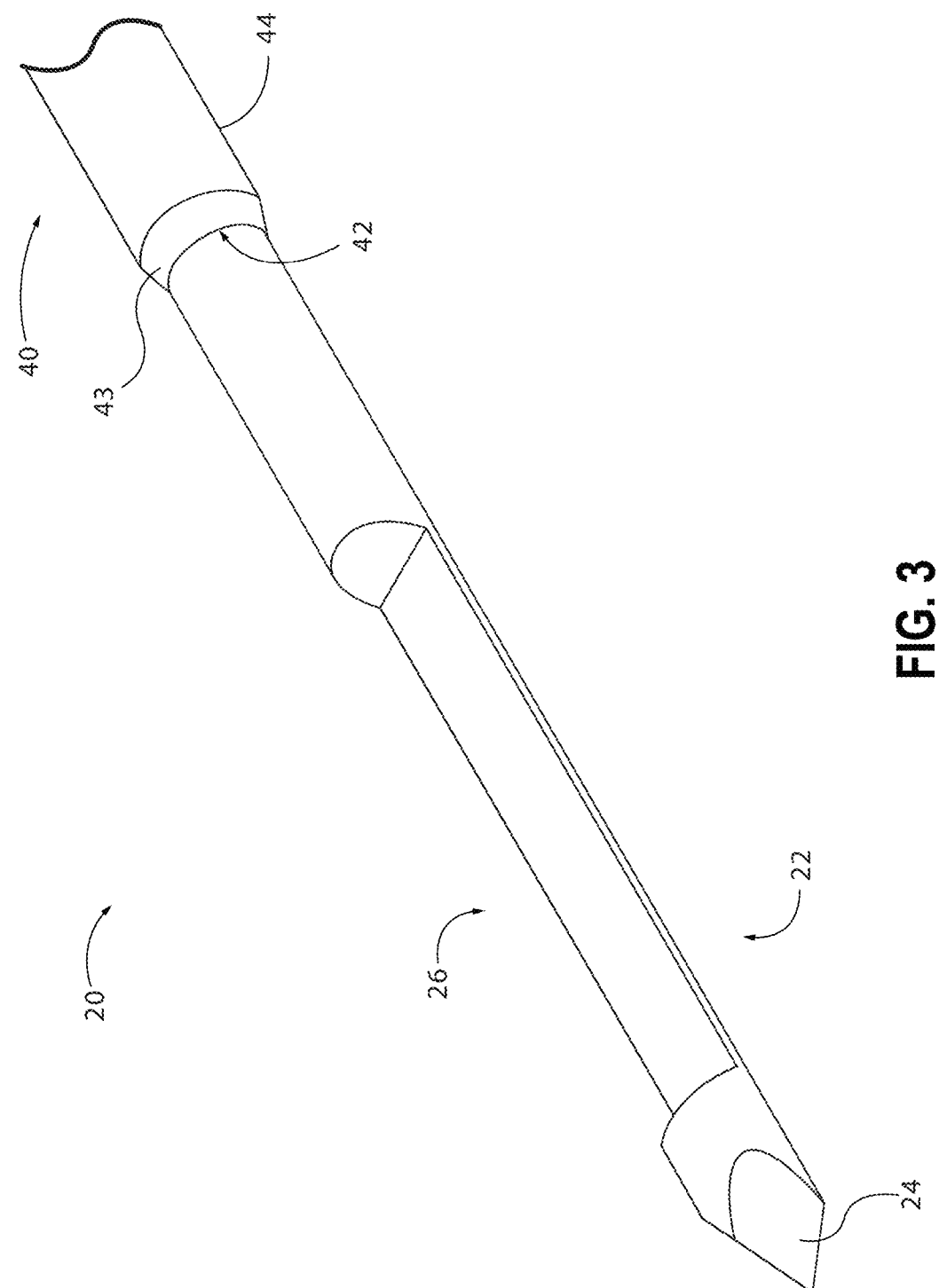
FIG. 3 depicts a perspective view of the needle assembly of FIG. 2.

FIGS. 2 and 3 show needle assembly (20) in greater detail. As can be seen in FIG. 2, needle assembly (20) comprises an elongate piercer (22) and an elongate cutter (40). As will be described in greater detail below, piercer (22) is generally movable relative to cutter (40) to pierce tissue and collect tissue samples, while cutter is generally movable relative to piercer (22) to sever tissue samples. Piercer (22) comprises a generally cylindrical rod having a sharp distal tip (24) and a notch (26) disposed adjacent to distal tip (24). As will be described in greater detail below, distal tip (24) is generally configured to penetrate tissue of a patient. As will also be described in greater detail below, notch (26) is generally configured to receive tissue therein such that a tissue sample may be collected within notch (26) after the tissue sample is severed by cutter (40).

An end portion (30) is disposed on the proximal end of piercer (22). End portion (30) of the present example is overmolded onto the proximal end of piercer (22) and is generally configured to enhance the manipulability of piercer (22). In particular, end portion (30) comprises a receiving feature (32) in the form of a lateral notch. Receiving feature (32) is configured to receive a portion of a piercer drive assembly (300). As will be described in greater detail below, this permits piercer drive assembly (300) to drive movement of piercer (22) through a predetermined sequence of movement.

Cutter (40) comprises a generally hollow cylindrical tube that is configured to receive piercer (22) therein. Cutter (40) comprises an open distal end (42), a cannula portion (44) and an end portion (50). Open distal end (42) is configured to permit at least a portion of piercer (22) to protrude from cutter (40) when piercer (22) is moved relative to cutter (40). As will be described in greater detail below, this configuration permits needle assembly (20) to move through the cutting cycle and the tissue acquisition cycle by permitting notch (26) of piercer (22) to move relative to distal end (42) of cutter (40).

Open distal end (42) of the present example includes a tapered edge (43). Tapered edge (43) is generally configured to slice through tissue to separate tissue samples when cutter (40) is moved relative to notch (26) of piercer (22). Thus, it should be understood that tapered edge (43) is generally configured to act a blade. Although the present example is described and shown as using a tapered configuration, it should be understood that in other examples various alternative configurations can be used. For instance, in some examples tapered edge (43) includes a plurality of serrations in addition or in alternative to the taper shown. In still other examples, tapered edge (43) can include any other additional or alternative cutting surface as will be apparent to those of ordinary skill in the art in view of the teachings herein.

Cannula portion (44) of cutter (40) extends proximally from distal end (42) through end portion (50) such that piercer (22) can be received with the proximal end of cutter (40). Unlike end portion (30) of piercer (22), end portion (50) of cutter (40) is generally elongate such that at least a portion of end portion (50) extends distally relative to outer housing (14). As will be described in greater detail below, this distal extension relative to outer housing (14) permits a portion of end portion (50) to be accessible to an operator for tissue sample collection purposes.

End portion (50) of cutter (40) comprises a receiving feature (52) and a tissue collection feature (54). As with receiving feature (32) of piercer (22), receiving feature (52) of end portion (50) comprises a lateral slot or other receiving feature that is configured to receive at least a portion of a cutter drive assembly (200). As will be described in greater detail below, receiving feature (52) is configured to receive at least a portion of cutter drive assembly (200) to permit cutter drive assembly (200) to move cutter (40) through a predetermined sequence of movement.

Tissue collection feature (54) is disposed distally relative to receiving feature (52). Tissue collection feature (54) generally defines an elongate notch that is open to cannula portion (44) of cutter (40). Correspondingly, cannula portion (44) includes a cutout portion (46) that is adjacent to tissue collection feature (54). Accordingly, it should be understood that tissue collection feature (54) is in communication with the hollow interior, or a lumen, defined by cannula portion (44). As will be described in greater detail below, this relationship between tissue collection feature (54) and cannula portion (44) permits an operator to remove tissue samples from cutter (40) as they are collected by piercer (22).

FIG. 3 shows piercer (22) disposed within cutter (40). As can be seen, cutter (40) is generally configured to receive piercer (22) such that piercer (22) is coaxial with cutter (40). In addition, piercer (22) is generally movable relative to open distal end (42) of cutter (40). It should be understood that in some circumstances piercer (22) moves relative to cutter (40), while cutter (40) remains stationary. In other circumstances, cutter (40) moves relative to piercer (22), while piercer (22) remains stationary. In either case, it should be understood that piercer (22) and cutter (40) are generally configured such that notch (26) of piercer (22) moves into and out of cutter (40) such that notch (26) can be disposed distally or proximally relative to open distal end (42) of cutter (40). As will be described in greater detail below, this configuration permits piercer (22) and cutter (40) to operate cooperatively to pierce tissue, cut a tissue sample, and retract the tissue sample for collection by an operator via tissue collection feature (54).

Figure 4:
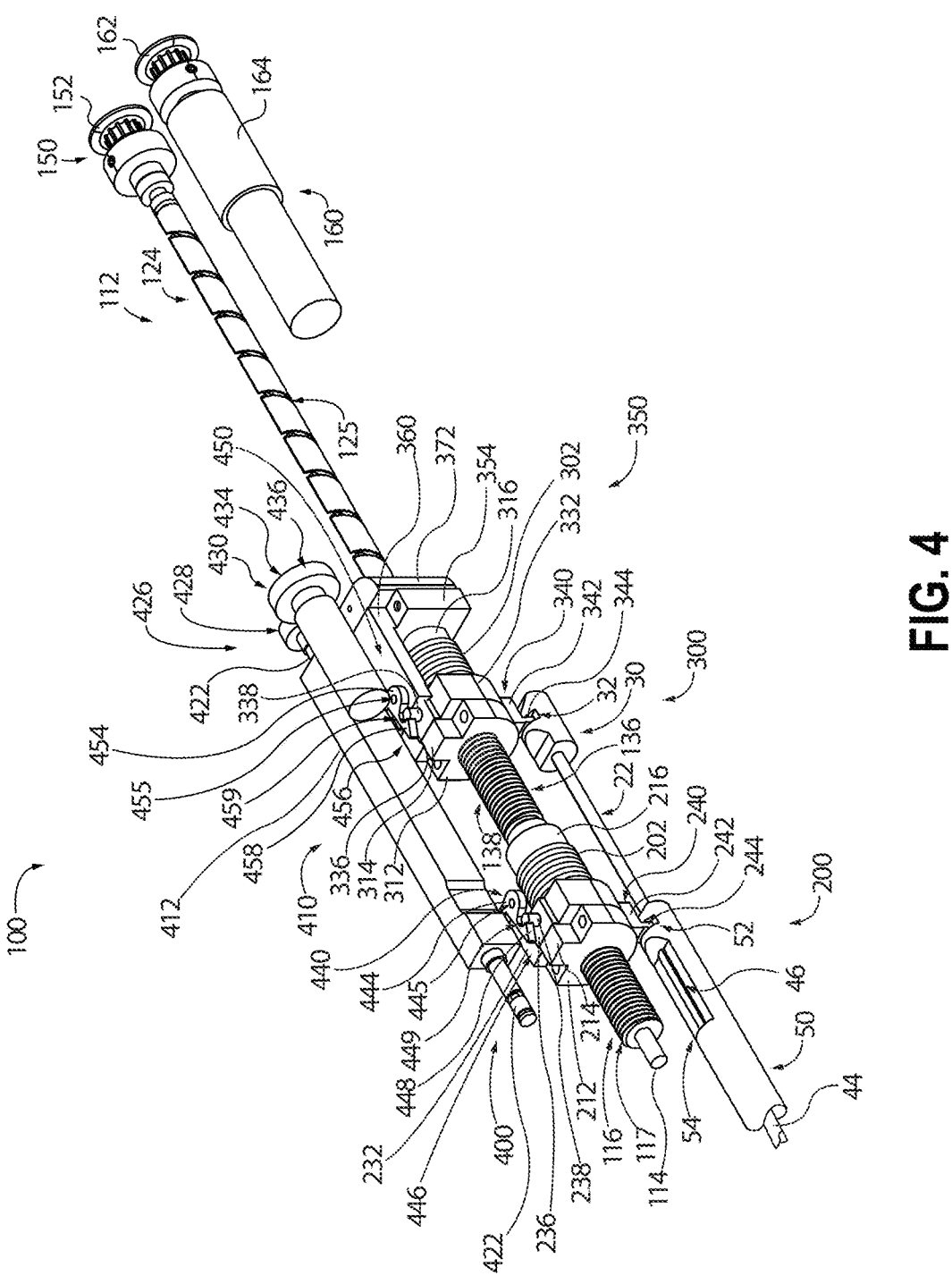
FIG. 4 depicts a perspective view of a drive assembly of the core needle biopsy device of FIG. 1.
Figure 5:
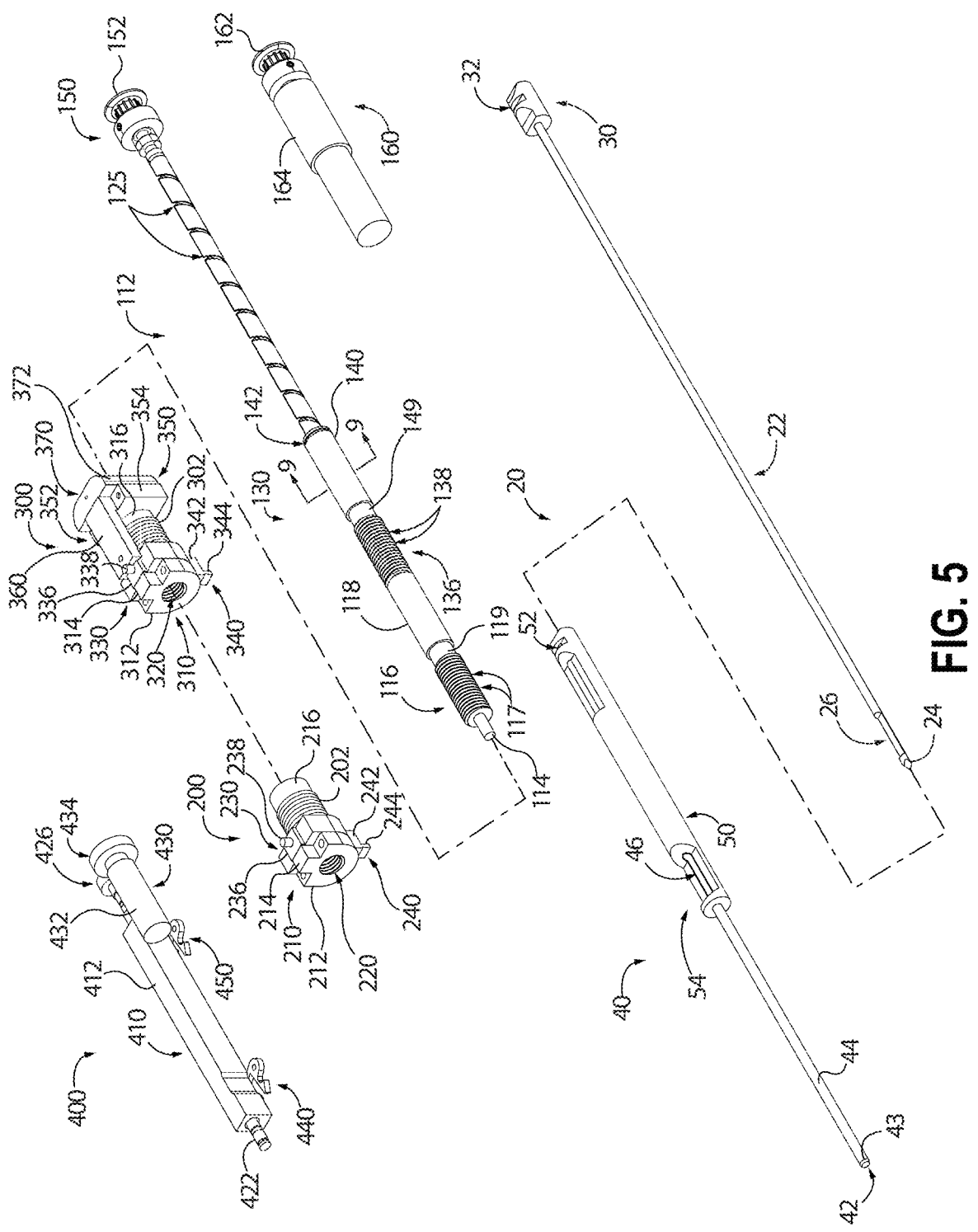
FIG. 5 depicts an exploded view of the drive assembly of FIG. 4.
Figure 6:
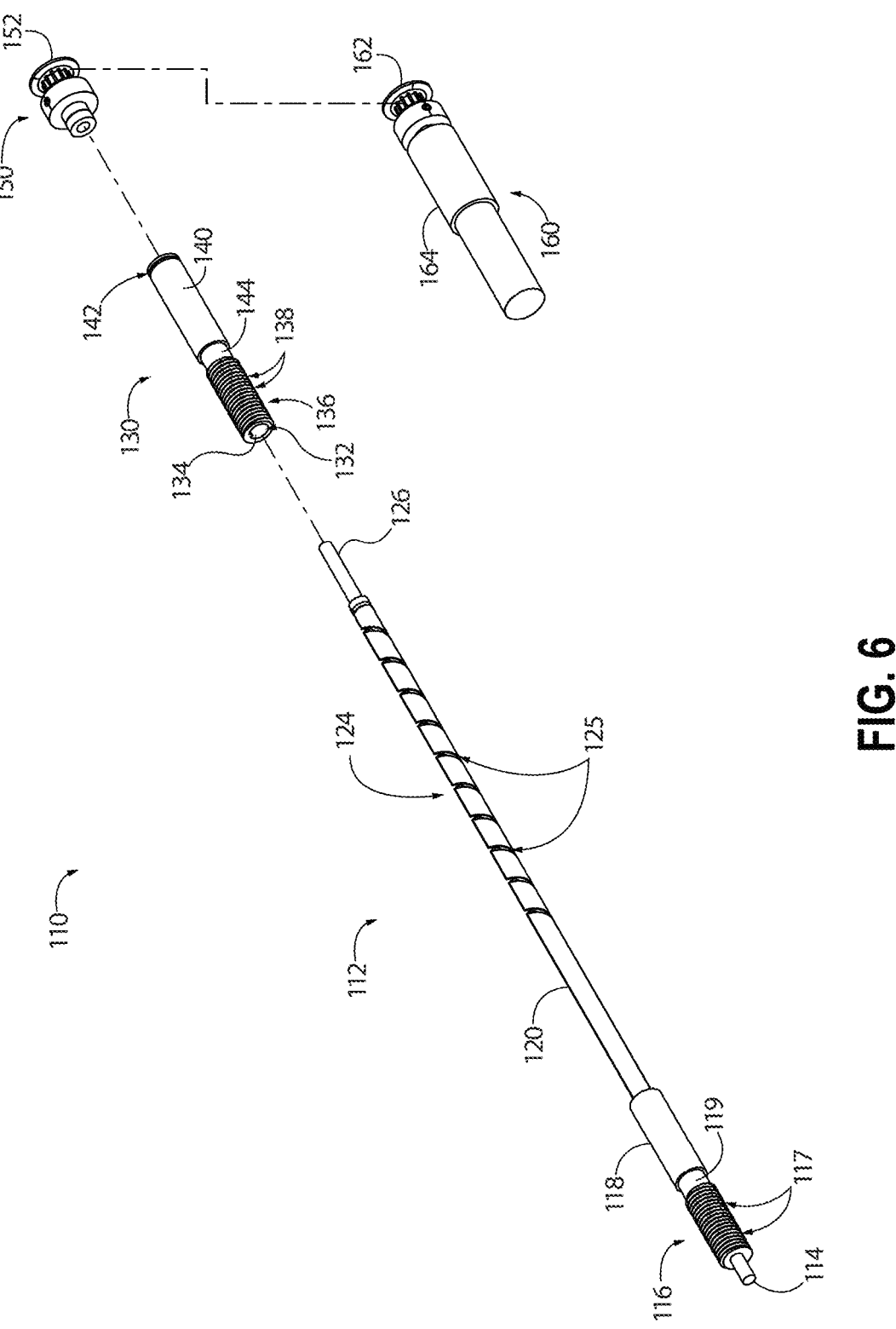
FIG. 6 depicts an exploded view of a needle cocking assembly of the drive assembly of FIG. 4.

FIGS. 4 and 5 show the internal components of body (12) of biopsy device (10) with outer housing (14) removed. As can be seen, inside outer housing (14), body (12) includes a drive assembly (100). Drive assembly (100) is generally configured to engage needle assembly (20) to drive piercer (22) and cutter (40) through a predetermined sequence of movements to thereby pierce tissue and acquire a plurality of tissue samples with a single insertion of needle assembly (20) into a patient. Although not shown, it should be understood that outer housing (14) defines various internal geometries that support or otherwise engage drive assembly (100). As will be understood, such internal geometries are used to provide relative movement of various components of drive assembly (100) relative to other components of drive assembly (100) and/or outer housing (14).

Drive assembly (100) comprises a needle cocking assembly (110), a cutter drive assembly (200), a piercer drive assembly (300), and a release assembly (400). Generally, and as will be described in greater detail below, needle cocking assembly (110) engages cutter drive assembly (200) and piercer drive assembly (300) to cock cutter drive assembly (200) and piercer drive assembly (300), which correspondingly cock cutter (40) and piercer (22). Release assembly (400) also engages cutter drive assembly (200) and piercer drive assembly (300) to selectively release and fire cutter drive assembly (200) and piercer drive assembly (300) to thereby selectively release and fire cutter (40) and piercer (22).

Figure 7:
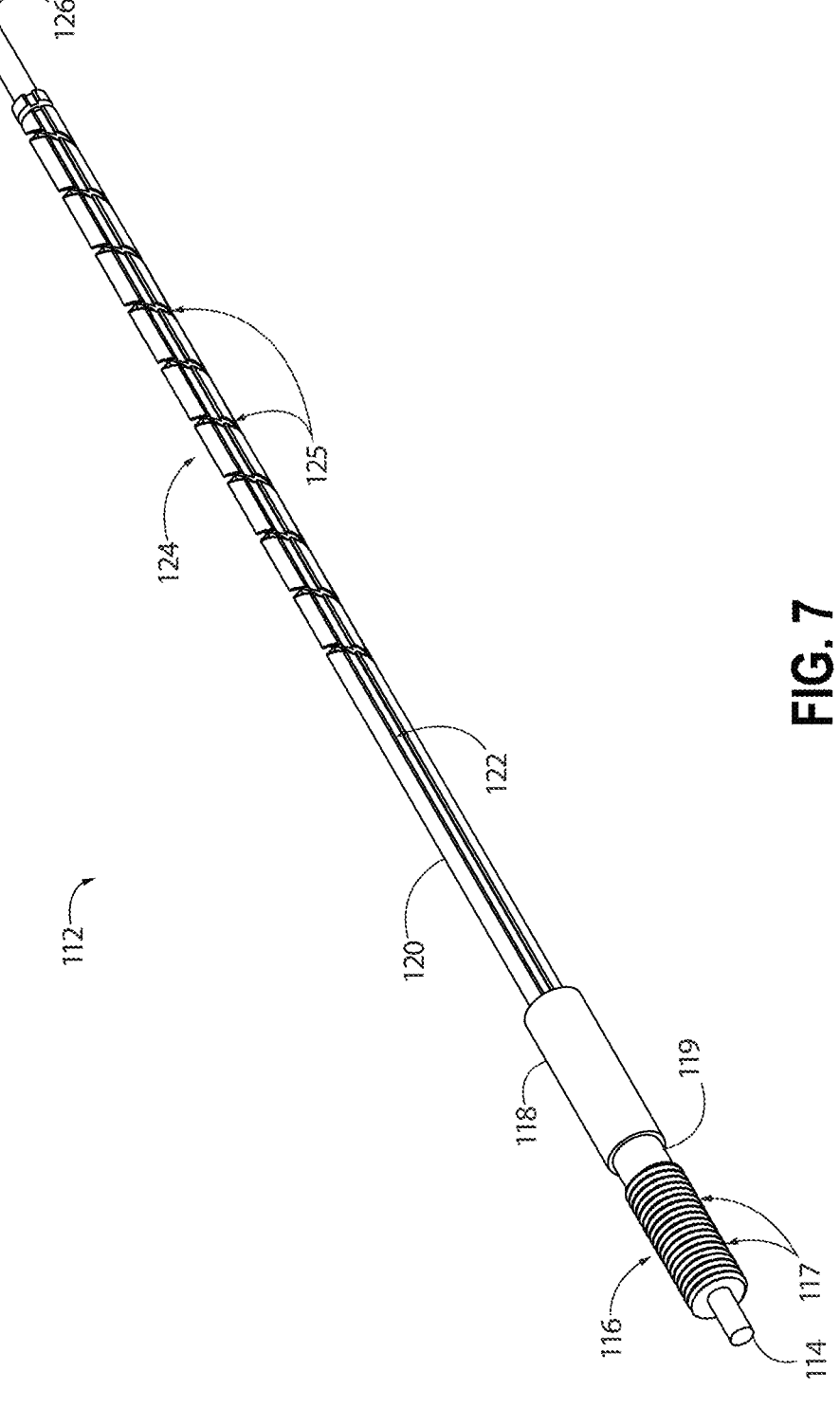
FIG. 7 depicts a perspective view of a lead screw of the needle cocking assembly of FIG. 6.

Needle cocking assembly (110) is best seen in FIGS. 6-9. As can be seen, needle cocking assembly (110) comprises a lead screw (112), a carriage nut (130), a drive member (150), and a motor assembly (160). Lead screw (112) is best seen in FIG. 7. As can be seen lead screw (112) is generally an elongate multi-threaded rod. Lead screw (112) comprises a distal end (114), first threaded portion (116), a slide stop portion (118), a non-threaded portion (120), a keyway (122), a second threaded portion (124), and a proximal end (126).

Distal end (114) of lead screw (112) generally comprises a cylindrical shape extending distally from first threaded portion (116). Distal end (114) is configured to be received by at least a portion of outer housing (14) or another intermediate connecting member, such as a bearing, to permit lead screw (112) to rotate about a fixed axis. Thus, it should be understood that distal end (114) generally acts as a boss or locating feature to permit rotation of lead screw (112).

First threaded portion (116) is disposed proximally of distal end (114). First threaded portion (116) includes threads (117) which have a relatively fine pitch. As will be described in greater detail below, threads (117) are generally configured to engage a portion of cutter drive assembly (200) to convert rotational motion of lead screw (112) into translation of at least a portion of cutter drive assembly (200). This conversion of motion generally results in proximal and distal translation of at least a portion of cutter drive assembly (200), which results in cocking of cutter drive assembly (200).

Slide stop portion (118) is disposed proximally of first threaded portion (116) and distally of keyway (122), second threaded portion (124) and proximal end (126). Slide stop portion (118) comprises a generally cylindrical shape. The diameter of slide stop portion (118) generally corresponds to the major pitch diameter of first threaded portion (116). As will be described in greater detail below, these size and shape characteristics of slide stop portion (118) permit slide stop portion (118) to provide coaxial support of at least a portion of cutter drive assembly (200) as cutter drive assembly (200) moves relative to lead screw (112).

The diameter of slide stop portion (118) is also generally greater than the diameter of non-threaded portion (120) of lead screw (112). As will be understood, this differential in diameter between slide stop portion (118) and non-threaded portion (120) permits slide stop portion (118) to act as a mechanical stop feature. As will be described in greater detail below, this mechanical stop feature is configured to limit distal translation of carriage nut (130) as carriage nut (130) moves along lead screw (112).

Between slide stop portion (118) and first threaded portion (116), lead screw (112) defines an indented portion (119). As will be described in greater detail below, indented portion (119) is generally configured to permit a portion of cutter drive assembly (200) to "free-wheel" when cutter drive assembly (200) is disposed in axial alignment with indented portion (119). It should be understood that the term "free-wheel" used herein refers to the ability of lead screw (112) to continue to rotate without additional proximal translation of cutter drive assembly (200) and without binging between lead screw (112) and at least a portion of cutter drive assembly (200). It should be understood that during free-wheeling, at least a portion of cutter drive assembly (200) is generally disengaged from first threaded portion (116) of lead screw (112). However, it should be understood that the length of indented portion (119) is sufficiently limited such that when rotation of lead screw (112) is reversed, at least a portion of cutter drive assembly (200) reengages with first threaded portion (116) of lead screw (112). Further details of the relationship between indented portion (119), first threaded portion (116) and cutter drive assembly (200) will be described in greater detail below.

As shown in FIG. 7, non-threaded portion (120) is proximally adjacent to slide stop portion (118). Non-threaded portion (120) is also distally adjacent to second threaded portion (124) and is disposed distally of proximal end (126). Non-threaded portion (120) is generally of a cylindrical shape without threads or other features. However, as can be seen in FIG. 7, keyway (122) extends through non-threaded portion (120) and through second threaded portion (124). As previously described above with respect to slide stop portion (118), non-threaded portion (120) has a diameter that is generally less than the diameter defined by slide stop portion (118). As also described above, this differential in diameter between non-threaded portion (120) and slide stop portion (118) permits non-threaded portion (120) to provide a mechanical stop feature for carriage nut (130), as will be described in greater detail below.

Second threaded portion (124) is disposed between non-threaded portion (120) and proximal end (126), with non-threaded portion (120) distal of second threaded portion (124) and proximal end (126) proximal of non-threaded portion (120). Second threaded portion (124) includes a plurality of relatively course threads (125). Threads (125) are generally course relative to threads (117) of first threaded portion (116). Thus it should be understood that with both threads (125, 117) acting to transfer rotary movement into axial translation, threads (125) of second threaded portion (124) will generally provide faster translation from the same rotary input relative to threads (117) of first threaded portion (116).

Second threaded portion (124) of the present example is configured to engage at least a portion of piercer drive assembly (300). As will be described in greater detail below, threads (125) of second threaded portion (124) are generally configured to convert rotary motion of lead screw (112) into axial translation of at least a portion of piercer drive assembly (300). This conversion of rotary motion into translation permits piercer drive assembly to translate piercer (22) for the purpose of tissue collection via tissue collection feature (54).

In the present example, second threaded portion (124) and non-threaded portion (120) are arranged such that non-threaded portion (120) defines a length. The length of non-threaded portion (120) is generally just greater than the approximate length of carriage nut (130). As will be understood, the length of non-threaded portion permits carriage nut (130) to be axially translated by piercer drive assembly (300) until being stopped by slide stop portion (120). Once translation is ceased by slide stop portion (120), however, non-threaded portion (120) permits lead screw (112) to "free-wheel" relative to piercer drive assembly (300). It should be understood that the term "free-wheel" used herein refers to the ability of lead screw (112) to continue to rotate without additional translation of piercer drive assembly (300) and without binding between lead screw (112) and piercer drive assembly (300). During free-wheeling, piercer drive assembly (300) generally disengaged from second threaded portion (124). However, it should be understood that the length of non-threaded portion remains limited to an extent such that when rotation of lead screw (112) is reversed, piercer drive assembly (300) reengages with second threaded portion (124). Further details of the relationship between non-threaded portion (120), second threaded portion (124) and piercer drive assembly (300) will be described in greater detail below.

Returning to FIG. 6, rotation of lead screw (112) is provided by drive member (150) and motor assembly (160). In particular, drive member (150) of the present example is configured to be fixedly secured to proximal end (126) of lead screw (112). Drive member (150) includes a rotary communication feature (152) which is configured to transmit rotary motion from a rotary communication feature (162) of motor assembly (160) to lead screw (112). In the present example, rotary communication features (152, 162) are configured as belt drives such that rotary motion is communicated via a belt (not shown). It should be understood that although rotary communication features (152, 162) are shown as using a belt drive, any other suitable rotary communication feature may be used. For instance, in some examples rotary communication features (152, 162) can include one or more gears with varying gear ratios to communicate rotary motion from motor assembly (160) to lead screw (112). Of course, in other examples, rotary communication features (152, 162) can be omitted entirely such that motor assembly (160) includes a direct drive that directly communicates rotary motion to lead screw (112).

As described above, motor assembly (160) includes a rotary communication feature (162). Additionally, motor assembly (160) includes a rotary power source (164). Rotary power source (164) of the present example includes an electric motor. In other examples, rotary power source (164) may include any other suitable power source such as a pneumatic motor, a piezo electric motor, and/or etc.

Figure 8:
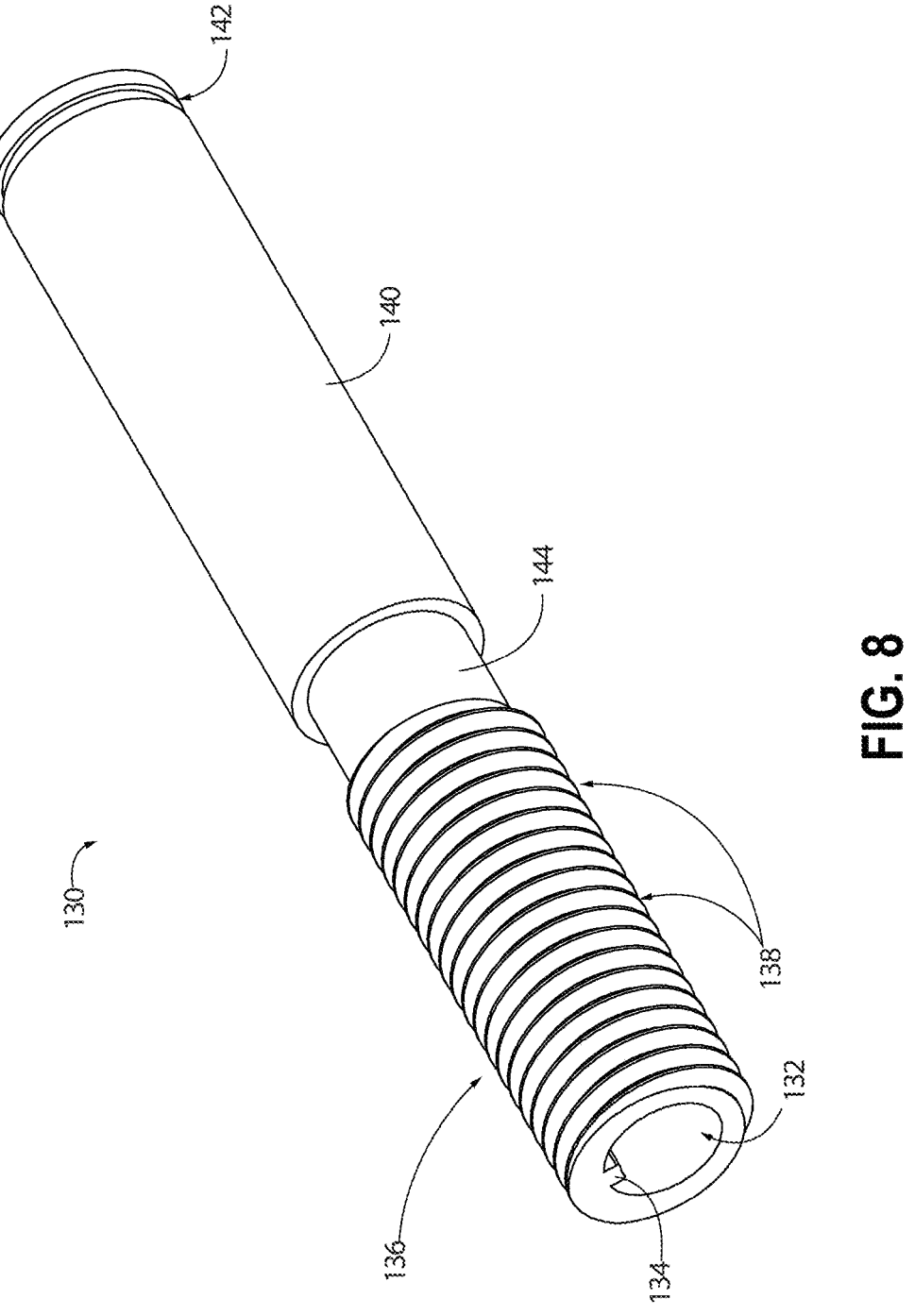
FIG. 8 depicts a perspective view of a carriage nut of the needle cocking assembly of FIG. 6.

FIG. 8 shows carriage nut (130) in greater detail. As can be seen, carriage nut (130) comprises a generally cylindrical shape with a bore (132) extending entirely therethough. Extending inwardly into bore (132) is a key (134). Key (134) extends axially through at least a portion of the length of carriage nut (130). As will be described in greater detail below, key (134) is generally configured to engage keyway (122) of lead screw (112) such that carriage nut (130) is generally configured to rotate in conjunction with lead screw (112).

On the exterior of carriage nut (130), carriage nut (130) defines a threaded portion (136) and a slide portion (140). Threaded portion (136) includes a plurality of threads (138). Threads (138) generally include a pitch that is relatively fine and generally equivalent to the pitch of threads (117) of first threaded portion (116) described above with respect to lead screw (112). As will be described in greater detail, threads (138) of threaded portion (136) are generally configured to engage at least a portion of piercer drive assembly (300) to move at least a portion of piercer drive assembly (300) thorough a variety of positions to thereby cock and fire piercer (22).

Slide portion (140) defines a generally cylindrical shape having an outer diameter. The outer diameter of slide portion (140) approximately corresponds to the major diameter of threaded portion (136). As will be described in greater detail below, this correspondence in diameters permits at least a portion of cutter drive assembly (200) to freely slide over both slide portion (140) and threaded portion (136), while remaining generally coaxial with carriage nut (130).

Adjacent to the proximal end of carriage nut (130), slide portion (140) defines an annular channel (142). As will be described in greater detail below, annular channel (142) is configured to receive at least a portion of piercer drive assembly (300) to axially secure at least a portion of piercer drive assembly (300) to carriage nut (130). However, as will also be described in greater detail below, any portion of cutter drive assembly (300) axially secured to carriage nut (130) via cannula channel (142) is rotatably unsecured such that carriage nut (130) can rotate relative to piercer drive assembly (300).

Disposed between slide portion (140) and threaded portion (136), carriage nut (130) defines an indented portion (144). Indented portion (144) is defined by an outer diameter that is generally less than the major diameter of threaded portion (136) and the outer diameter of slide portion (140). In addition, indented portion (144) defines a length. As will be described in greater detail below, the length of indented portion (144) is generally approximately equivalent to at least a portion of piercer drive assembly (300) to permit a portion of piercer drive assembly (300) to free-wheel relative to carriage nut (130).

As will be described in greater detail below, indented portion (144) is generally configured to permit a portion of piercer drive assembly (300) to free-wheel when piercer drive assembly (300) is disposed in axial alignment with indented portion (144). As similarly discussed above with respect to non-threaded portion (120) of lead screw (112), the term "free-wheel" used herein refers to the ability of carriage nut (130) to continue to rotate without additional proximal translation of piercer drive assembly (300) and without binging between carriage nut (130) and at least a portion of piercer drive assembly (300). It should be understood that during free-wheeling, at least a portion of piercer drive assembly (300) is generally disengaged from threaded portion (136) of carriage nut (130). However, it should be understood that the length of indent portion (144) is sufficiently limited such that when rotation of carriage nut (130) is reversed, at least a portion of piercer drive assembly (300) reengages with threaded portion (136) of carriage nut (130). Further details of the relationship between indented portion (144), threaded portion (136) and piercer drive assembly (300) will be described in greater detail below.

Figure 9:
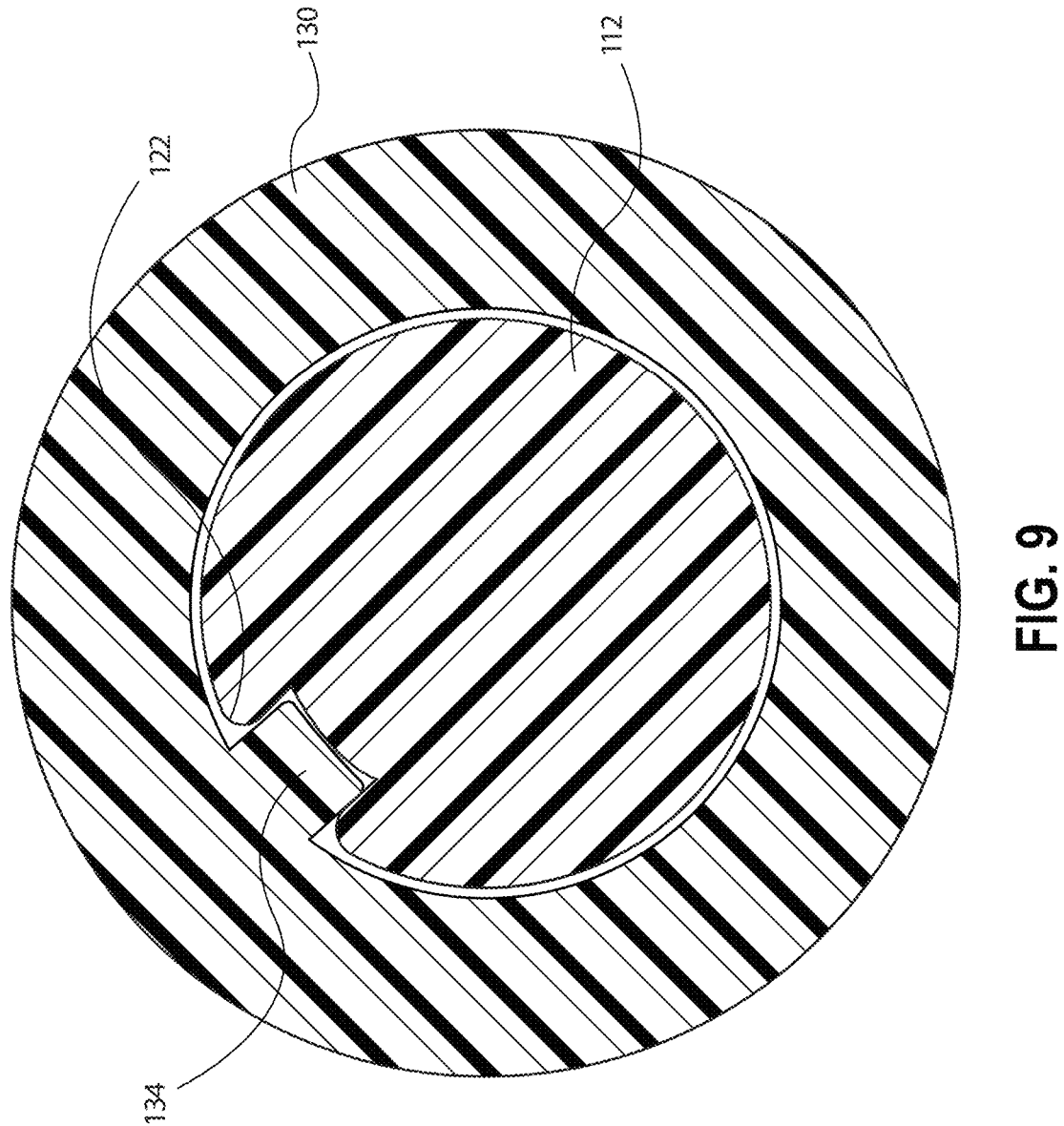
FIG. 9 depicts a side cross-sectional view of the needle cocking assembly of FIG. 6, the cross-section taken along line 9-9 of FIG. 5.

FIG. 9 shows carriage nut (130) coaxially disposed on lead screw (112). As can be seen, when carriage nut (130) is disposed on lead screw (112), key (134) extends into keyway (122) of lead screw (112). Accordingly, it should be understood that keyway (122) of lead screw (112) is configured to engage key (134) such that rotation of lead screw (112) results in corresponding rotation of carriage nut (130). It should be understood that since keyway (122) extends through both second threaded portion (124) and non-threaded portion (120) of lead screw (112), keyway (122) is configured to engage key (134) of carriage nut (130) as carriage nut (130) travels axially about second threaded portion (124) and non-threaded portion (120) of lead screw (112).

Figures 10A, 10B:
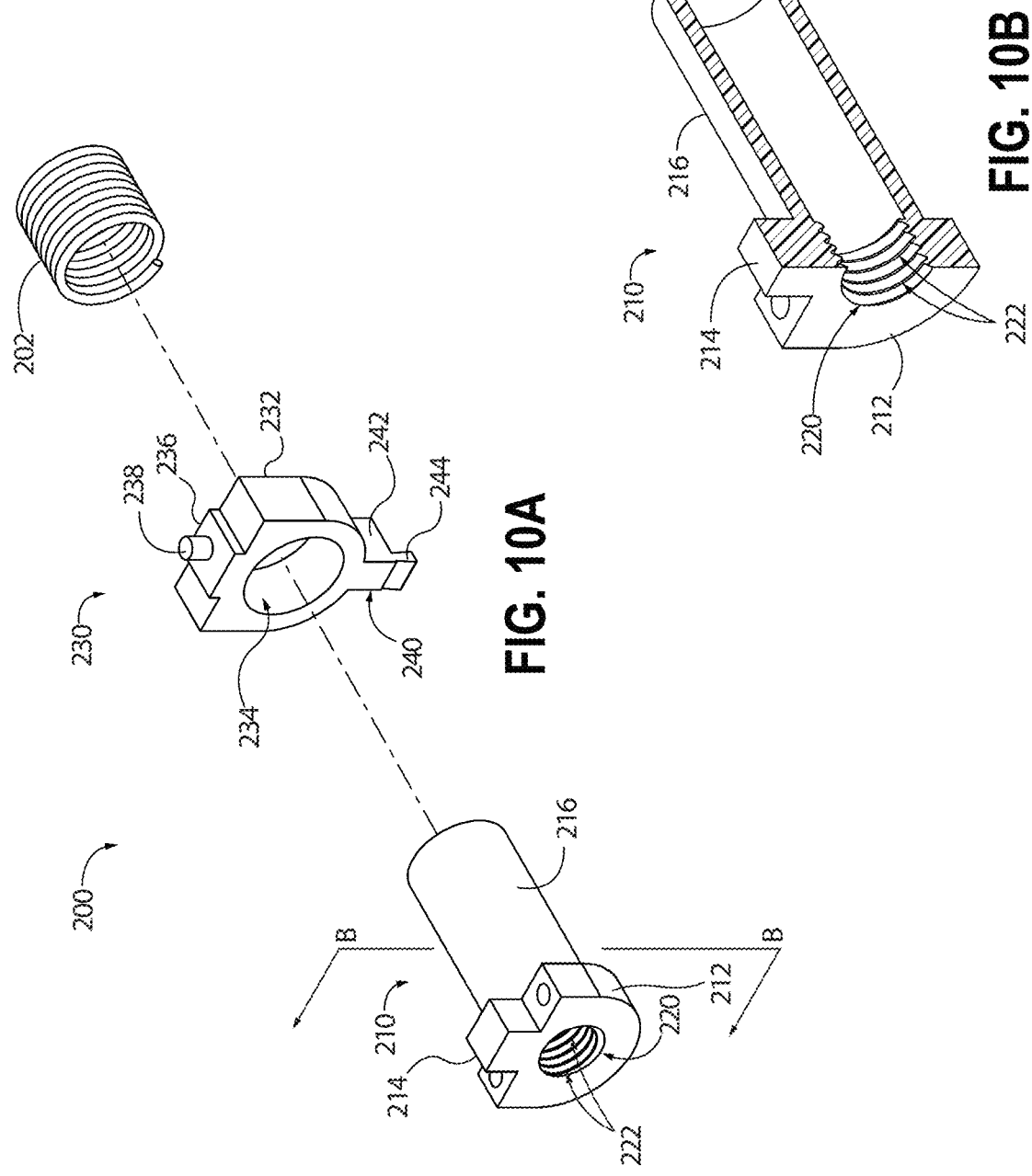
FIG. 10A depicts an exploded view of a cutter drive assembly of the drive assembly of FIG. 4.
FIG. 10B depicts a cross-sectional view of a cocking member of the cutter drive assembly of FIG. 10A, the cross-section taken along line B-B of FIG. 10A.

FIG. 10A shows cutter actuation assembly (200) in greater detail. In particular, cutter actuation assembly (200) comprises a cocking member (210), an actuation member (230), and a resilient member (202). Cocking member (210) comprises a stop portion (212), a slide portion (216), and a bore (220) extending axially though cocking member (210). Stop portion (212) is generally configured to act as a mechanical stop for actuation member (230). Accordingly, stop portion (212) forms a shape that is similar to a partially cylindrical flange or another similar feature. As will be described in greater detail below, this mechanical stop feature of stop portion (212) is generally configured to manipulate motion of actuation member (230) as actuation member (230) moves cutter (40) through a predetermined sequence of motion.

Stop portion (212) further defines an alignment tab (214) extending upwardly relative to bore (220). Alignment tab (214) comprises a generally rectangular or cubic shape. In other examples, alignment tab (214) may comprise any other suitable shape such as cylindrical, ball-shaped, triangular, and/or etc. Although not shown, it should be understood that alignment tab (214) is configured to be received within a corresponding channel or track disposed within outer housing (14) or an intermediate housing (not shown). Such a channel or track is configured to restrict motion of cocking member (210) to a particular predetermined axial path. Such a channel or track is further configured to prevent rotation of cocking member (210) relative to lead screw (112) to thereby permit lead screw (112) to drive axial motion of cocking member (210), as will be described in greater detail below.

Slide portion (216) of cocking member (210) extends proximally from stop portion (212). Slide portion (216) comprises a generally cylindrical outer surface that is configures to receive actuation member (230). As will be described in greater detail below, actuation member (230) is generally coaxially slidable on slide portion (216) to actuate cutter (40) through a predetermined sequence of motion. However, slide portion (216) has a diameter that is less than the size or diameter of stop portion (212). Accordingly, it should be understood that actuation member (230) is generally coaxially slidable on slide portion (216) until actuation member (230) reaches stop portion (212). At which point, any additional distal sliding relative to slide portion (216) is ceased by stop portion (212).

As described above, bore (220) of cocking member (210) extends through both stop portion (212) and slide portion (216). Bore (220) defines a plurality of threads (222) extending inwardly into bore (220). As best seen in FIG. 10B, threads (222) of bore (220) extend through only the length of bore (220) corresponding to the length of stop portion (212). Although threads (222) of the present example only extend partially though bore (220), it should be understood that in other examples threads (222) can extend for the entire length of bore (220). However, it should be understood that in such examples certain complementary features of lead screw (112) may require adjustment in length/size to accommodate the additional length of threads (222).

Bore (220) is configured to receive at least a portion of lead screw (112). In particular, bore (220) is configured to receive first threaded portion (116), indented portion (119), and/or slide stop portion (118) of lead screw (112) at various stages during the cutting cycle and the tissue acquisition cycle, as will be described in greater detail below. As will be understood, threads (222) are configured to engage threads (117) of first threaded portion (116). Thus, it should be understood that rotation of lead screw (112) relative to cocking member (210) will generally result in axial translation of cocking member (210) relative to lead screw (112).

As described above, threads (222) of bore (220) are generally limited to the length of stop portion (212). Because a portion of bore (220) in the present example is un-threaded (e.g., the portion corresponding to slide portion (216)), it should be understood that bore (220) can receive at least a portion of slide stop portion (118) of lead screw (112). However, because slide stop portion (118) defines a diameter approximately equivalent to the major diameter of first threaded portion (116) of lead screw (112), it should be understood that as cocking member (210) moves proximally relative to lead screw (112) such relative motion will only be permitted until threads (222) reach slide stop portion (118) of lead screw (112). Once threads (222) reach slide stop portion (118) of lead screw (112), an interference between the major diameter of threads (222) and the outer diameter of slide stop portion (118) will prevent further proximal movement of cocking member (210). Moreover, threads (222) at this stage will be adjacent to intended portion (119) and therefore disengaged with threads (117) of first threaded portion (116).

Actuation member (230) comprises a body (232), an alignment tab (236), and an actuation tab (240). Body (232) comprises a shape that is generally similar to stop portion (212) described above with respect to cocking member (210). Like with stop portion (212), body (232) defines a bore (234) extending through body (232). Bore (234) of body (232) is configured to receive slide portion (216) of cocking member (210). Thus, it should be understood that actuation member (230) is generally coaxially slidable with slide portion (216) of cocking member (210).

Alignment tab (236) extends upwardly from body (232). Like with alignment tab (214) of cocking member (210), alignment tab (236) of actuation member (230) is configured to engage a channel or track disposed in outer housing (14) or an intermediate housing (not shown). As similarly discussed above, this configuration generally permits such a channel or tack to restrict the motion of actuation member (230) to a predetermined path. However, unlike alignment tab (214) discussed above, alignment tab (236) of actuation member (230) only extends for a relatively small distance from body (232). Instead of alignment tab (236) extending for the full extent as seen with alignment tab (214), a portion of alignment tab (236) of actuation member (230) is replaced with a release member (238). Release member (238) comprises a generally cylindrical shape. As will be described in greater detail below, release member (238) is generally configured to be received by release assembly (400) to temporarily hold actuation member (230) in a cocked position and then selectively release actuation member (230) via actuation of release assembly (400).

Actuation tab (240) extends downwardly from body (232). Actuation tab (240) comprises an upper portion (242) and a lower portion (244). Upper portion (242) comprises a generally rectangular shape. Although not shown, it should be understood that in some examples upper portion (242) can be configured to be received within a cannel or track of outer housing (14) or an intermediate internal housing (not shown) thereof. In such examples, upper portion (242) functions to restrict motion of actuation member (230) to a predetermined path.

Lower portion (244) of actuation tab (240) extends downwardly from upper portion (242). Lower portion (244) is generally configured to be received within receiving feature (52) of cutter (40). As will be described in greater detail below, when lower portion (244) is received within receiving feature (52) of cutter (40), actuation member (230) is generally permitted to drive cutter (40) through a predetermined sequence of movements via lower portion (244). Although not show, it should be understood that in examples where upper portion (242) is received within a channel or track of outer housing (14) or an intermediate internal housing, such a channel or track may include an opening or additional channel to prevent lower portion (244) to extend through such a channel or track to receiving feature (52) of cutter (40).

When cutter drive assembly (200) is assembled (e.g., as seen in FIG. 4), spring (202) is disposed adjacent to the proximal end of actuation member (230). In addition, spring (202) is disposed coaxially around slide portion (216) of cocking member (210) and/or coaxially around slide stop portion (118) of lead screw (112), depending on the particular stage of operation of drive assembly (100). As will be described in greater detail below, spring (202) is generally configured to drive actuation member (230) distally after actuation member (230) is released by release assembly (400). Spring (202) generally defines an outer diameter that approximately corresponds to the outer diameter of slide portion (216) of cocking member (210). Although spring (202) of the present example is shown as a coil spring, it should be understood that any other suitable resilient member may be used as will be apparent to those of ordinary skill in the art in view of the teachings herein.

Figures 11A, 11B:
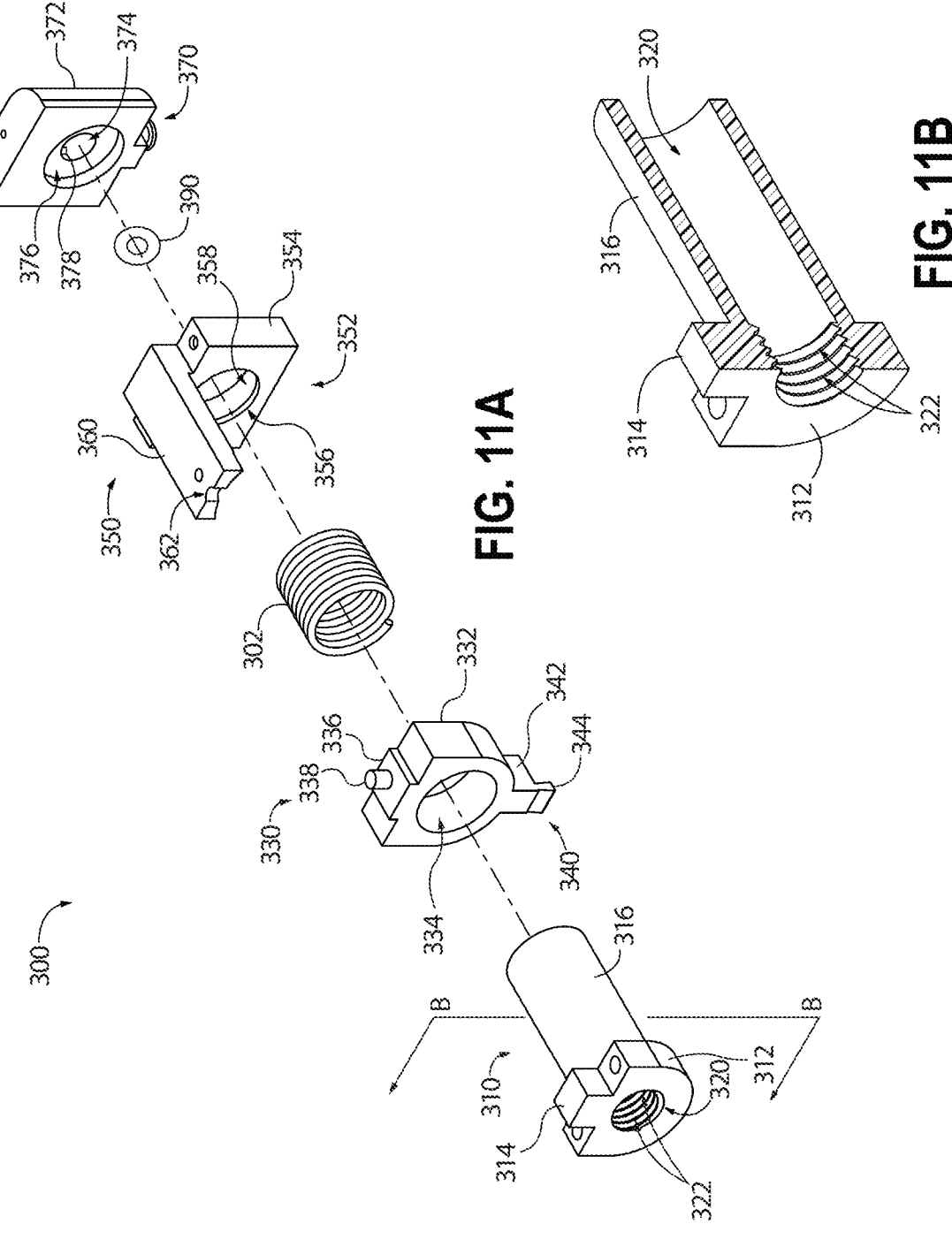
FIG. 11A depicts an exploded view of a piercer drive assembly of the drive assembly of FIG. 4.
FIG. 11B depicts a cross-sectional view of a cocking member of the piercer drive assembly of FIG. 11A, the cross-section taken along line B-B of FIG. 11A.

FIG. 11A shows piercer drive assembly (300) in greater detail. As can be seen, piercer drive assembly (300) comprises a cocking member (310), an actuation member (330), a piercer retraction assembly (350), and a spring (302). Cocking member (310) of piercer drive assembly (300) is similar to cocking member (210) of cutter drive assembly (200). In particular, like with cocking member (210), cocking member (310) comprises a stop portion (312), a slide portion (316), and a bore (320) extending axially though cocking member (310). Stop portion (312) is generally configured to act as a mechanical stop for actuation member (330). Accordingly, stop portion (312) forms a shape that is similar to a partially cylindrical flange or another similar feature. As will be described in greater detail below, this mechanical stop feature of stop portion (312) is generally configured to manipulate motion of actuation member (330) as actuation member (330) moves piercer (22) through a predetermined sequence of motion.

Stop portion (312) further defines an alignment tab (314) extending upwardly relative to bore (320). Alignment tab (314) comprises a generally rectangular or cubic shape. In other examples, alignment tab (314) may comprise any other suitable shape such as cylindrical, ball-shaped, triangular, and/or etc. Although not shown, it should be understood that alignment tab (314) is configured to be received within a corresponding channel or track disposed within outer housing (14) or an intermediate housing (not shown). Such a channel or track is configured to restrict motion of cocking member (310) to a particular predetermined axial path. Such a channel or track is further configured to prevent rotation of cocking member (310) relative to lead screw (112) and carriage nut (130) to thereby permit lead screw (112) and carriage nut (130) to drive axial motion of cocking member (310), as will be described in greater detail below.

Slide portion (316) of cocking member (310) extends proximally from stop portion (312). Slide portion (316) comprises a generally cylindrical outer surface that is configures to receive actuation member (330). As will be described in greater detail below, actuation member (330) is generally coaxially slidable on slide portion (316) to actuate cutter (40) through a predetermined sequence of motion. However, slide portion (316) has a diameter that is less than the size or diameter of stop portion (312). Accordingly, it should be understood that actuation member (330) is generally coaxially slidable on slide portion (316) until actuation member (330) reaches stop portion (312). At which point, any additional distal sliding relative to slide portion (316) is ceased by stop portion (312).

As described above, bore (320) of cocking member (310) extends through both stop portion (312) and slide portion (316). Bore (320) defines a plurality of threads (322) extending inwardly into bore (320). As can best be seen in FIG. 11B, threads (322) of bore (320) extend through only the longitudinal length of bore (320) corresponding to the length of stop portion (312). In other examples, threads (322) can alternatively extend for the entire length of bore (320). However, it should be understood that in such examples certain complementary features of carriage nut (130) may require adjustment in length/size to accommodate the additional length of threads (322).

Bore (320) is configured to receive at least a portion of carriage nut (130). In particular, bore (320) is configured to receive threaded portion (136), indented portion (144), and/ or slide portion (140) of carriage nut (130) at various stages during the cutting cycle and the tissue acquisition cycle, as will be described in greater detail below. As will be understood, threads (322) are configured to engage threads (138) of threaded portion (136) of carriage nut (130). Thus, it should be understood that rotation of carriage nut (130) via lead screw (112) relative to cocking member (310) will generally result in axial translation of cocking member (310) relative to carriage nut (130) and lead screw (112).

As described above, threads (322) of bore (320) are generally limited to the length of stop portion (312). Because a portion of bore (320) in the present example is un-threaded (e.g., the portion corresponding to slide portion (316)), it should be understood that bore (320) can receive at least a portion of slide portion (140) of carriage nut (130). However, because slide portion (140) defines a diameter approximately equivalent to the major diameter of threaded portion (136) of carriage nut (130), it should be understood that as cocking member (310) moves proximally relative to carriage nut (130) and lead screw (112) such relative motion will only be permitted until threads (322) reach slide portion (140) of carriage nut (130). Once threads (322) reach slide portion (140) of carriage nut (130), an interference between the major diameter of threads (322) and the outer diameter of slide portion (140) will prevent further proximal movement of cocking member (310). Moreover, threads (322) at this stage will be adjacent to intended portion (144) and therefore disengaged with threads (138) of threaded portion (136).

Actuation member (330) comprises a body (332), an alignment tab (336), and an actuation tab (340). Body (332) comprises a shape that is generally similar to stop portion (312) described above with respect to cocking member (310). Like with stop portion (312), body (332) defines a bore (334) extending through body (332). Bore (334) of body (332) is configured to receive slide portion (316) of cocking member (310). Thus, it should be understood that actuation member (330) is generally coaxially slidable with slide portion (316) of cocking member (310).

Alignment tab (336) extends upwardly from body (332). Like with alignment tab (314) of cocking member (310), alignment tab (336) of actuation member (330) is configured to engage a channel or track disposed in outer housing (14) or an intermediate housing (not shown). As similarly discussed above, this configuration generally permits such a channel or tack to restrict the motion of actuation member (330) to a predetermined path. However, unlike alignment tab (314) discussed above, alignment tab (336) of actuation member (330) only extends for a relatively small distance from body (332). Instead of alignment tab (336) extending for the full extent as seen with alignment tab (314), a portion of alignment tab (336) of actuation member (330) is replaced with a release member (338). Release member (338) comprises a generally cylindrical shape. As will be described in greater detail below, release member (338) is generally configured to be received by release assembly (400) to temporarily hold actuation member (330) in a cocked position and then selectively release actuation member (330) via actuation of release assembly (400).

Actuation tab (340) extends downwardly from body (332). Actuation tab (340) comprises an upper portion (342) and a lower portion (344). Upper portion (342) comprises a generally rectangular shape. Although not shown, it should be understood that in some examples upper portion (342) can be configured to be received within a cannel or track of outer housing (14) or an intermediate internal housing (not shown) thereof. In such examples, upper portion (342) functions to restrict motion of actuation member (330) to a predetermined path.

Lower portion (344) of actuation tab (340) extends downwardly from upper portion (342). Lower portion (344) is generally configured to be received within receiving feature (32) of piercer (22). As will be described in greater detail below, when lower portion (344) is received within receiving feature (32) of piercer (22), actuation member (330) is generally permitted to drive piercer (22) through a predetermined sequence of movements via lower portion (344). Although not show, it should be understood that in examples where upper portion (342) is received within a channel or track of outer housing (14) or an intermediate internal housing, such a channel or track may include an opening or additional channel to prevent lower portion (344) to extend through such a channel or track to receiving feature (32) of piercer (22).

Piercer retraction assembly (350) is disposed proximally of cocking member (310) and actuation member (330). As will be described in greater detail below, piercer retraction assembly (350) is generally configured to axially translate piercer drive assembly (300) relative to lead screw (112). Piercer retraction assembly (350) comprises a first retraction member (352) and a second retraction member (370), and a retainer (390) disposed between first retraction member (352) and second retraction member (370).

First retraction member (352) comprises a body (354) and a support arm (360). Body (354) defines a bore (356) extending entirely through body (354). Body (354) further includes a counter-bore (358) disposed adjacent to bore (356). Counter-bore (358) extends distally only partially though body (354) from the proximal end thereof. As will be described in greater detail below, bore (356) and counter-bore (358) are generally sized to receive slide portion (316) of cocking member (310) and slide portion (140) of carriage nut (130). Bore (356) defines a diameter that is generally undersized relative to a diameter defined by retainer (390), while counter-bore (358) defines a diameter that is generally oversized relative to the diameter defined by retainer (390). As will be described in greater detail below, this difference in diameter between bore (356) and counter-bore (358) is configured to secure retainer (390) between first retraction member (352) and second retraction member (370).

Support arm (360) of first retraction member (352) extends distally from body (354). The distal extension of support arm (360) defines a length that is generally equivalent to spring (302) in a compressed state. On the distal end of support arm (360), support arm (360) defines a receiving indentation (362). Receiving indentation (362) is generally configured to receive at least a portion of release member (338) of actuation member (330). As will be described in greater detail below, receiving indentation (362) is generally configured to operate in conjunction with at least a portion of release assembly (400) to selectively hold release member (338) in a predetermined position relative to first retraction member (352).

Second retraction member (370) comprises a body (372) having a generally rectangular shape. Body (372) defines a bore (374) and a counter-bore (376) disposed coaxially with bore (374). Bore (374) extends entirely though body (372), while counter-bore (376) extends distally through only a portion of body (372) from the distal end thereof. Bore (374) and counter-bore (376) are both configured to receive at least a portion of lead screw (112) such that lead screw (112) can extend entirely though second retraction member (370). However, a diameter defined by counter-bore (376) is larger than a diameter defined by bore (374) to accommodate retainer (390) within counter-bore (376). It should be understood that this differential in the diameters of bore (374) and counter-bore (376) is configured to prevent proximal movement of retainer (390) relative to second retraction member (370) such that retainer (390) is generally held between first retraction member (352) and second retraction member (370).

Bore (374) further includes a protrusion (378) extending downwardly into the space defined by bore (374). Protrusion (378) comprises a generally cylindrical shape, although any other suitable shape may be used. As will be described in greater detail below, protrusion (378) is configured to engage threads (125) of lead screw (112) to drive translation of second retraction member (370) in response to rotation of lead screw (112).

As described above, retainer (390) is disposed between first retraction member (352) and second retraction member (370). Retainer (390) generally comprises a circular shape similar to a washer or other similar structure. Retainer (390) includes a bore (392) extending entirely though retainer (390). Bore (392) of retainer (390) is sized to permit retainer (390) to fit within annular channel (142) of carriage nut (130). Because retainer (390) is secured between first retraction member (352) and second retraction member (370), it should be understood that when retainer (390) generally axially secures movement of carriage nut (130) relative to piercer retraction assembly (350) via engagement between retainer (390) and annular channel (142). Thus, it should be understood that axial movement of carriage nut (130) will generally result in axial movement of piercer retraction assembly (350). As will be described in greater detail below, this relationship between movement of carriage nut (130) and piercer retraction assembly (350) generally results in retraction of piercer (22) during the tissue acquisition cycle.

While retainer (390) axially secures movement of carriage nut (130) relative to piercer retraction assembly (350), it should be understood that carriage nut (130) is rotatably movable relative to piercer retraction assembly (350). In other words, retainer (390) only secures axial movement of carriage nut (130), not rotational movement. Although not shown, it should be understood that in some examples retainer (390) can be adjacent to one or more bearings to disposed within either or both counter-bores (358, 376) of first retraction member (352) and second retraction member (370), respectively. In such examples, bearings can be used to promote the rotatability of carriage nut (130) relative to piercer retraction assembly (350). Additionally, although retainer (390) is shown as having a generally circular shape, it should be understood that in some examples retainer (390) may comprise a variety of other shapes. For instance, in other examples retainer (390) comprises a c-washer, a snap-on washer, a circlip, a Jesus clip, and/or any other suitable retaining feature as will be apparent to those of ordinary skill in the art in view of the teachings herein.

When piercer drive assembly (300) is assembled (e.g., as seen in FIG. 4), spring (302) is disposed between the proximal end of actuation member (330) and the distal end of body (354) of first retraction member (352). In addition, spring (302) is disposed coaxially around slide portion (316) of cocking member (310) and/or coaxially around slide portion (140) of carriage nut (130), depending on the particular stage of operation of drive assembly (100). As will be described in greater detail below, spring (302) is generally configured to drive actuation member (330) distally after actuation member (330) is released by release assembly (400). Spring (302) generally defines an outer diameter that approximately corresponds to the outer diameter of slide portion (316) of cocking member (310). Although spring (302) of the present example is shown as a coil spring, it should be understood that any other suitable resilient member may be used as will be apparent to those of ordinary skill in the art in view of the teachings herein.

Figure 12:
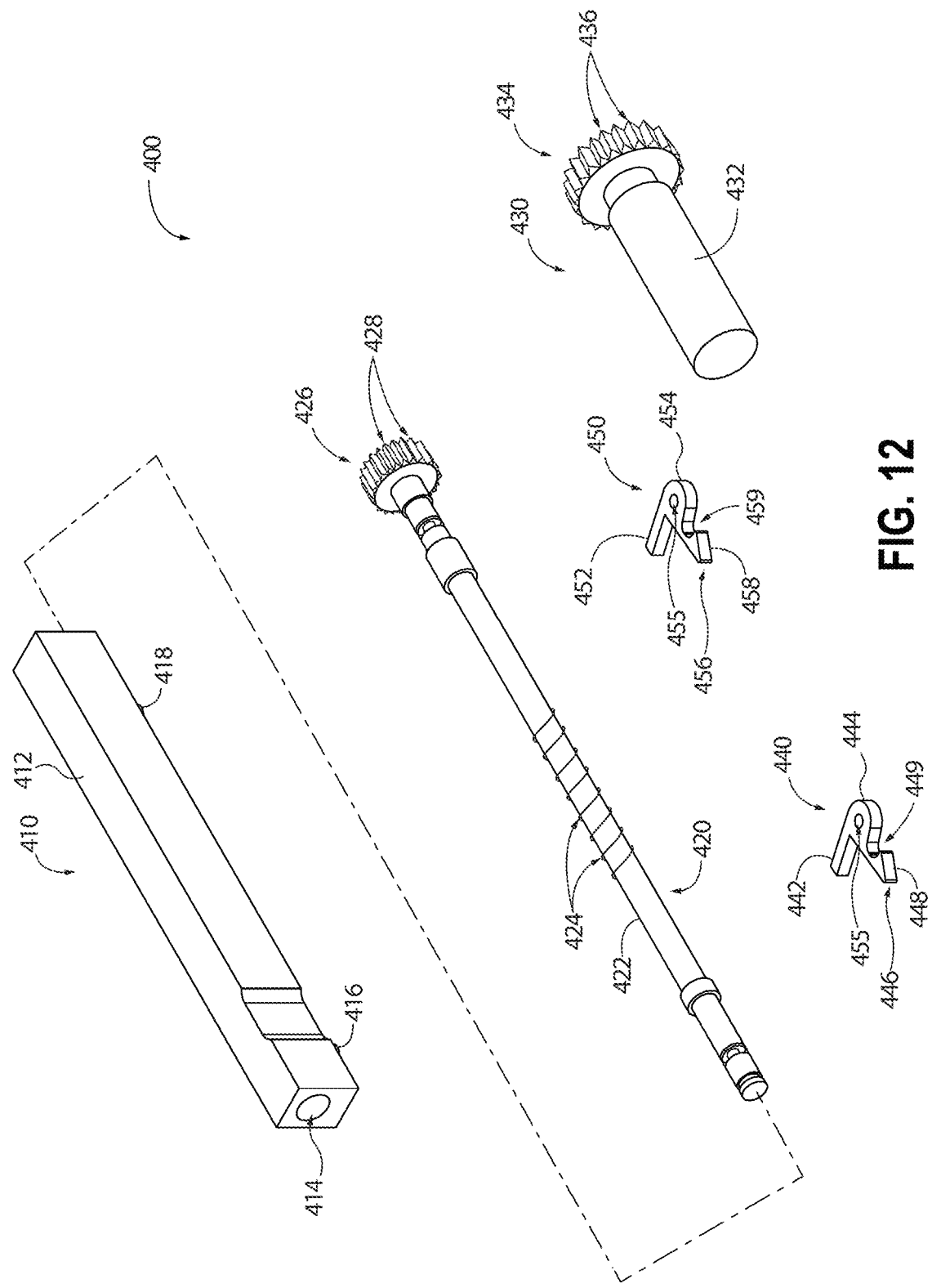
FIG. 12 depicts an exploded view of a release assembly of the drive assembly of FIG. 4.
Figure 13:
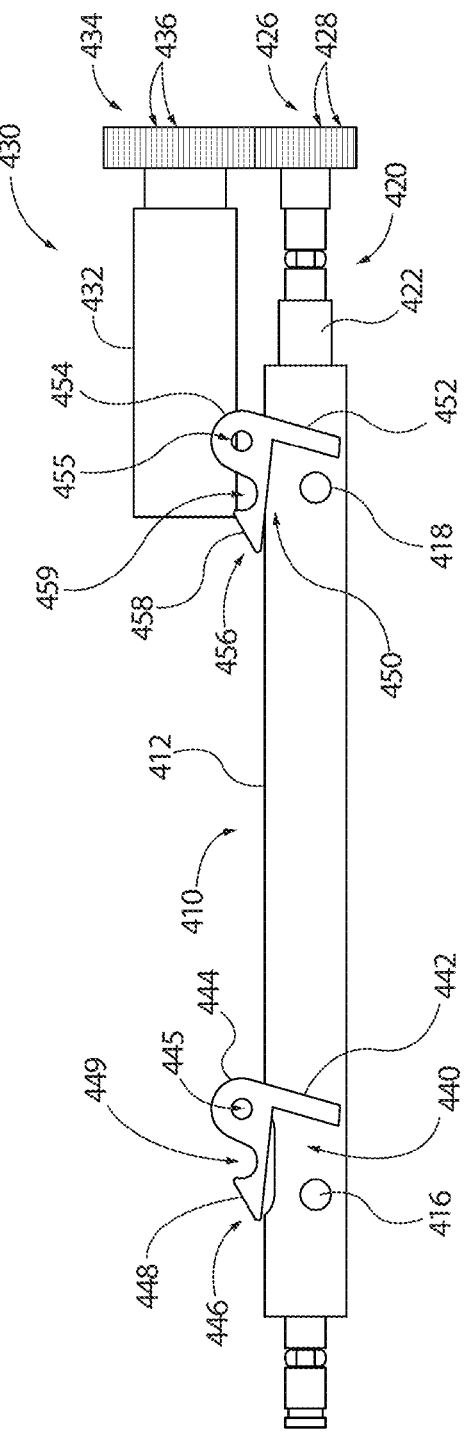
FIG. 13 depicts a bottom plan view of the release assembly of FIG. 4.

FIGS. 12 and 13 show release assembly (400) in greater detail. As can be seen, release assembly (400) comprises a nut member (410), a secondary lead screw (420), a motor assembly (430), a first latch member (440), and a second latch member (450). Nut member (410) comprises a body (412) with an elongate bore (414) extending longitudinally therethrough. Although not shown, it should be understood that within body (412), bore (414) includes a threaded portion (not shown) including threads (not shown) extending into bore (414). As will be described in greater detail below, threaded portion of bore (414) is configured to engage at least a portion of secondary lead screw (420) to permit secondary lead screw (420) to drive proximal and distal translation of nut member (410).

Nut member (410) further includes a first latch actuator (416) and a second latch actuator (418) extending downwardly from body (412). Both first latch actuator (416) and second latch actuator (418) comprise a generally cylindrical shape, although any other suitable shape may be used. First latch actuator (416) is associated with first latch member (440), while second latch actuator (418) is associated with second latch member (450). As will be described in greater detail below, latch actuators (416, 418) are generally configured to engage with a corresponding latch member (440, 450) to release cutter drive assembly (200) and piercer drive assembly (300) to fire cutter (40) and piercer (22), respectively.

Secondary lead screw (420) comprises a drive rod (422) and a drive member (426). Drive rod (422) defines a generally cylindrical shape with a plurality of threads (424) extending along at least a portion of the length of drive rod (422). Threads (424) are configured to engage corresponding threads disposed within nut member (410). This engagement between threads (424) of drive rod (422) and the threads of nut member (410) generally results in the conversion of rotation motion of secondary lead screw (420) into translation of nut member (410). As will be described in greater detail below, this motion of nut member (410) via lead screw (420) is generally configured to selectively initiate firing of cutter (40) and piercer (22).

Drive member (426) of secondary lead screw (420) is fixedly secured to the proximal end of drive rod (422). Drive member (426) is configured to impart rotary motion onto drive rod (422) from motor assembly (430). In particular, drive member (426) comprises a plurality of teeth (428). As will be described in greater detail below, teeth (428) are configured to engage at least a portion of motor assembly (430) such that rotatory motion provided by motor assembly (430) is communicated to drive rod (422) via teeth (428) of drive member (426).

Motor assembly (430) assembly comprises a rotary power source (432) and a drive member (434) in rotary communication with rotary power source (432). Rotary power source (432) in the present example is configured as an electrical motor. In other examples, rotary power source (432) can be configured as a variety of other rotary power sources such as pneumatic motors, piezoelectric motors, and/or etc.

Drive member (434) of motor assembly (430) is configured to communicate rotary power from rotary power source (432) to secondary lead screw (420). In particular, drive member (434) comprises a plurality of teeth (436) that are configured to engage with teeth (428) of drive member (426) described above with respect to secondary lead screw (420). Though engagement between teeth (428, 436), drive members (426, 434) are rotated, thereby communicating rotary power from motor (432) to drive member (426) of secondary lead screw (420). Although drive members (426, 434) are described herein as being essentially gears with teeth (428, 436), it should be understood that in other examples any other suitable rotary transmission may be used. By way of example only, suitable rotary transmissions may include a belt drive, a drive with additional gears to provide a gear ratio between motor (432) and drive rod (422), and/or etc.

First latch member (440) comprises lever portion (442), a pivot portion (444), and a catch portion (446). Lever portion (442), pivot portion (444), and catch portion (446) are all integrally connected to form L-shaped structure. Lever portion (442) and catch portion (446) each define one leg of the L-shape, pivot portion (444) is disposed between lever portion (442) and catch portion (448). Pivot portion (444) includes an opening (445) extending entirely through latch member (440) such that a pin or other similar structure may be received by opening (445) for pivoting of first latch member (440) about an axis defined by opening (445). As will be described in greater detail below, this pivoting action generally permits first latch member (440) to selectively catch and release member (238) of cutter drive assembly (200).

Catch portion (446) defines a ramp feature (448) and a recessed feature (449). Ramp feature (448) is generally triangular in shape, while adjacent recessed feature (449) is generally semicircular. Both ramp feature (448) and recessed feature (449) are configured to engage release member (238) of cutter drive assembly (200). For instance, and as will be described in greater detail below, ramp feature (448) functions to pivot first latch member (440) away from release member (238) to a receiving or releasing position so that release member (238) can enter recessed feature (449).

Similarly, recessed feature (449) catches or otherwise selectively secures release member (238) when first latch member (440) is pivoted to a cocked position. Although not shown herein, it should be understood that in some examples, first latch member (440) may include a resilient feature to resiliently bias first latch member (440) toward the cocked position once release member (238) is received by recessed feature (449).

Second latch member (450) comprises lever portion (452), a pivot portion (454), and a catch portion (456). Lever portion (452), pivot portion (454), and catch portion (456) are all integrally connected to form an L-shaped structure. Lever portion (452) and catch portion (456) each define one leg of the L-shape, pivot portion (454) is disposed between lever portion (452) and catch portion (458). Pivot portion (454) includes an opening (455) extending entirely through latch member (450) such that a pin or other similar structure may be received by opening (455) for pivoting of second latch member (450) about an axis defined by opening (455). As will be described in greater detail below, this pivoting action generally permits second latch member (450) to selectively catch and release member (338) of piercer drive assembly (300).

Catch portion (456) defines a ramp feature (458) and a recessed feature (459). Ramp feature (458) is generally triangular in shape, while adjacent recessed feature (459) is generally semicircular. Both ramp feature (458) and recessed feature (459) are configured to engage release member (338) of piercer drive assembly (300). For instance, and as will be described in greater detail below, ramp feature (458) functions to pivot second latch member (450) away from release member (338) to a receiving or releasing position so that release member (338) can enter recessed feature (459). Similarly, recessed feature (459) catches or otherwise selectively secures release member (338) when second latch member (450) is pivoted to a cocked position. Although not shown herein, it should be understood that in some examples, first latch member (450) may include a resilient feature to resiliently bias first latch member (450) toward the cocked position once release member (338) is received by recessed feature (459).

FIGS. 14-26 show an exemplary use of biopsy device (10) described above. In particular, in such a use, drive assembly (100) is generally used to cock and then fire piercer (22) and cutter (40) in a predetermined sequence to penetrate a suspicious lesion and then sever a tissue sample thereof. Once piercer (22) and cutter (40) are fired, piercer (22) is retracted relative to cutter (40) to permit collection of the severed tissue by an operator. The cocking and firing process may then be repeated as many times as desired to collect as many tissue samples as desired by the user.

Figure 14:
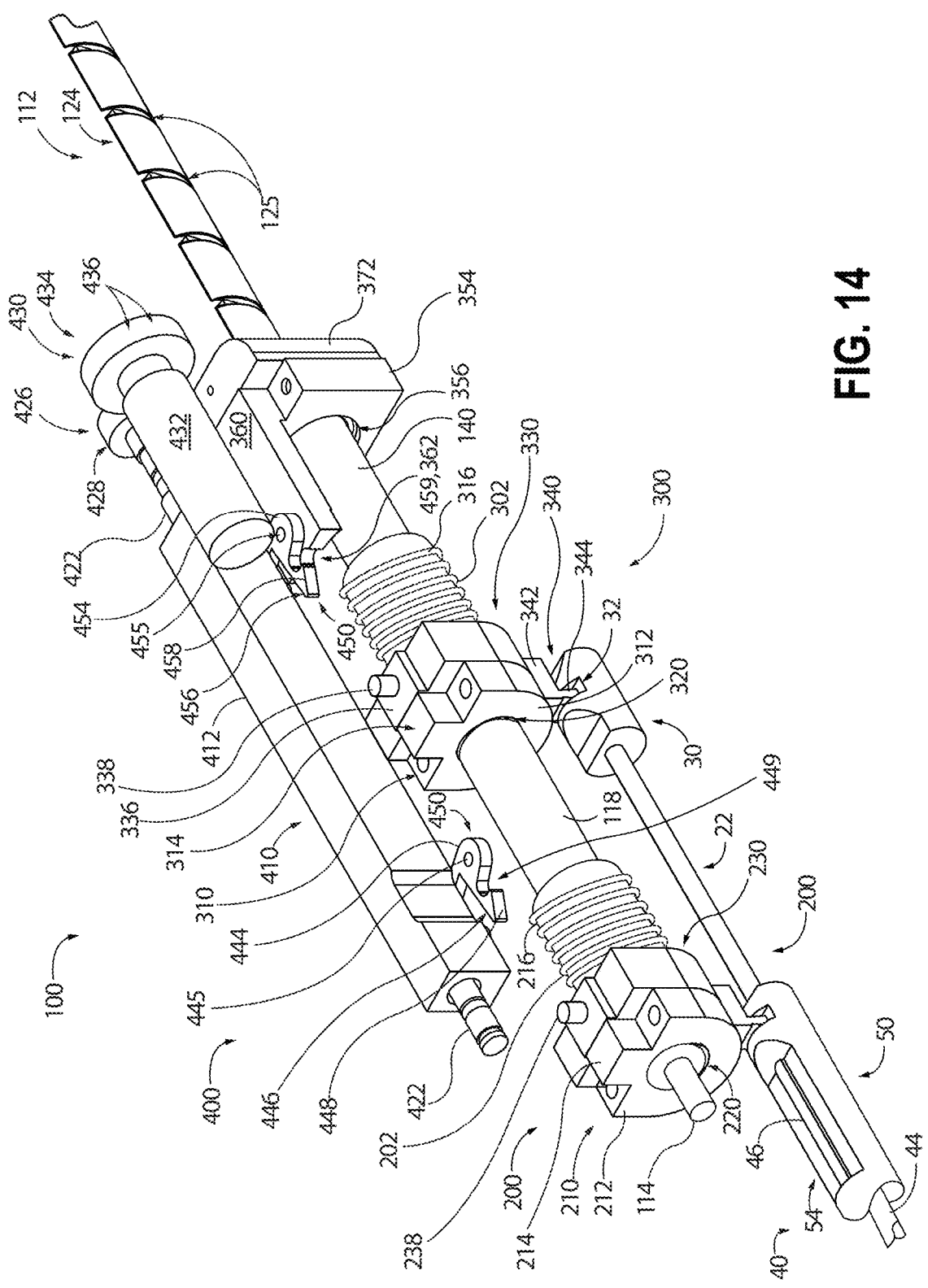
FIG. 14 depicts another perspective view of the drive assembly of FIG. 4, with the drive assembly in an initial position.
Figure 15:
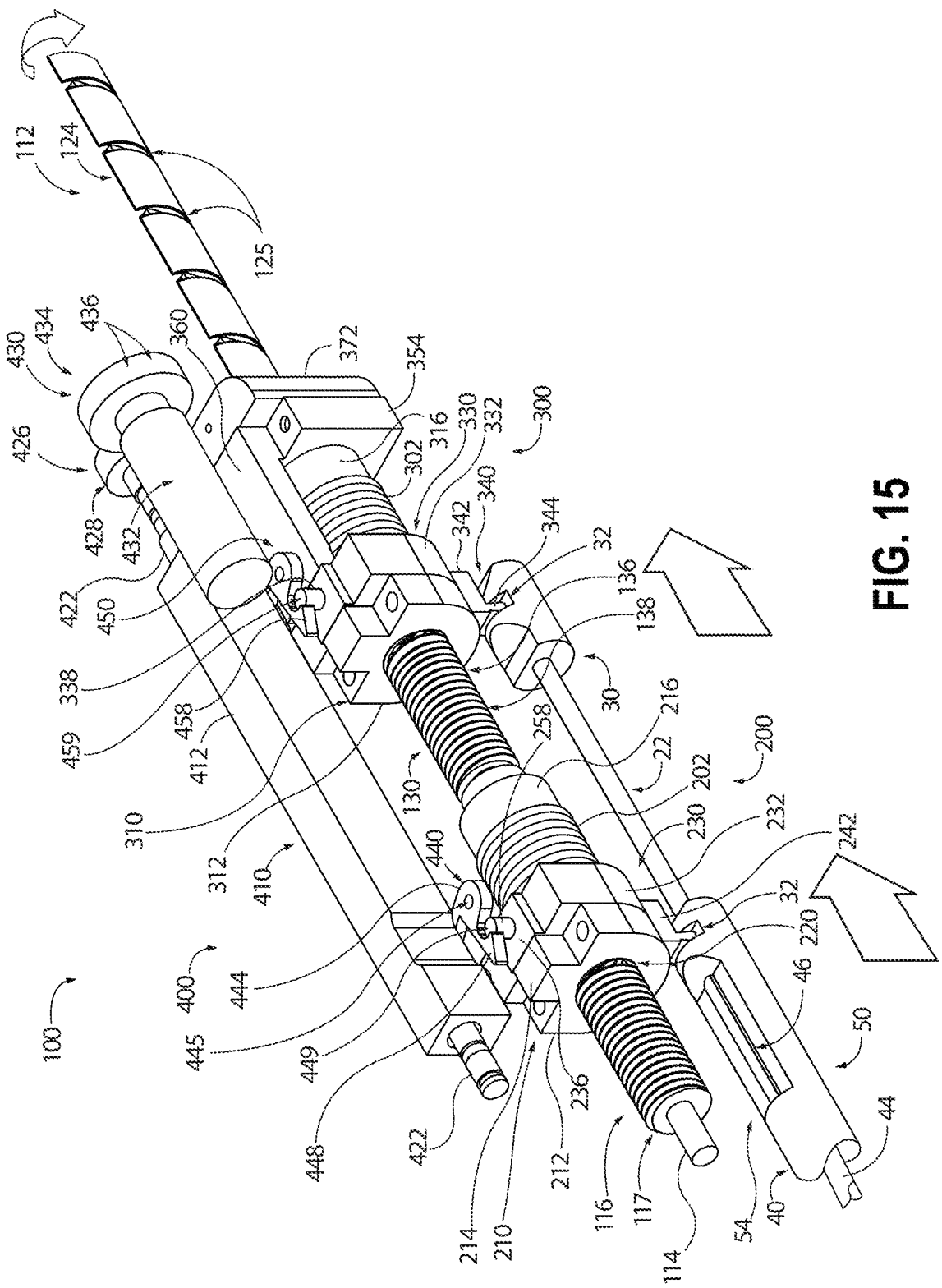
FIG. 15 depicts still another perspective view of the drive assembly of FIG. 4, with the drive assembly in a cocked position.
Figure 16:
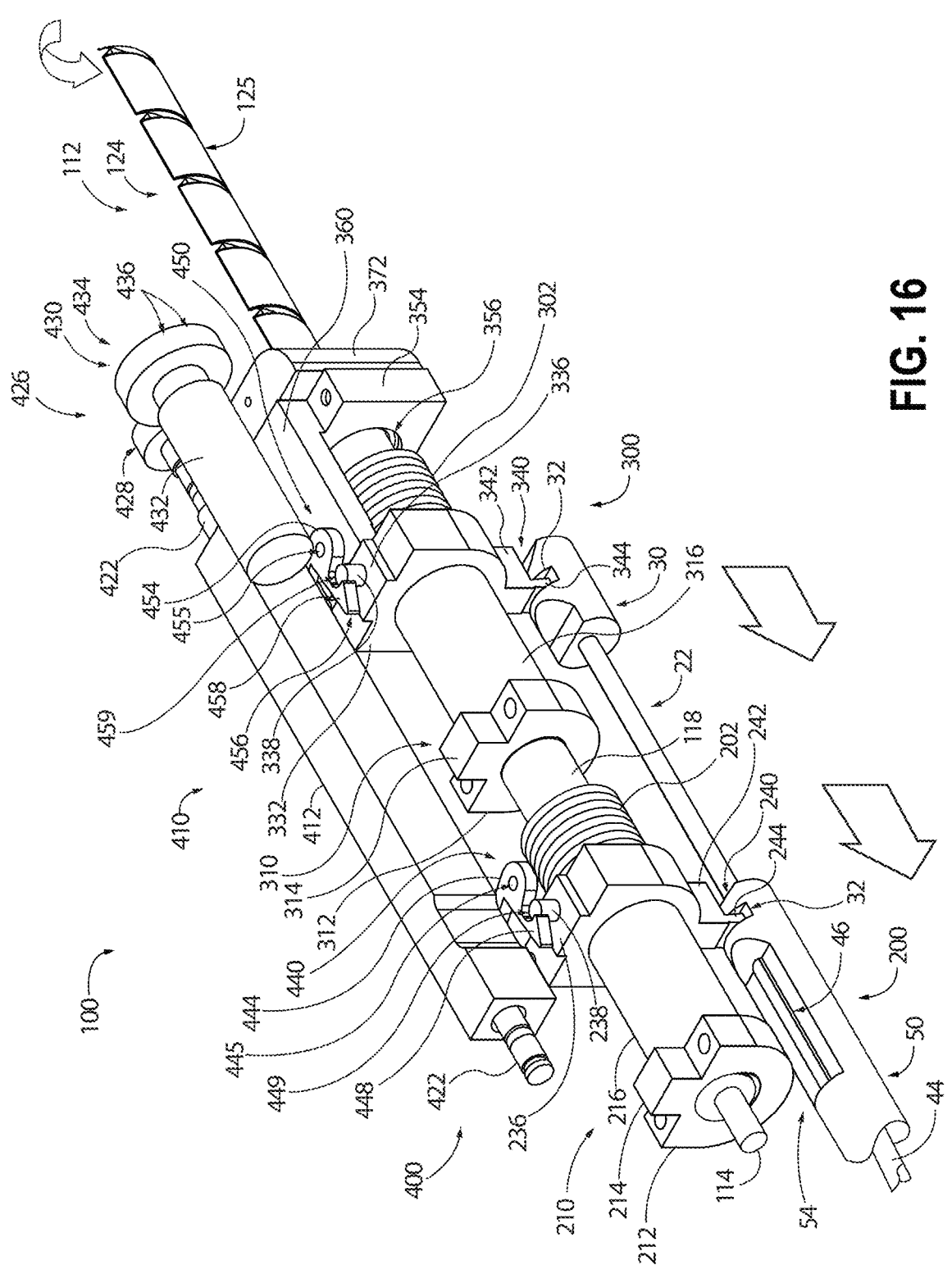
FIG. 16 depicts yet another perspective view of the drive assembly of FIG. 4, with the drive assembly in a ready position.

FIGS. 14-16 show an exemplary cocking sequence that results in piercer (22) and cutter (40) being prepared for firing. In the cocking sequence, drive assembly (100) can begin in an initial position as shown in FIG. 15. Alternatively, and as will be described in greater detail below, drive assembly (100) may begin in a cocked position as shown in FIG. 15. In the initial position, piercer (22) and cutter (40) are each in a distal position. Correspondingly, cutter drive assembly (200) and piercer drive assembly (300) are also in a distal uncocked position. Release assembly (400) is disengaged from both cutter drive assembly (200) and piercer drive assembly (300) when cutter drive assembly (200) and piercer drive assembly (300) are in the distal position.

When cutter drive assembly (200) is in the distal position, cocking member (210) is positioned on the distal end of first threaded portion (116) of lead screw (112). Actuation member (230) is positioned adjacent to stop portion (212) of cocking member (210) via spring (202). In particular, because release member (238) of actuation member (230) is disengaged from release assembly (400), release member (238) is freely movable along the axis of lead screw (112). Despite actuation member (230) being freely movable along the axis of lead screw (112), spring (202) is resiliently biased to urge actuation member (230) distally into the position shown in FIG. 14. Thus, actuation member (230) is urged adjacent to cocking member (210) by spring (202).

When piercer drive assembly (300) is in the distal position, cocking member (310) is positioned on the distal end of threaded portion (136) of carriage nut (130). Carriage nut (130) is correspondingly positioned on the distal end of second threaded portion (124) of lead screw (112) such that cocking member (310) is in the distal most position relative to both carriage nut (130) and lead screw (112). Actuation member (330) is positioned adjacent to stop portion (312) of cocking member (310) via spring (302). In particular, because release member (338) of actuation member (330) is disengaged from release assembly (400), release member (338) is freely movable along the axis of lead screw (112) and carriage nut (130). Despite actuation member (330) being freely movable along the axis of lead screw (112) and carriage nut (130), spring (302) is resiliently biased to urge actuation member (330) distally into the position shown in FIG. 14. Thus, actuation member (330) is urged adjacent to cocking member (310) by spring (302).

In the initial position, piercer retraction assembly (350) of piercer drive assembly (300) is also in a distal position. However, when piercer retraction assembly (350) is in the distal position, piercer retraction assembly (350) is generally separate from cocking member (310) and actuation member (330). As described above, piercer retraction assembly (350) is axially fixed relative to carriage nut (130) by engagement between retainer of retraction assembly (350) and annular channel (142) of carriage nut (130). Because of this, piercer retraction assembly (350) is axially fixed near the distal end of carriage nut (130) with axial movement of piercer retraction assembly (350) only resulting from axial movement of carriage nut (130).

To move drive assembly (100) into the cocked position, an operator may actuate actuation member (16) on the exterior of outer housing (14). Actuation of actuation member (16) then provides a signal to rotary power source (164) of needle cocking assembly (110). Upon receiving such a signal, rotary power source (164) begins rotating lead screw (112) via rotary communication features (152, 162) in a first direction as shown in FIG. 15.

Rotation of lead screw (112) in the first direction generally causes cutter drive assembly (200) and piercer drive assembly (300) to translate proximally. In particular, rotation of lead screw (112) causes threads (117) of first threaded portion (118) to engage threads (222) of cocking member (210). This engagement between threads (117, 222) causes cocking member (210) to translate proximally. As cocking member (210) is translated proximally, stop portion (212) of cocking member (210) engages actuation member (230) to correspondingly push actuation member (230) proximally. Actuation member (230) in turn acts on spring (202) to thereby compress spring (202).

Proximal translation of cocking member (210) and actuation member (230) continues until release member (238) contacts first latch member (440) of release assembly (410). Once such contact is made, release member (238) of actuation member (230) engages ramp feature (448) of first latch member (440) to pivot first latch member (440) outwardly (e.g., into the page of FIG. 15) as actuation member (230) is driven proximally. Proximal translation of actuation member (230) and pivoting of first latch member (440) will continue until release member (238) is adjacent to recessed feature (449) of first latch member (440).

Once release member (238) of actuation member (230) is adjacent to recessed feature (449) of first latch member (440), rotation of lead screw (112) and corresponding proximal translation of actuation member (230) via cocking member (210) will stop. At this stage, first latch member (440) will have pivoted inwardly (e.g., out of the page of FIG. 15) to capture release member (238) of actuation member (230) within recessed feature (449) of first latch member (440). Once release member (238) is captured within recessed feature (449), actuation member (230) will be generally held in the axial position shown in FIG. 15 via first latch member (440).

Rotation of lead screw (112) also rotates carriage nut (130) via key (134) of carriage nut (130) and keyway (122) of lead screw (112). Upon rotation of carriage nut (130) piercer drive assembly (300) is generally translated proximally. In particular, upon rotation of carriage nut (130), threads (138) of carriage nut (130) engage threads (322) disposed within bore (320) of cocking member (310). The engagement between threads (138, 322) causes cocking member (310) to translate proximally. As cocking member (310) is translated proximally, stop portion (312) of cocking member (310) engages actuation member (330) to correspondingly push actuation member (330) proximally. Actuation member (330) in turn acts on spring (302) to thereby compress spring (302).

Proximal translation of cocking member (310) and actuation member (330) continues until release member (338) contacts second latch member (450) of release assembly (410). Once such contact is made, release member (338) of actuation member (330) engages ramp feature (458) of second latch member (450) to pivot second latch member (450) outwardly (e.g., into the page of FIG. 15) as actuation member (330) is driven proximally. Proximal translation of actuation member (330) and pivoting of second latch member (450) will continue until release member (338) is adjacent to recessed feature (459) of second latch member (450).

Once release member (338) of actuation member (330) is adjacent to recessed feature (459) of second latch member (450), rotation of carriage nut (130) via lead screw (112) and corresponding proximal translation of actuation member (330) via cocking member (310) will stop. At this stage, second latch member (450) will have pivoted inwardly (e.g., out of the page of FIG. 15) to capture release member (338) of actuation member (330) within recessed feature (459) of second latch member (450). Once release member (338) is captured within recessed feature (459), actuation member (330) will be generally held in the axial position shown in FIG. 15 via second latch member (450).

Once both cutter drive assembly (200) and piercer drive assembly (300) are translated to the proximal positions shown in FIG. 15, drive assembly (100) is in a cocked position. Although drive assembly (100) is shown and described herein as initially transitioning to the cocked position from the initial position, it should be understood that in some examples the procedure may begin with drive assembly (100) being in the cocked position. Regardless, in the cocked position, springs (202, 302) are compressed for firing. However, because each cocking member (210, 310) is adjacent to each actuation member (230, 330), cutter (40) and piercer (22) cannot be fired. Thus, it should be understood that when drive assembly (100) is in the cocked position, cutter (40) and piercer (22) are merely in position for firing, but drive assembly (100) is not yet fully armed.

Figures 19, 20:
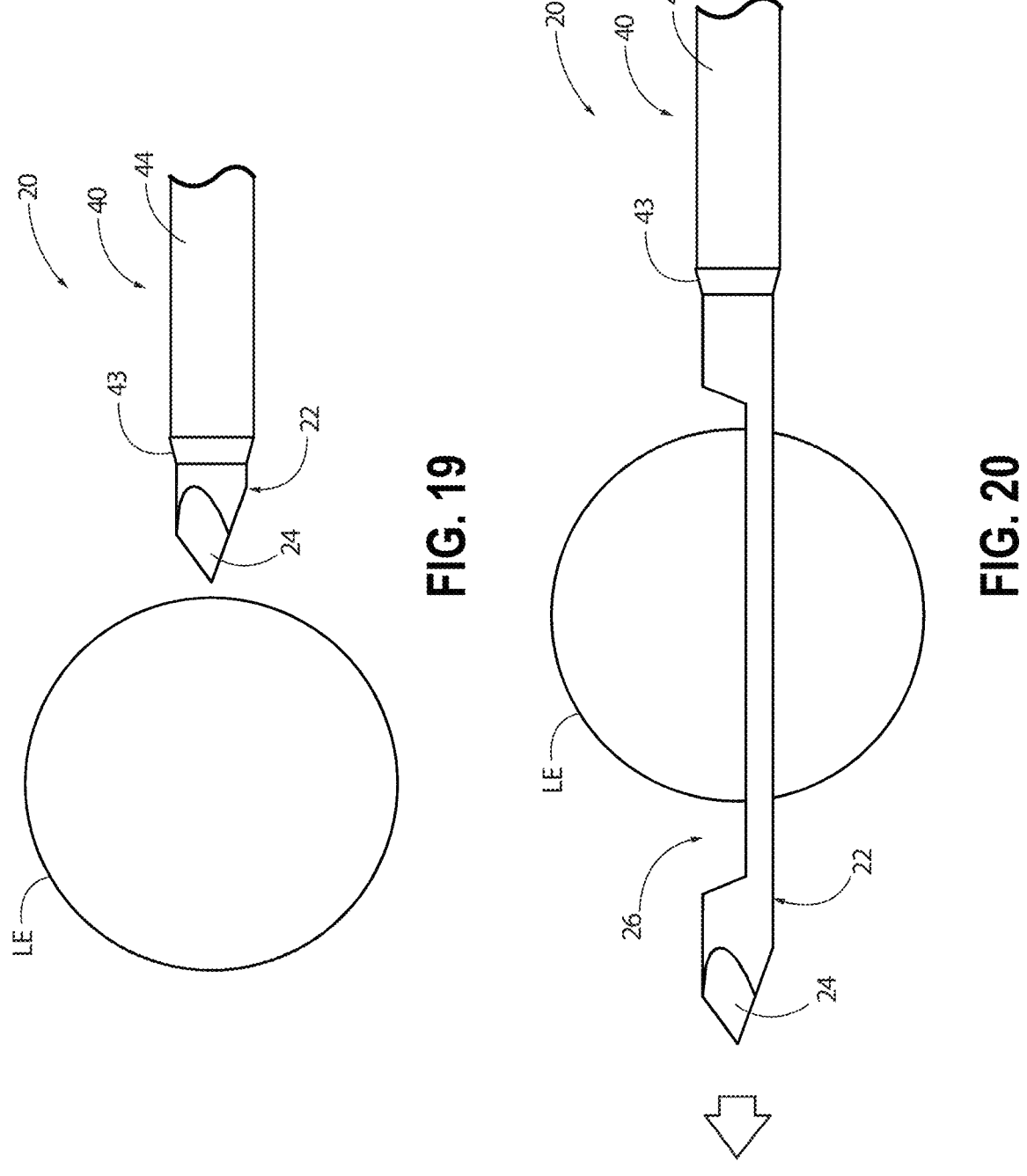
FIG. 19 depicts a partial front elevational view of the needle assembly of FIG. 2, with the needle assembly positioned adjacent to a lesion.
FIG. 20 depicts another partial front elevational view of the needle assembly of FIG. 2, with a piercer fired through the lesion.

While drive assembly (100) is in the cocked position, an operator may inert needle assembly (20) into tissue of a patient. As shown in FIG. 19, insertion may be performed to position needle assembly (20) adjacent to a suspicious lesion (LE). In some uses, inserting needle assembly (20) into tissue of a patient may be desirable to prevent inadvertent firing of piercer (22) or cutter (40). Of course, it should be understood that an operator may position needle assembly (20) when drive assembly (100) is in other positions, as will be described in greater detail below.

To prepare needle assembly (20) for firing, an operator may transition drive assembly (100) from the cocked position shown in FIG. 15 to a ready position shown in FIG. 16. To initiate the transition of drive assembly (100) from the cocked position to the ready position, an operator may push actuation member (16) a second time. Pressing actuation member (16) once again sends a signal to rotary power source (164) of needle cocking assembly (110) to initiate rotation of lead screw (112) in a second direction, opposite of the first direction.

Rotation of lead screw (112) in the opposite direction generally causes cocking member (210) of cutter drive assembly (200) and cocking member (310) of piercer drive assembly (300) to each translate distally relative to lead screw (112). In particular, threads (117) of first threaded portion (116) again engage threads (222) of cocking member (210). However, due to rotation of lead screw (112) in the second direction, this engagement causes cocking member (210) to translate distally. Because actuation member (230) and spring (202) are not fixedly secured to cocking member (210), actuation member (230) and spring (202) remain held in position by first latch member (440) of release assembly (400). Translation of cocking member (210) continues until cocking member (210) reaches the distal end of first threaded portion (116) of lead screw (112) as shown in FIG. 16.

Similarly, with respect to piercer drive assembly (300), threads (138) of carriage nut (130) again engage threads (322) of cocking member (310). As described above, rotation of lead screw (112) results in rotation of carriage nut (130) via engagement between key (134) and keyway (122). Accordingly, rotation of lead screw (112) causes carriage nut (130) to rotate in the second direction. Rotation of carriage nut (130) in the second direction causes cocking member (310) to translate distally via engagement of threads (138, 322). Because actuation member (330) and spring (302) are not fixedly secured to cocking member (310), actuation member (330) and spring (302) remain held in position by second latch member (450) of release assembly (400). Translation of cocking member (310) continues until cocking member (310) reaches the distal end of threaded portion (136) of carriage nut (130) as shown in FIG. 16.

Once cocking member (210) of cutter drive assembly (200) and cocking member (310) of piercer drive assembly (300) are positioned in the distal position as shown in FIG. 16, drive assembly (100) is in the ready position. Once drive assembly (100) is in the ready position, an operator may position needle assembly (20) into tissue of a patient adjacent to suspicious lesion (LE) as shown in FIG. 19, if operator had not already done so prior to transitioning drive assembly (100) from the cocking position to the ready position.

With drive assembly (100) in the ready position (FIG. 16), and needle assembly (20) placed near a suspicious lesion (SE) (FIG. 19), an operator may next initiate a firing sequence. FIGS. 17-18, and 19-21 show the firing sequence in greater detail. To initiate the firing sequence, an operator may press actuation member (16) on outer housing (14) a third time. When actuation member (16) is pressed, a signal now sent to motor (432) of release assembly (400). This signal causes motor (432) to supply rotary power to secondary lead screw (420) via drive members (426, 434) to thereby rotate secondary lead screw (420). As secondary lead screw (420) rotates, threads (424) of secondary lead screw (420) engage the threads disposed within body (412) of nut member (410).

Engagement between threads (424) of secondary lead screw (420) and the threads of nut member (410) during rotation of secondary lead screw (420) causes nut member (410) to retract proximally. As nut member (410) retracts proximally, second latch actuator (418) first comes into contact with lever portion (452) of second latch member (450). Due to the spacing between first latch actuator (416) and second latch actuator (418), it should be understood that only second latch actuator (418) contacts second latch member (450) initially. As will be described in greater detail below, further proximal actuation of nut member (410) is needed for first latch actuator (416) to engage lever portion (442) of first latch member (440).

Figure 17:
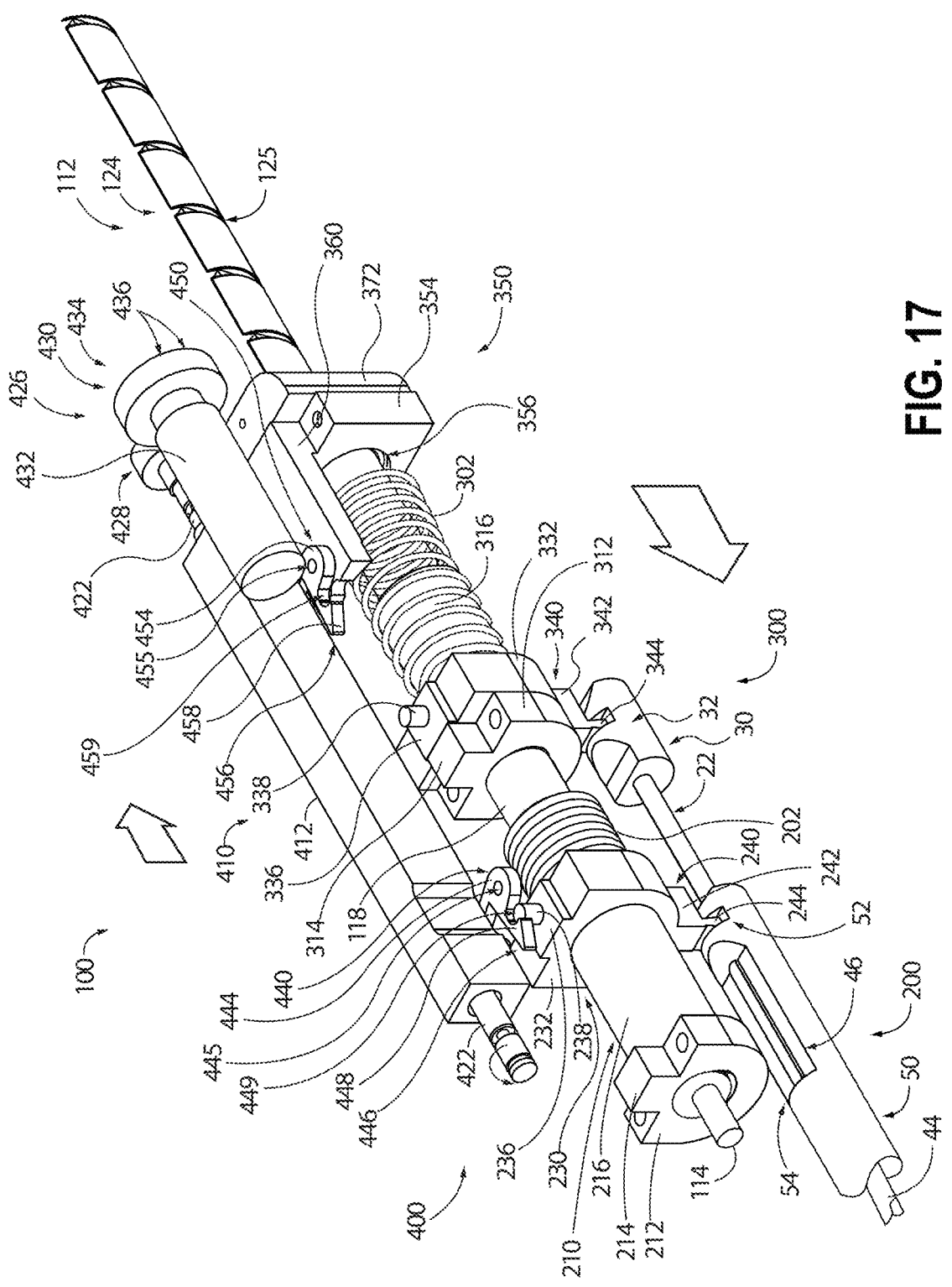
FIG. 17 depicts yet another perspective view of the drive assembly of FIG. 4, with the piercer drive assembly in a fired position.

As nut member (410) continues to translate proximally, second latch actuator (418) engages lever portion (452) of second latch member (450) to begin to pivot second latch member (450) away from release member (338) of piercer drive assembly (300). Further proximal translation of nut member (410) eventually results in second latch member (450) fully pivoting to disengage release member (338) from recessed feature (459) of second latch member (450) as shown in FIG. 17.

Once release member (338) is disengaged from recessed feature (459) of second latch member (450), actuation member (330) is free to translate axially relative to lead screw (112). Because spring (302) was previously compressed during cocking, spring (302) will now rapidly urge actuation member (330) distally. As described above, actuation member (330) includes actuation tab (340), which is secured to receiving feature (32) of piercer (22). Thus, it should be understood that rapid translation of actuation member (330) will result in corresponding rapid translation of piercer (22). Rapid translation of piercer (22) will result in distal tip (24) and notch (26) of piercer (22) penetrating through suspicious lesion (LE) as shown in FIG. 20.

Once firing of piercer (22) has occurred, motor (432) of release assembly (400) will stop, thereby stopping further proximal movement of nut member (410) via secondary lead screw (420). In the present use, proximal translation of nut member (410) will stop prior to first latch actuator (416) reaching first latch member (440) for firing of cutter (40). In other words, after piercer (22) is fired, the firing sequence is paused prior to firing cutter (40). Alternatively, in some uses, motor (432) may continue rotating without stopping after firing of piercer (22). In these uses, piercer (22) is fired first, followed by a relatively short delay, and then cutter (40) is fired using the sequence described below.

Figure 18:
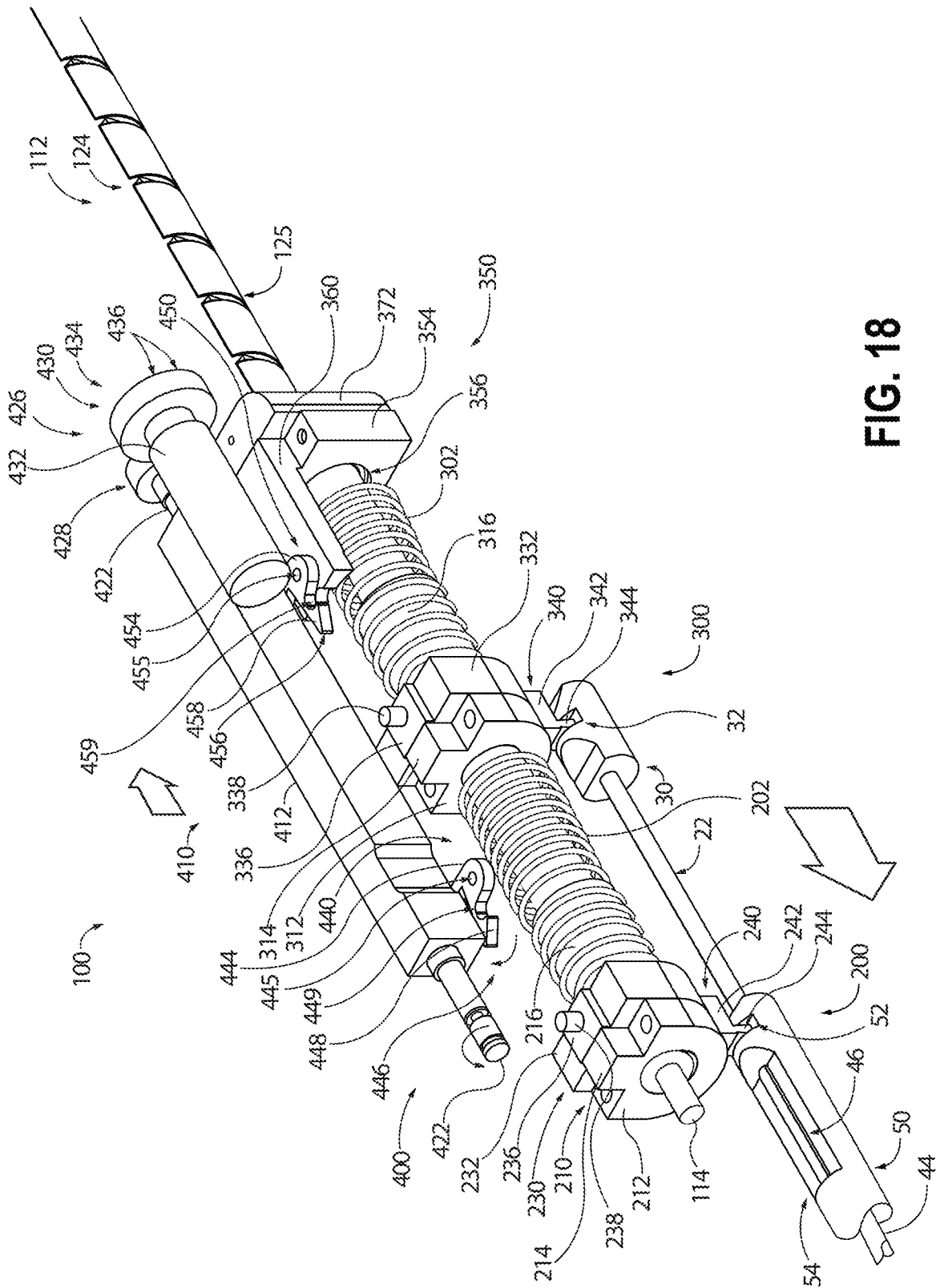
FIG. 18 depicts yet another perspective view of the drive assembly of FIG. 4, with the cutter drive assembly in a fired position.

To fire cutter (40) under the present use, an operator may reinitiate rotation of motor (432) and corresponding proximal translation of nut member (410) by pressing actuation member (16) on outer housing (14) a fourth time. This causes motor (432) of release assembly (400) to continue rotation of secondary lead screw (420). As similarly described above, engagement between threads (424) of secondary lead screw (420) and the threads of nut member (410) during rotation of secondary lead screw (420) causes nut member (410) to retract proximally. As nut member (410) continues to retract proximally first latch actuator (416) will engage lever portion (442) of first latch member (440). Further proximal translation of nut member (410) will result in first latch actuator (416) pushing lever portion (442) to pivot first latch member (440) away from release member (238) of actuation member (230) as shown in FIG. 18. This pivoting of first latch member (440) will eventually result in disengagement of release member (238) of actuation member (230) from first latch member (440).

Figure 21:
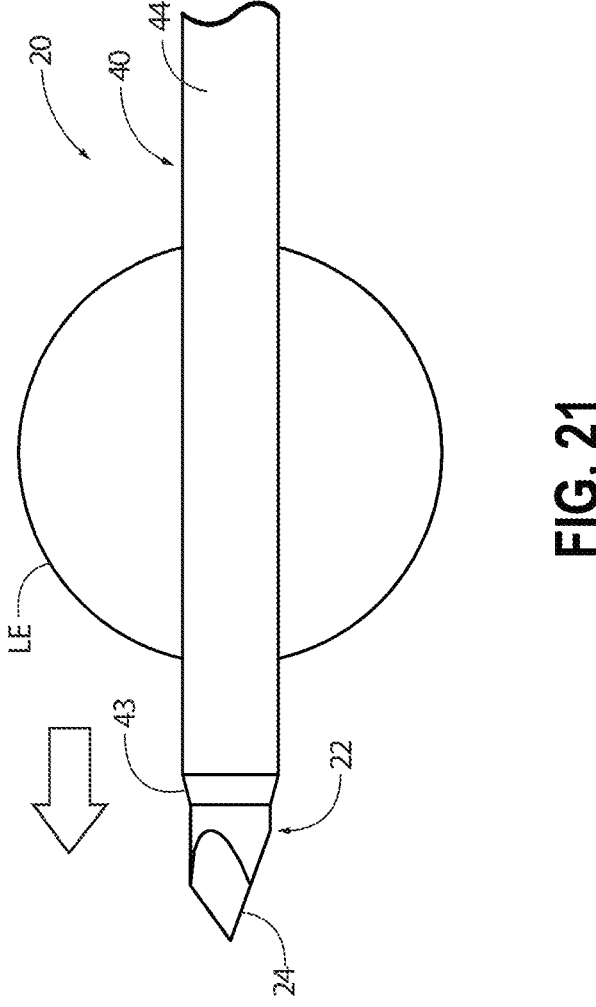
FIG. 21 depicts still another partial front elevational view of the needle assembly of FIG. 2, with a cutter fired through the lesion.

With release member (238) of actuation member (230) disengaged from first latch member (440), actuation member (230) is free to translate axially relative to lead screw (112). Because spring (202) was previously compressed during cocking, spring (202) will now rapidly urge actuation member (230) distally. As described above, actuation member (230) includes actuation tab (240), which is secured to receiving feature (52) of cutter (40). Thus, it should be understood that rapid translation of actuation member (230) will result in corresponding rapid translation of cutter (40). Rapid translation of cutter (40) will result in distal end (42) of cutter (40) penetrating through suspicious lesion (LE) as shown in FIG. 21 to sever a tissue sample into notch (26) of piercer (22).

FIGS. 22-25 show an exemplary sequence for retracting piercer (22) relative to cutter (40) to collect a tissue sample after the tissue sample has been acquired using the firing sequence described above. As will be described in greater detail below, the piercer (22) retraction sequence generally involves retracting piercer (22) relative to cutter (40) to expose notch (26) of piercer within the tissue collection feature (54) of cutter (40). When piercer (22) is retracted in this way, an operator may extract a tissue sample from notch (26) for further analysis and processing.

Figure 24:
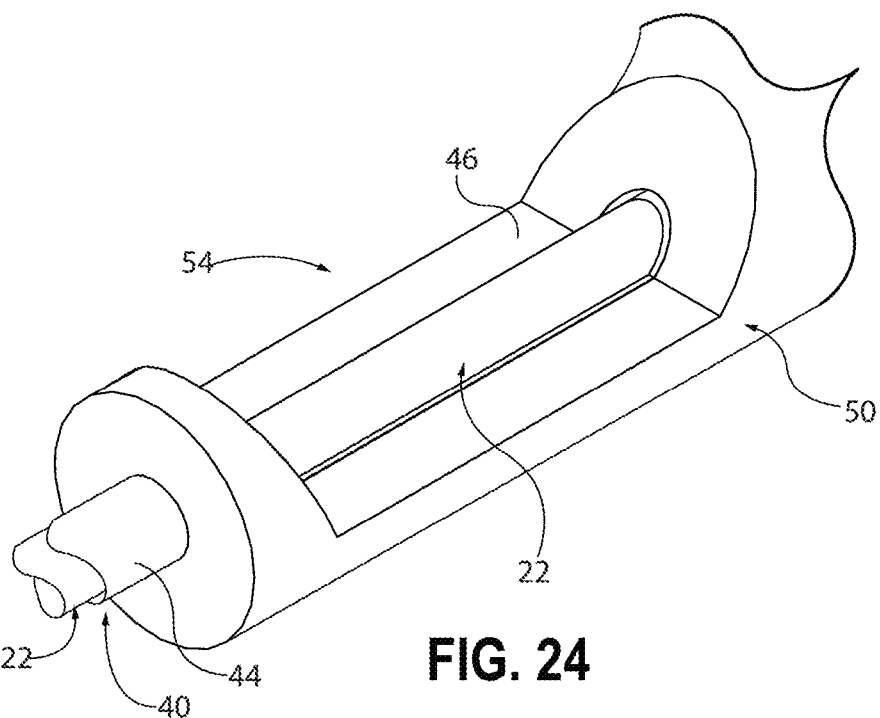
FIG. 24 depicts a detailed perspective view of a tissue collection feature of the needle assembly of FIG. 2, the tissue collection feature in a closed position.

The piercer (22) retraction sequence begins by returning drive assembly (100) to the cocked position described above with respect to FIG. 15. When drive assembly (100) is in the cocked position shown in FIGS. 4 and 15, piercer (22) is correspondingly disposed in a distal position. As can be seen in FIG. 24, when piercer is in the distal position, tissue collection feature (54) of cutter (40) is generally blocked by piercer (22). To return drive assembly (100) to the cocked position, an operator may press actuation member (16) on outer housing (14) a fifth time. As described above, drive assembly (100) is generally transitioned to the cocked position by rotating lead screw (112) in the first direction to translate cocking members (210, 310) of cutter drive assembly (200) and piercer drive assembly (300) proximally relative to lead screw (112).

Once drive assembly (100) is returned to the cocked position as shown in FIGS. 4 and 15, lead screw (112) continues to rotate in the first direction. As rotation continues, cocking members (210, 310) of cutter drive assembly (200) and piercer drive assembly (300) will begin to free-wheel relative to lead screw (112). In particular, cocking member (210) of cutter drive assembly (200) will disengage from first threaded portion (116) of lead screw (112) as cocking member (210) transitions to being adjacent to indented portion (119) of lead screw (112). Similarly, cocking member (310) of cutter drive assembly (300) will disengage from threaded portion (136) of carriage nut (130) as cocking member (310) transitions to being adjacent to indented portion (144) of carriage nut (130).

Figure 22:
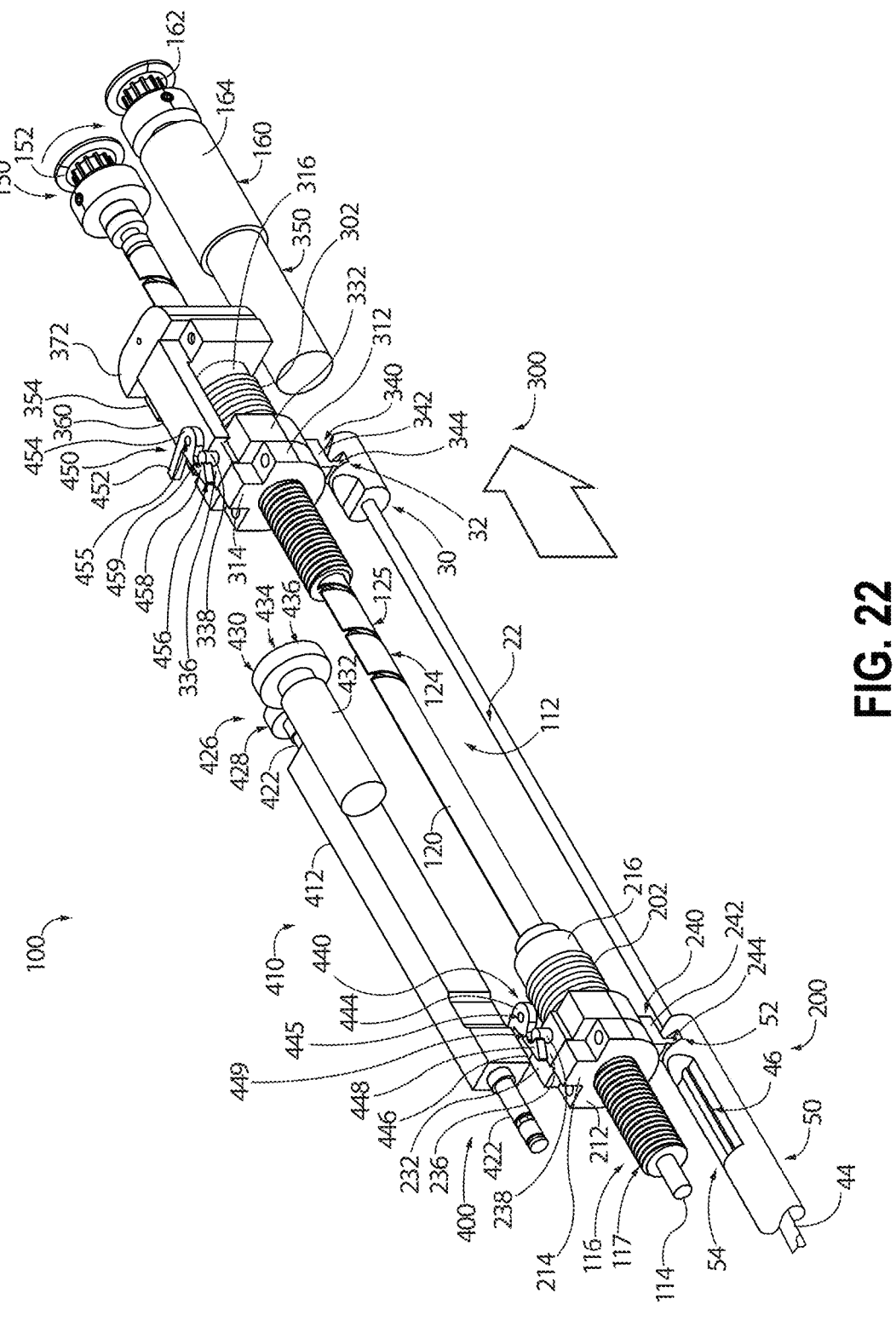
FIG. 22 depicts yet another perspective view of the drive assembly of FIG. 4, with a piercer retraction assembly retracted to an intermediate position.

As cocking members (210, 310) begin to free-wheel as described above, piercer retraction assembly (350) will begin to engage second threaded portion (124) of lead screw (112). In particular, protrusion (378) of second retraction member (370) is received by threads (125) of second threaded portion (124). As lead screw (112) rotates, engagement between protrusion (378) and threads (125) pulls second retraction member (370) proximally as shown in FIG. 22. Because second retraction member (370) is secured to first retraction member (352), proximal movement of second retraction member (370) also pulls first retraction member (352) proximally. Additionally, because retainer (390) is positioned between first retraction member (352) and second retraction member (370) to axially secure carriage nut (130) to piercer retraction assembly (350), proximal movement of first retraction member (352) and second retraction member (370) will result in corresponding proximal movement of carriage nut (130). With piercer drive assembly (300) disposed on carriage nut (130), translation of carriage nut (130) also results in translation of piercer drive assembly (300). Thus, it should be understood that as piercer retraction assembly (350) is driven proximally by rotation of lead screw (112), corresponding translation of piercer drive assembly (300) along with piercer (22) will result.

Figure 23:
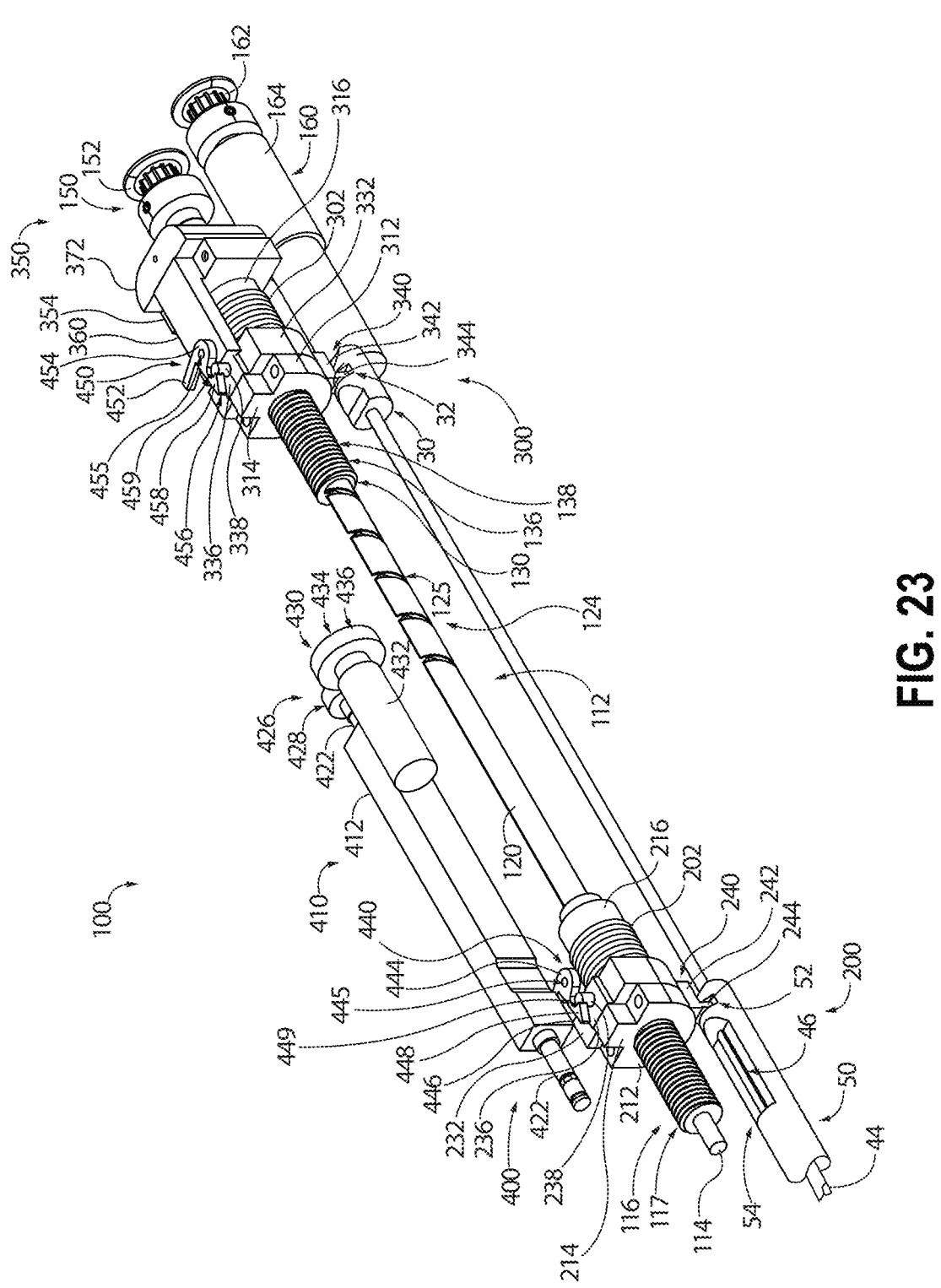
FIG. 23 depicts yet another perspective view of the drive assembly of FIG. 4, with the piercer retraction assembly of FIG. 22 retracted to a proximal position.

Proximal translation of piercer retraction assembly (350), piercer drive assembly (300), and piercer (22) continues until piercer retraction assembly (350) reaches the distal position shown in FIG. 23. Once piercer retraction assembly (350) reaches the distal position, rotation of lead screw (112) stops, thereby stopping further proximal translation of piercer retraction assembly (350).

Figure 25:
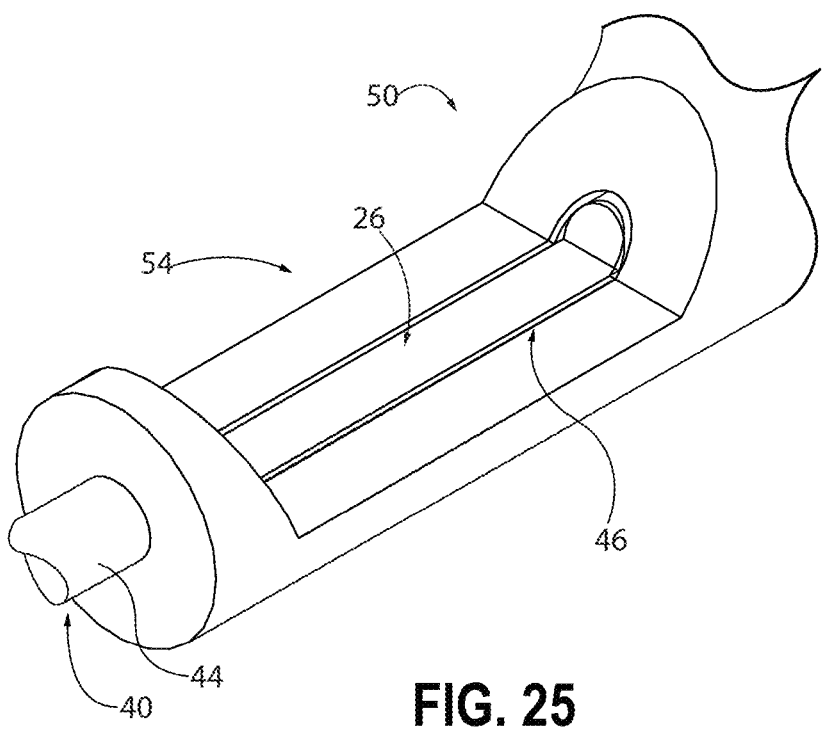
FIG. 25 depicts another detailed perspective view of the tissue collection feature of the needle assembly of FIG. 2, the tissue collection feature in an open position.

When piercer drive assembly (300) is in the distal position, piercer (22) is also in a distal position as shown in FIG. 25. As can be seen in FIG. 25, when piercer (22) is in the distal position, notch (26) of piercer (22) is aligned with tissue collection feature (54) of cutter (40). This alignment provides access to notch (26) through cut out (46) in cutter (40). At this stage, an operator may collect a tissue sample from notch (26) for further examination, analysis, investigation, and/or etc.

After having acquired a tissue sample, an operator may complete the biopsy procedure by removing biopsy device (10) from the patient. Alternatively, in some instances an operator may desire to collect additional samples using a single insertion of needle assembly (20) into a patient. In such instances, an operator may press actuation member (16) on outer housing (14) a sixth time. This will cause rotation communication feature (162) of needle cocking assembly to reactivate and return drive assembly (100) to the initial position or the cocking position via rotation of lead screw (112). An operator may then follow the same procedure described above one or more times until a desired number of tissue samples are collected.

II. EXAMPLE OF ALTERNATIVE DRIVE ASSEMBLY FOR CORE NEEDLE BIOPSY DEVICE

In some versions of biopsy device (10) described above, it may be desirable for structures similar to body (12) to have a compact size. For instance, one desirable aspect of core needle biopsy devices in contrast to vacuum assisted biopsy devices is the compact size of core needle biopsy devices relative to vacuum assisted biopsy devices.

In some circumstances, compact size may be a function of the internal components of the particular device and the functionality of the device. For instance, in some core needle biopsy devices (10) movement of structures similar to piercer (22) and/or cutter (40) may be facilitated by a spring-loaded mechanism. Such movement may be limited to a predetermined sequence of piercer (22) and cutter (40)

together and relative to each other. Thus, such spring-loaded mechanisms may be relatively compact to facilitate such movement. By contrast, vacuum assisted biopsy devices may utilize more complex movements of structures similar to cutter (40), which may result in relatively complex drive mechanisms. Such relatively complex drive mechanisms may thus occupy a greater footprint making some vacuum assisted biopsy devices less compact relative to some core needle biopsy devices.

In some circumstances, operators may prefer relatively compact biopsy devices. For instance, in ultrasound guided procedures, a compact biopsy device may be preferable because manipulation of the biopsy device may be performed using a single hand. In other circumstances, a compact biopsy device may be desirable to promote ease of use even when manipulation may not be performed entirely by hand. For instance, in some stereotactic or MRI guided procedures, space near the patient may be limited due to other accessory components such as patient tables, imaging equipment, fixtures, etc. A biopsy device of compact size may thus be desirable in a variety of circumstances.

As described above, biopsy device (10) may also be desirable to provide characteristics of a core needle biopsy device, but with the functionality of collecting multiple samples in a single insertion. However, one aspect of such functionality is that in some versions, structures similar to piercer (22) may retract the length of structures similar to cutter (40) for collection of each tissue sample. Such piercer (22) retraction may be accomplished by a variety of mechanisms, but when combined with the functions of cocking and firing, such mechanisms may increase in size. Thus, in some versions of biopsy device (10), it may be desirable to incorporate a drive assembly similar to drive assembly (100) with the functionalities of cocking, firing, and piercer retraction, but with a relatively compact size.

Figure 26:
FIG. 26 depicts a perspective view of an alternative drive assembly that may be incorporated into the core needle biopsy device of FIG. 1.
Figure 27:
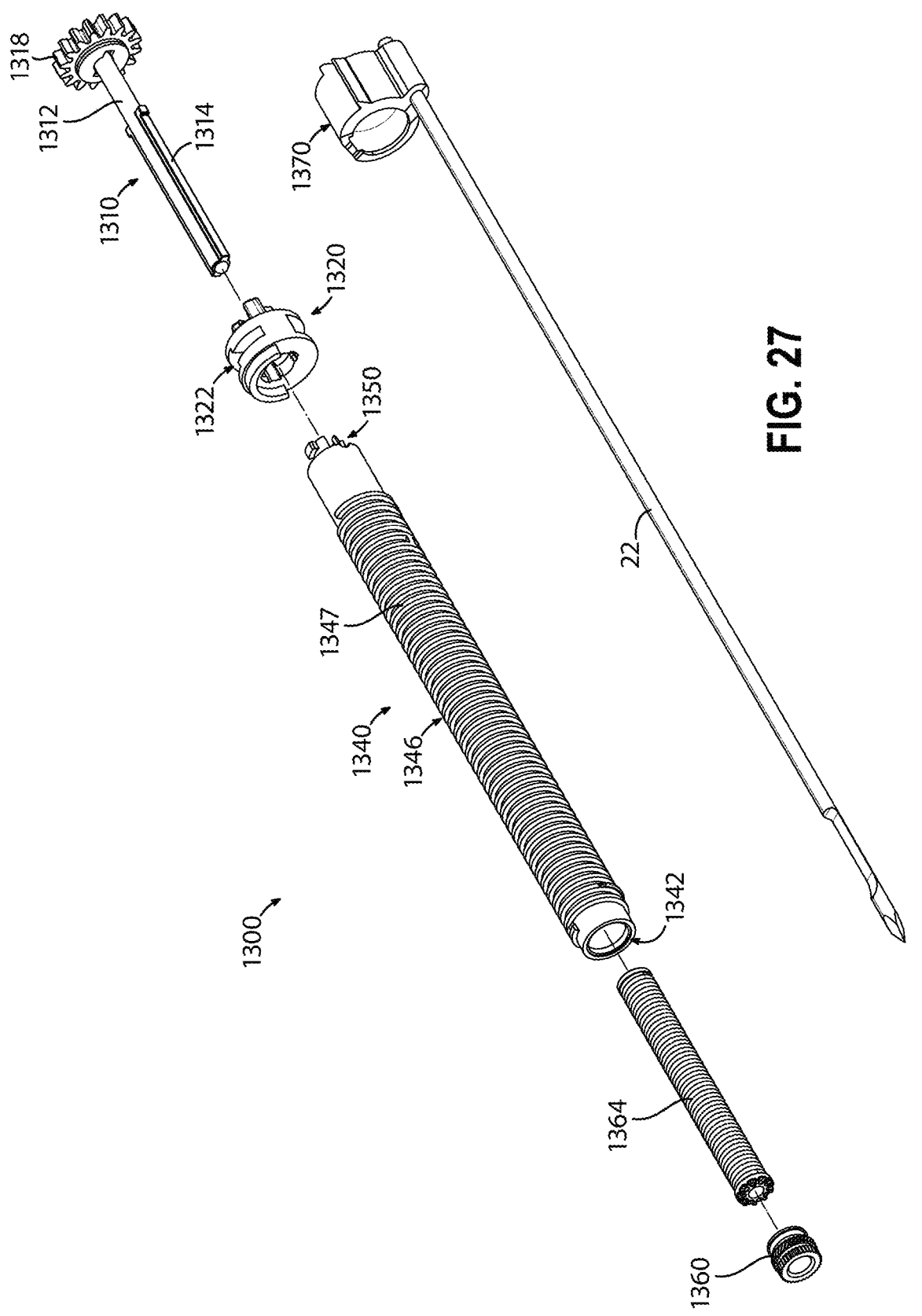
FIG. 27 depicts an exploded perspective view of a piercer drive assembly of the drive assembly of FIG. 26.

FIGS. 26 and 27 show an example of an alternative drive assembly (1100) that may be incorporated into biopsy device (10) in lieu of drive assembly (100) described above. As with drive assembly (100) described above, drive assembly of the present version is generally configured to drive piercer (22) and cutter (40) through a predetermined sequence for cocking, firing, and sample collection. Like drive assembly (100) described above, drive assembly (1100) of the present example includes a piercer drive assembly (1300) and a cutter drive assembly (1200). As will be described in greater detail below, piercer drive assembly (1300) and cutter drive assembly (1200) are generally interconnected to interact with each other to generally reduce the overall size of drive assembly (1100).

Piercer drive assembly (1300) may be in communication with piercer (22) such that piercer drive assembly (1300) may be configured to drive piercer (22) through a predetermined sequence of movement independently from cutter (40), in concert with cutter (40), or both. Additionally, as will be described in greater detail below, piercer drive assembly (1300) may be in communication with one or more elements of cutter drive assembly (1200) to drive elements of cutter drive assembly (1200) and/or cutter (40). As best seen in FIG. 27, piercer drive assembly (1300) includes a lead screw drive shaft (1310), a lead screw latch (1320), an outer lead screw (1340) (also referred to as primary lead screw, dual-thread lead screw, or driver), and a piercer carriage (1370). Generally, piercer drive assembly (1300) is configured to move piercer (22) via piercer carriage (1370) by moving piercer carriage (1370) directly via rotation of outer lead screw (1340) or indirectly via translation of outer lead screw (1340).

Figure 28:
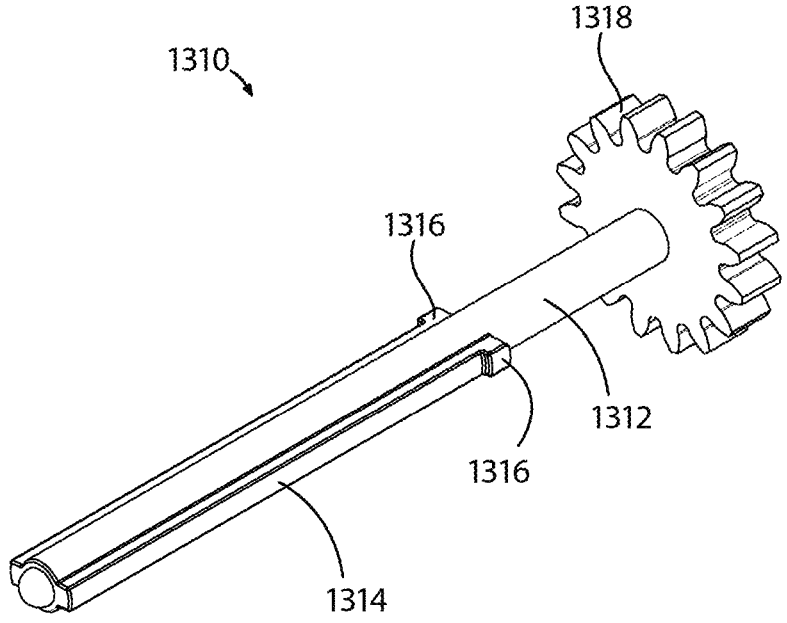
FIG. 28 depicts a perspective view of a lead screw drive shaft of the piercer drive assembly of FIG. 27.

Lead screw drive shaft (1310) is generally configured to drive rotation of outer lead screw (1340), while also permitting at least some translation of outer lead screw (1340) relative to lead screw drive shaft (1310) in some circumstances. As best seen in FIG. 28, lead screw drive shaft (1310) includes a shaft (1312) having a keyed portion (1314), and a drive gear (1318). Shaft (1312) is generally configured to be slidably received within a portion of outer lead screw (1340) to drive rotation of outer lead screw (1340) via keyed portion (1314). Drive gear (1318) is thus fastened to shaft (1312) or integral therewith to drive rotation of shaft (1312), which may drive rotation of outer lead screw (1340). Although not shown, it should be understood that drive gear (1314) may mesh with other components of biopsy device (10) such as a motorized assembly to drive rotation of shaft (1312).

Keyed portion (1314) of the present version includes a pair of outwardly extending elongate protrusions or wings. Specifically, each protrusion or wing defines a rectangular cross-section that extends along that axial length of shaft (1312). As will be described in greater detail below, keyed portion (1314) is generally configured to be received within a complementary portion of outer lead screw (1340) to transfer rotation from shaft (1312) to outer lead screw (1340). Additionally, as will also be described in greater detail below, the elongate nature of keyed portion (1314) is generally configured to permit some axial movement of outer lead screw (1340) relative to shaft (1312), while still permitting the transfer of rotation from shaft (1312) to outer lead screw (1340). Thus, it should be understood that in other versions, various alternative configurations of keyed portion (1314) may be used. For instance, in some versions, keyed portion (1314) may include a hexagonal feature, an octagonal feature, an oval feature, a single key, etc.

Shaft (1312) further includes one or more buttress features (1316) extending outwardly from keyed portion (1314). Each buttress feature (1316) is generally configured to engage a portion of lead screw latch (1320) to provide additional surface area at the point of engagement between shaft (1312) and lead screw latch (1320). As will be described in greater detail below, such engagement may be used in some versions to releasably hold relatively large spring forces. Thus, the additional material and surface area provided by each buttress feature (1316) may be desirable in some versions to promote rigidity of shaft (1312) and avoid unintentional movement of shaft (1312) and/or lead screw latch (1320).

Lead screw latch (1320) is generally configured selectively fasten to lead screw drive shaft (1310) to selectively hold outer lead screw (1340) in a predetermined axial position. Although not shown, it should be understood that lead screw drive shaft (1310) may be axially secured to a portion of biopsy device (10) such as a portion of outer housing (14) or body (12). It should further be understood that such axial securement of lead screw drive shaft (1310) may be only with respect to axial (e.g., proximal-distal) movement of lead screw drive shaft (1310). In other words, lead screw drive shaft (1310) may still be feely rotatable within outer housing (14) or body (12). Additionally, lead screw latch (1320) may also be rotatable within outer housing (14) or body (12), but freely movable axially within outer housing (14) or body (12) along with outer lead screw (1340). As will be described in greater detail below, such rotation of lead screw latch (1320) may be desirable to promote selective detachment of lead screw latch (1320)

from lead screw drive shaft (1310) to permit axial movement of lead screw latch (1320) together with outer lead screw (1340).

Figure 29:
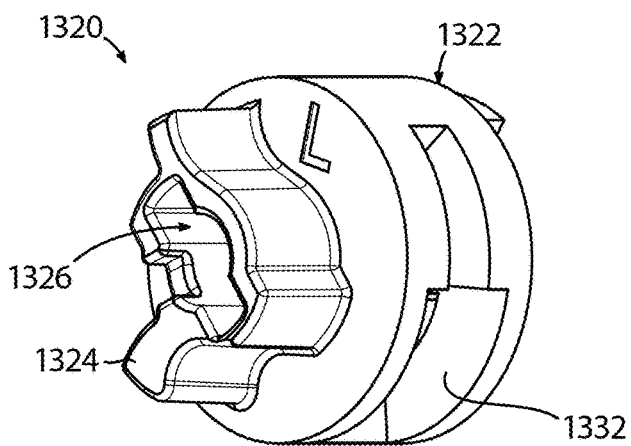
FIG. 29 depicts a perspective view of a lead screw latch of the piercer drive assembly of FIG. 27.
Figure 30:
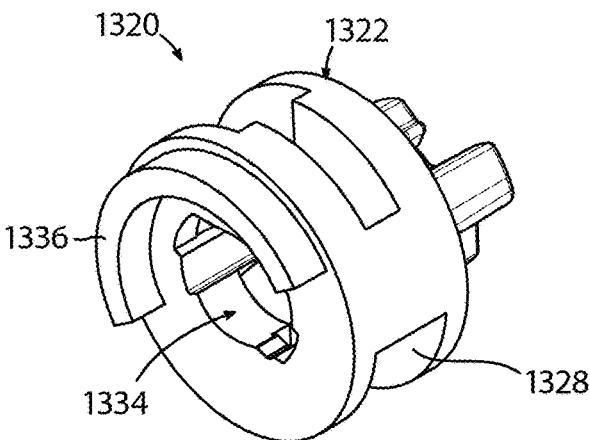
FIG. 30 depicts another perspective view of the lead screw latch of FIG. 29.
Figure 31:
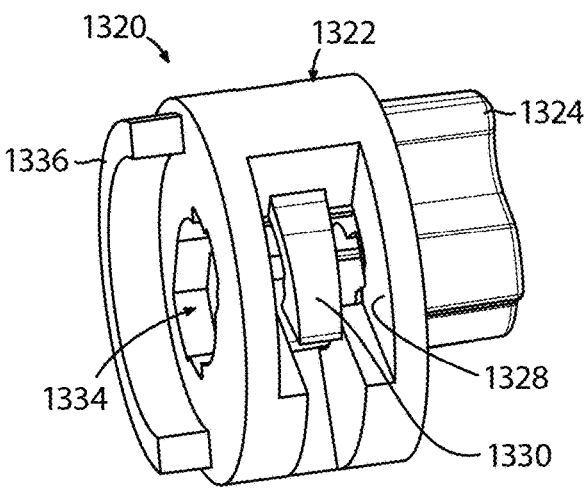
FIG. 31 depicts yet another perspective view of the lead screw latch of FIG. 29.

As best seen in FIGS. 29 through 31, lead screw latch (1320) includes a latch body (1322) having an actuation protrusion (1324) and a locating protrusion (1336) extending proximally and distally from latch body (1322), respectively. Latch body (1322) of the present version defines a generally cylindrical shape. However, it should be understood that in other versions, various alternative forms of latch body (1322) may be used.

Actuation protrusion (1324) provides one or more radially extending surfaces. As will be described in greater detail below, such radially extending surface of actuation protrusion (1324) are generally configured to engage other components of drive assembly (1100) to permit rotation of lead screw latch (1320) and release of lead screw latch (1320) from lead screw drive shaft (1310).

As best seen in FIG. 29, actuation protrusion (1324) defines a drive shaft bore (1326) centered within latch body (1322). Drive shaft bore (1326) defines a shape that is complementary to the shape of keyed portion (1314) of lead screw drive shaft (1310). Specifically, as described above, keyed portion (1314) of the present version includes a pair of wings. Thus, drive shaft bore (1326) includes an opening that is generally circular with outward projections to accommodate the shape of the pair of wings. Drive shaft bore (1326) is therefore generally configured to slidably receive keyed portion (1314) of drive shaft bore (1326). Accordingly, it should be understood that in versions where the particular configuration of keyed portion (1314) is varied, the particular configuration of drive shaft bore (1326) may likewise be varied to achieve such functionality.

The interior of latch body (1322) is generally hollow and includes a variety of features to facilitate interaction between lead screw latch (1320), lead screw drive shaft (1310), and outer lead screw (1340). In particular, the interior of latch body (1322) defines an internal proximal face (1328), one or more locating arms (1330), an internal distal face (1332) opposite of internal proximal face (1328). Internal proximal face (1328) is configured to abut a proximal end of keyed portion (1314) of lead screw drive shaft (1310) to selectively couple lead screw latch (1320) to lead screw drive shaft (1310). Specifically, each buttress feature (1316) of keyed portion (1314) may abut internal proximal face (1328) of latch body (1322) to hold keyed portion (1314) within lead screw latch (1320). Additionally, drive shaft bore (1326) extends through internal proximal face (1328) so that drive shaft bore (1326) is in communication with the interior of latch body (1322). Engagement between internal proximal face (1328) and the wings of keyed portion (1314) may therefore be released by rotation of lead screw latch (1320) to align the wings of keyed portion (1314) with drive shaft bore (1326) rather than internal proximal face (1328).

As best seen in FIG. 31, locating arms (1330) extend within the hollow interior of latch body (1322). Locating arms (1330) further extend inwardly into the hollow interior of latch body (1322). As will be described in greater detail below, locating arms (1330) are generally configured to locate the position of lead screw latch (1320) relative to outer lead screw (1340) to facilitate insertion of lead screw drive shaft (1310) into outer lead screw (1340). As will also be described in greater detail below, locating arms (1330) are further configured to permit at least some rotation of lead screw latch (1320) relative to outer lead screw (1340) to facilitate actuation of lead screw latch (1320) and release of lead screw latch (1320) from lead screw drive shaft (1310).

Internal distal face (1332) is generally configured to engage and/or abut at least a portion of outer lead screw (1340) to hold lead screw latch (1320) on proximal portion of outer lead screw (1340). As will be described in greater detail below, lead screw latch (1320) is generally configured to move axially with outer lead screw (1340). Thus, engagement between internal distal face (1332) and at least a portion of outer lead screw (1340) may be used to transfer axial movement of outer lead screw (1340) to lead screw latch (1320). Additionally, in some circumstances, engagement between internal distal face (1322) and at least a portion of outer lead screw (1340) may be used to hold outer lead screw (1340) in a predetermined axial position using lead screw latch (1320). It should be understood that such engagement between internal distal face (1332) and at least a portion of outer lead screw (1340) may be configured to still permit at least some rotation of lead screw latch (1320) relative to outer lead screw (1340). As will be described below, such relative rotation between lead screw latch (1320) and outer lead screw (1340) may be used to permit selective decoupling of lead screw latch (1320) from lead screw drive shaft (1310).

As best seen in FIGS. 30 and 31, actuation protrusion (1324) extends distally from latch body (1322). Actuation protrusion (1324) includes a square or rectangular cross-section extending around a portion of latch body (1322) forming a semi-circular pattern. In the present version, the semi-circular pattern of actuation protrusion (1324) is c-shaped or a half-circle. Regardless of the particular shape of actuation protrusion (1324), actuation protrusion (1324) may be configured to position lead screw latch (1320) relative to outer lead screw (1340). As will be described in greater detail below, it may be desirable to align outer lead screw (1340), lead screw latch (1320) and lead screw drive shaft (1310) for the purpose of insertion of lead screw drive shaft (1310) into lead screw latch (1320) and outer lead screw (1340). Actuation protrusion (1324) may thus facilitate such alignment by locating lead screw latch (1320) relative to outer lead screw (1340).

Latch body (1322) further defines a lead screw bore (1334) within a distal portion of latch body (1322) and positioned at the center of the curvature of actuation protrusion (1324). As will be described in greater detail below, lead screw bore (1334) may be sized and shaped to correspond to at least a portion of outer lead screw (1340) to hold a portion of outer lead screw (1340) within latch body (1322). Thus, internal distal face (1328) and lead screw bore (1334) may be configured to operate cooperatively to hold at least a portion of outer lead screw (1340) within latch body (1322). Optionally, a portion of lead screw bore (1334) may be oversized relative to a portion of outer lead screw (1340). Such an oversized portion of lead screw bore (1334) may be used in some versions of lead screw bore (1334) to permit insertion of outer lead screw (1340) into latch body (1322) during assembly. Additionally, the particular position of such an oversized portion of lead screw bore (1334) may correspond to other features of latch body (1322) (e.g., locating arms (1330) or other geometric features) so that a portion of outer lead screw (1340) may be coupled to latch body (1322) once assembly is complete and for operation of drive assembly (1100).

Figure 32:
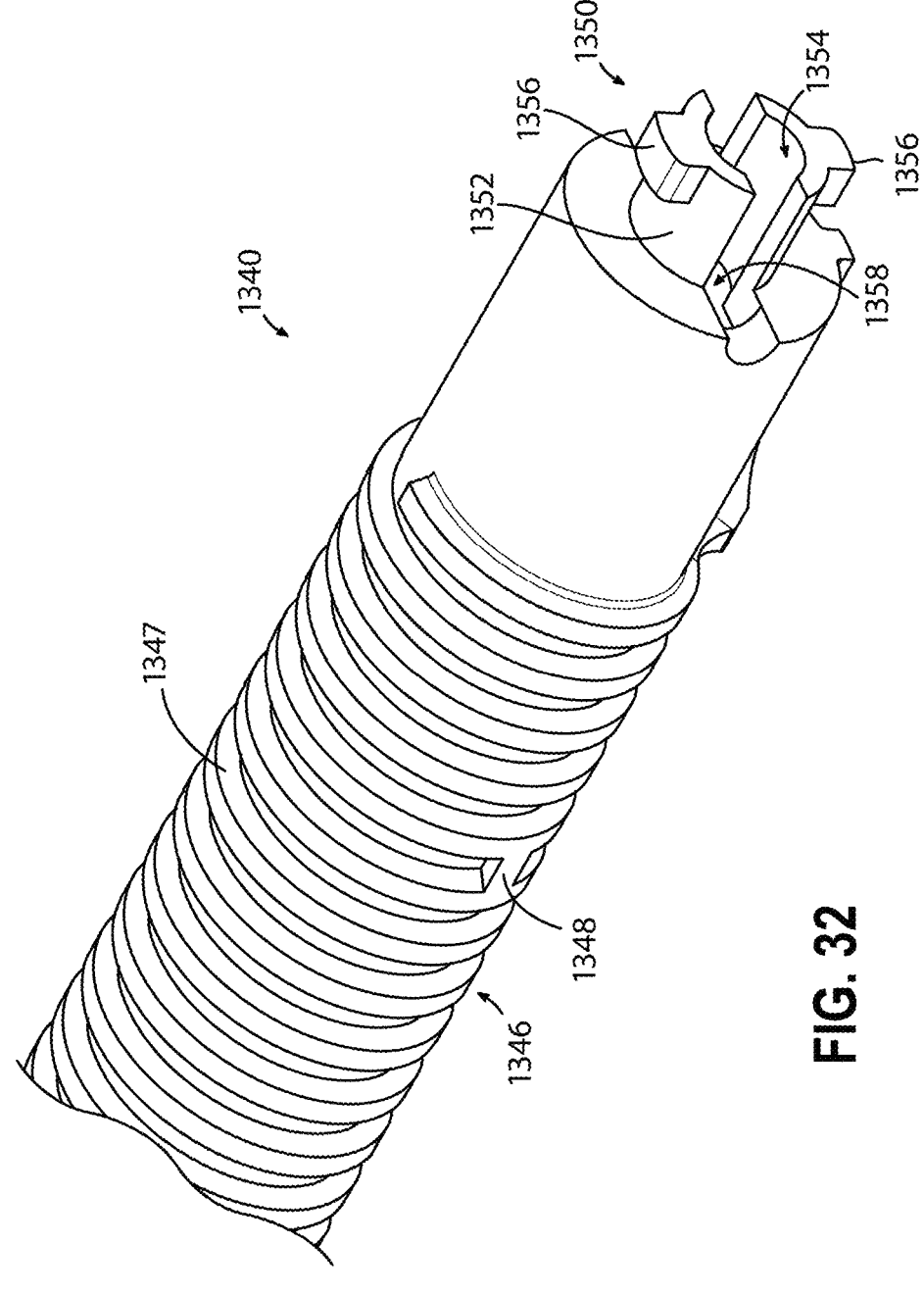
FIG. 32 depicts a detailed perspective view of an outer lead screw of the piercer drive assembly of FIG. 27.

As best seen in FIGS. 27 and 32, outer lead screw (1340) includes an open distal end (1342), an elongate threaded portion (1346), and an engagement end (1350), opposite open distal end (1342). Open distal end (1342) is configured to receive an insert (1360) and a piercer spring (1364) that may extend through a hollow interior of outer lead screw (1340). As will be described in greater detail below, insert (1360) and piercer spring (1364) may be used to interact with cutter drive assembly (1200) to drive movement one or more portions of cutter drive assembly (1200) based on movement of outer lead screw (1340).

Elongate threaded portion (1346) extends distally from open distal end (1342) to about the position of engagement end (1350). Elongate threaded portion (1346) includes relatively course threading (1347) configured to engage a portion of piercer carriage (1370). As will be described in greater detail below, elongate threaded portion (1346) is generally configured to translate rotational motion of outer lead screw (1340) into axial motion of piercer carriage (1370) via threading (1347). Additionally, as will be understood, axial movement of outer lead screw (1340) itself may also be transferred to piercer carriage (1370) via threading (1347).

As best seen in FIG. 32, threaded portion (1346) further includes a hard stop (1348) positioned at about the proximal end of threading. Hard stop (1348) in the present version is formed by a solid axially extending portion of threading (1347). Hard stop (1348) is generally configured to interrupt rotational motion of outer lead screw (1340) from being translated into axial motion of piercer carriage (1370). As will be described in greater detail below, such function of hard stop (1348) may be used in some versions in connection with an initialization sequence to establish a home position of piercer carriage (1370) relative to outer lead screw (1340).

Although hard stop (1348) of the present version is shown as being integral with threaded portion (1346), it should be understood that in other versions, hard stop (1348) may be incorporated into other components. For instance, in some versions, hard stop (1348) may be configured as a rib or ledge near the proximal end of threaded portion (1346). In such a configuration, hard stop (1348) may be configured to engage a receiving component integrated into piercer carriage (1370). Such a configuration may be desirable in some versions to provide a more robust hard stop (1348) for use in general operation of drive assembly (1100) rather than during initialization only.

In addition, or in the alternative, outer lead screw (1340) may include multiple hard stops (1348) in some versions. For instance, in some versions, a hard stop (1348) may be positioned on both the proximal end and the distal end of threaded portion (1346). Such a configuration may be desirable in some versions to facilitate control of outer lead screw (1340) by way of such hard stops (1348) only rather than relying on electronic control of motors. By controlling the position of outer lead screw (1340) via hard stops (1348) instead of electronic motor control, the speed of drive assembly (1100) may be increased by eliminating motor speed reductions.

Engagement end (1350) is disposed on a proximal end of outer lead screw (1340) opposite open distal end (1342). Engagement end (1350) includes a cylindrical portion (1352) having a proximal bore (1354), a pair of attachment protrusions (1356), and a key receiving portion (1358). Cylindrical portion (1352) defines a diameter less than the diameter of threaded portion (1346) and is configured for receipt within lead screw bore (1334) of lead screw latch (1320).

Figure 33:
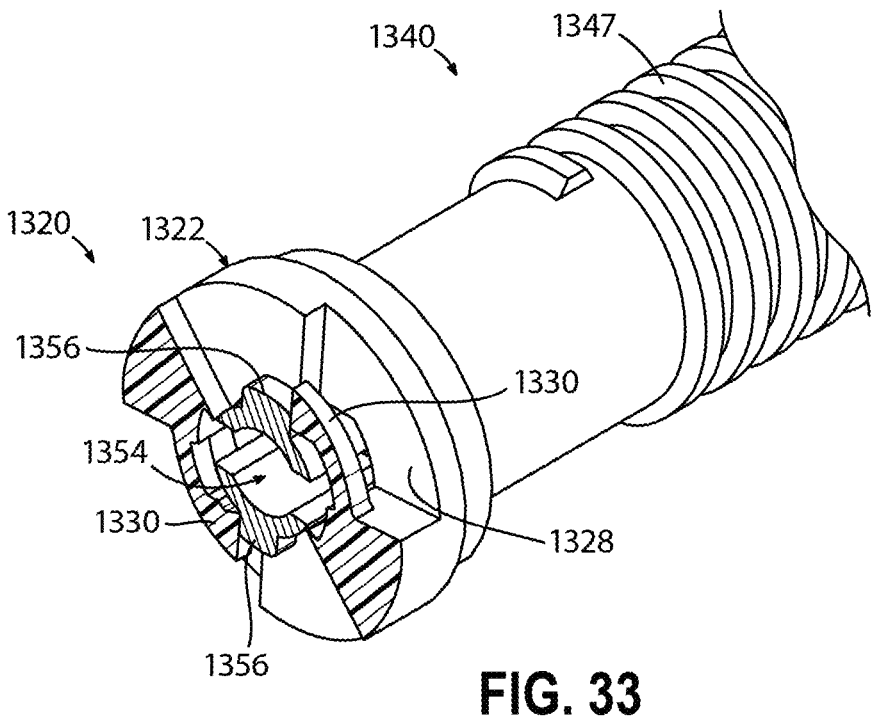
FIG. 33 depicts a partial perspective cross-sectional view of the outer lead screw of FIG. 32, a distal end of the outer lead screw being engaged with the lead screw latch of FIG. 29.
Figure 34:
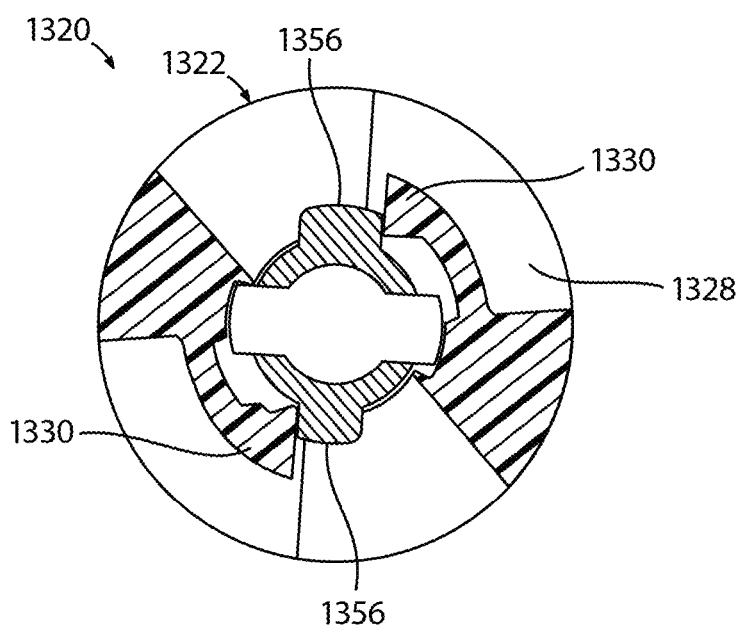
FIG. 34 depicts a front cross-sectional view of the outer lead screw of FIG. 32, the distal end of the outer lead screw being engaged with the lead screw latch of FIG. 29.

As best seen in FIGS. 33 and 34, each attachment protrusion (1356) is positioned proximate the proximal end of cylindrical portion (1352) such that each attachment protrusion (1356) may abut internal distal face (1328) of lead screw latch (1320). Specifically, cylindrical portion (1352) may extend through drive shaft bore (1326) of lead screw latch (1320) to position each attachment protrusion (1356) within the hollow interior of latch body (1322). When each attachment protrusion (1356) is received within latch body (1322), locating arms (1330) may also abut each attachment protrusion (1356) to hold each attachment protrusion (1356) in engagement with internal distal face (1332), while still permitting at least some relative rotation between lead screw latch (1320) and outer lead screw (1340). Although not shown, it should be understood that during insertion of attachment protrusions (1356) into latch body (1322), locating arms (1330) may flex or be moved outwardly away from attachment protrusion (1356) to permit attachment of lead screw latch (1320) to outer lead screw (1340). Once attachment of lead screw latch (1320) to outer lead screw (1340) is complete, attachment protrusions (1356) and locating arms (1330) may prevent decoupling until locating arms (1330) are physically manipulated by an operator to permit decoupling.

Proximal bore (1354) and key receiving portion (1358) are together configured to slidably receive at least a portion of lead screw drive shaft (1310). Specifically, proximal bore (1354) is configured to correspond to the size and shape of shaft (1312) (e.g., cylindrical). Similarly, key receiving portion (1358) is configured to correspond to the size and shape of keyed portion (1314). Key receiving portion (1358) may thus be configured to receive keyed portion (1314) to communicate rotary motion from lead screw drive shaft (1310) to outer lead screw (1340). As described above, keyed portion (1314) in the present version includes rectangular wings or protrusions. Thus, in the present version, key receiving portion (1358) includes a slot that may be complementary to the size and shape of the wings or protrusions of keyed portion (1314). However, it should be understood that in versions where the configuration of keyed portion (1314) is varied, the configuration of key receiving portion (1358) may likewise be varied to complement the size and shape of keyed portion (1314).

Figure 35:
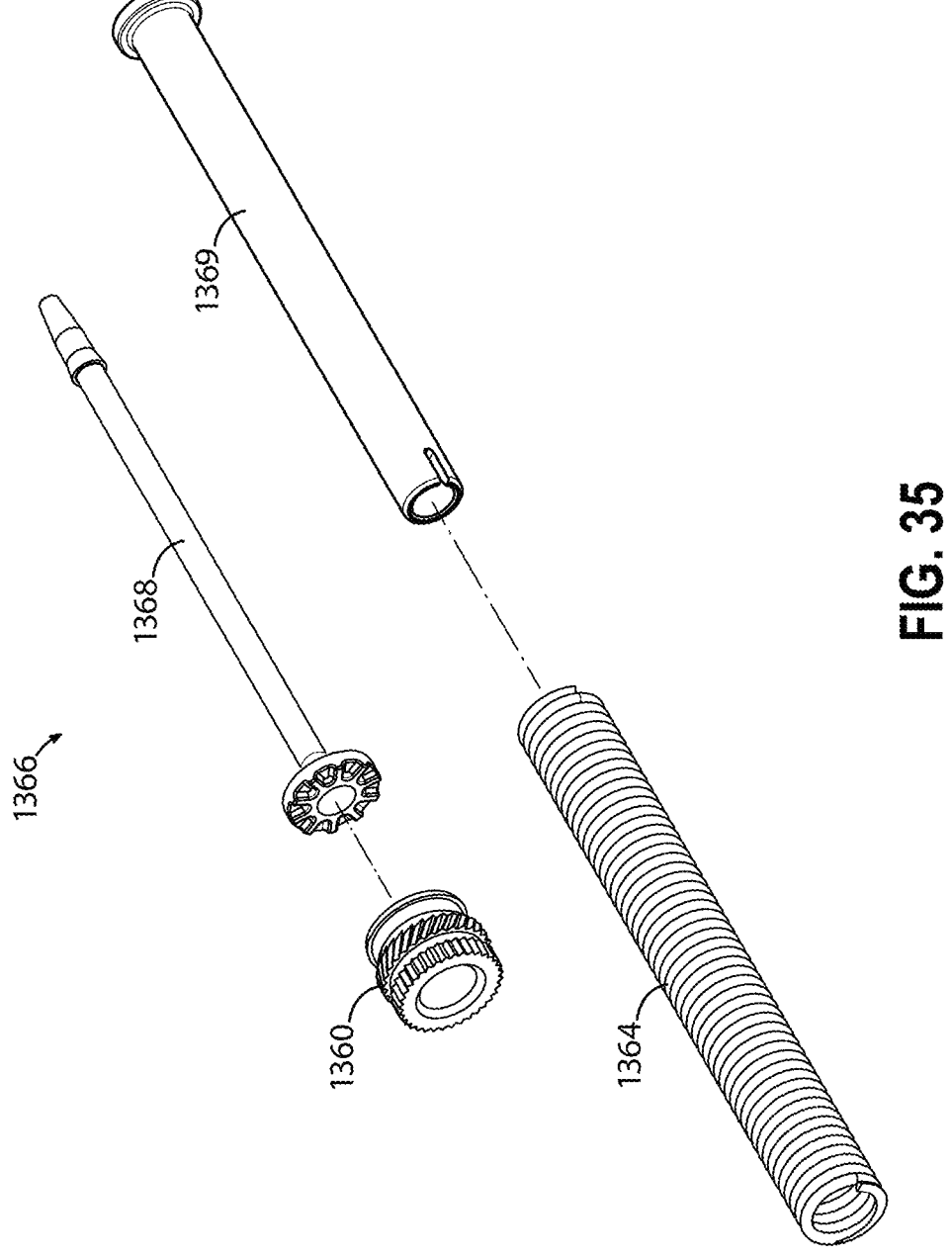
FIG. 35 depicts a perspective view of a spring guide of the piercer drive assembly of FIG. 27.

FIG. 35 shows insert (1360) and piercer spring (1364) in greater detail. As described above, insert (1360) and piercer spring (1364) may be disposed as an assembly within the hollow interior of outer lead screw (1340). Insert (1360) in the present example includes a brass insert with internal 10-32 threading. As will be described in greater detail below, insert (1360) may be fixedly secured proximate open distal end (1342) of outer lead screw (1340) to drive movement of, or otherwise interact with, one or more components of cutter drive assembly (1200).

Piercer spring (1364) of the present example includes a coil spring, although various alternative resilient features may be used in other versions. Piercer spring (1364) is generally configured to apply an axial force to outer lead screw (1340) and lead screw drive shaft (1310), which may be used to drive outer lead screw (1340) distally. As will be described in greater detail below, piercer spring (1364) may be used to fire piercer (22) via outer lead screw (1340) during a firing sequence.

In some versions, piercer spring (1364) may be used in connection with a spring guide (1366). For instance, in the present example, spring guide (1366) is configured to receive piercer spring (1364) to hold piercer spring (1364) within a predetermined length and with a known pre-load. Spring guide (1366) may thus be used in some versions to control the particular load applied to features of drive assembly (1100).

Spring guide (1366) of the present version includes a pin member (1368) and a sheath member (1369). Pin member (1368) and sheath member (1369) are both configured to fit within the interior of piercer spring (1364) and extend through piercer spring (1364). Pin member (1368) is configured to nest within sheath member (1369) and includes a distal end to provide a flat surface to engage other features of drive assembly (1100). Similarly, sheath member (1369) includes a sheath configured to receive at least a portion of pin member (1368) and includes a proximal end to provide a flat surface to engage other features of drive assembly (1100). As will be understood, pin member (1368) and sheath member (1369) are configured to work cooperatively to limit the compression of piercer spring (1364), thereby controlling the amount of force that may be introduced into piercer spring (1364).

Figures 36A, 36B:
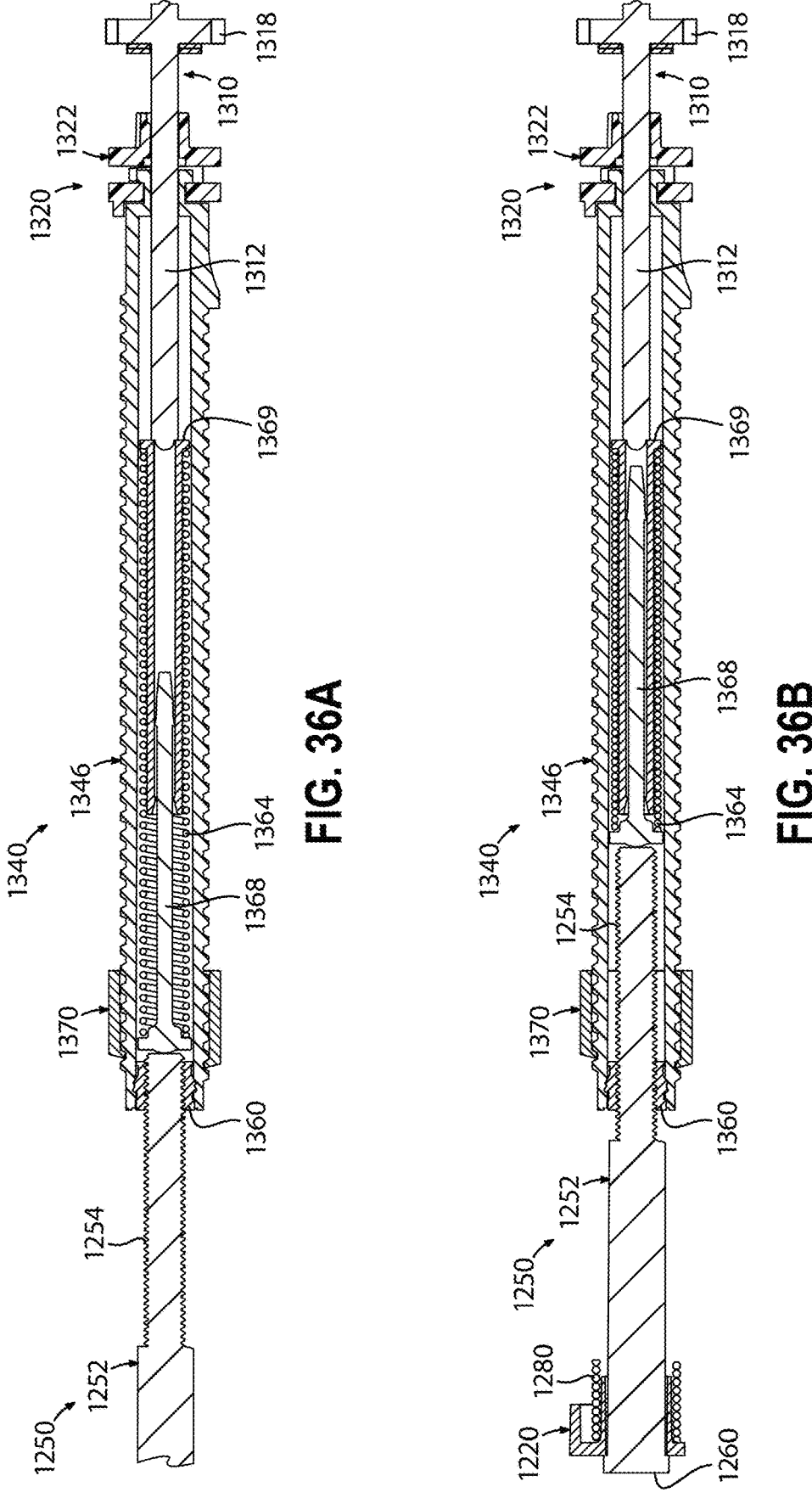
FIG. 36A depicts a side cross-sectional view of the piercer drive assembly of FIG. 27 with a piercer spring being in an expanded configuration, the cross-section being taken along line 36-36 of FIG. 26.
FIG. 36B depicts another side cross-sectional view of the piercer drive assembly of FIG. 27 with the piercer spring of FIG. 36A being in a compressed configuration.

As best seen in FIGS. 36A and 36B, insert (1360), piercer spring (1364) and spring guide (1366) may all be disposed within the interior of outer lead screw (1340). In particular, insert (1360) is fixedly secured within a distal portion of the interior of outer lead screw (1340) such that piercer spring (1364) and spring guide (1366) may be held within outer lead screw (1340) between insert (1360) and lead screw drive shaft (1310) and/or the proximal end of outer lead screw (1340). As will be described in greater detail below, insert (1360) may be configured to threadably engage a portion of cutter drive assembly (1200), such that a portion of cutter drive assembly (1200) may enter the interior of outer lead screw (1340) to compress piercer spring (1364) against lead screw drive shaft (1310). In other words, insert (1360) may be used to facilitate compression of piercer spring (1364) against lead screw drive shaft (1310) using a portion of cutter drive assembly (1200).

Figure 37:
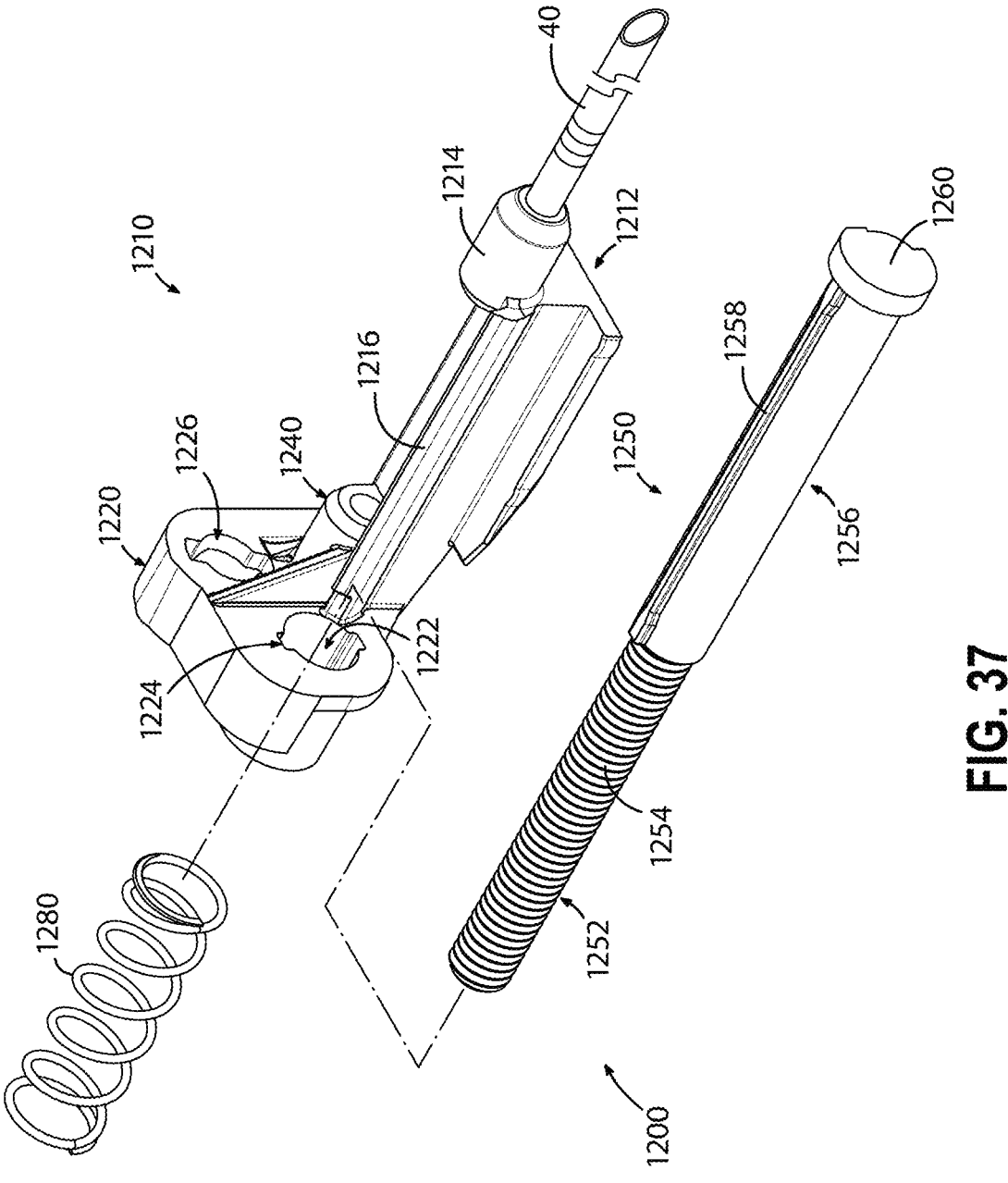
FIG. 37 depicts an exploded perspective view of a cutter drive assembly of the drive assembly of FIG. 26.

FIG. 37 shows cutter drive assembly (1200) in greater detail. As can be seen, cutter drive assembly (1200) includes a cutter carriage (1210), a cutter driver (1250), and a cutter spring (1280). Cutter carriage (1210), cutter driver (1250), and cutter spring (1280) are generally configured to operate cooperatively to move cutter (40) through a predetermined sequence including cocking, and firing. As will be described in greater detail below, cutter carriage (1210), cutter driver (1250), and cutter spring (1280) are further generally configured to interact with features of piercer drive assembly (1300) such that both cutter drive assembly (1200) and piercer drive assembly (1300) may be driven with a single motor.

Figure 38:
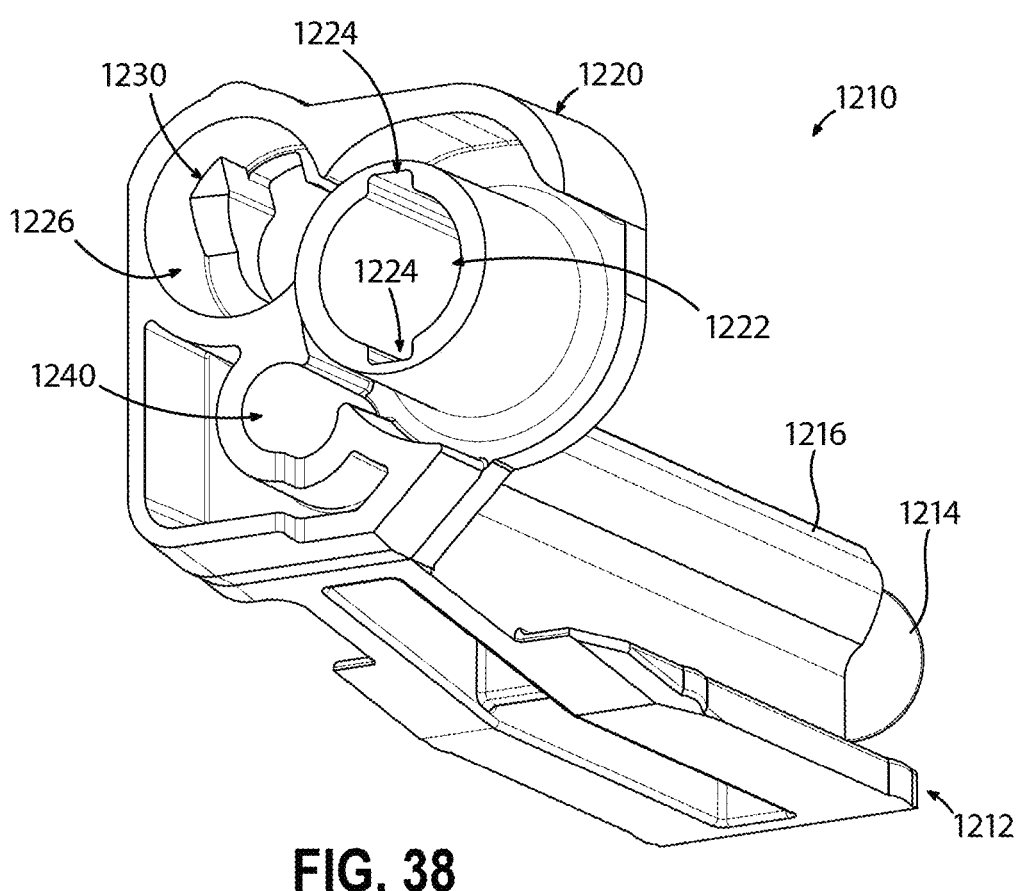
FIG. 38 depicts a perspective view of a cutter carriage of the cutter drive assembly of FIG. 37.
Figure 39:
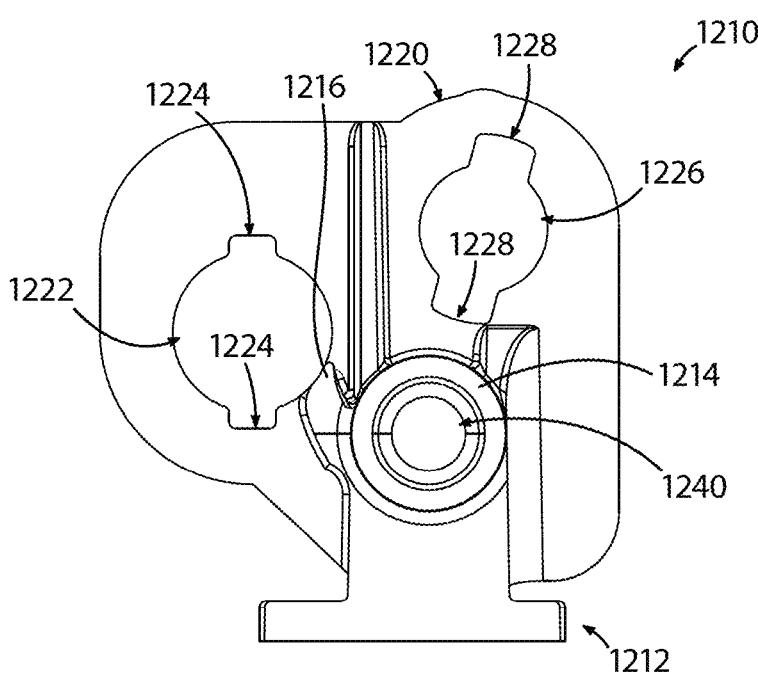
FIG. 39 depicts a side elevational view of the cutter carriage of FIG. 38.

As best seen in FIGS. 38 and 39, cutter carriage (1210) includes a carriage body (1212) that defines a cutter collar (1214), tissue manipulator (1216), and a proximal receiving end (1220). Cutter collar (1214) is configured to receive the proximal end of cutter (40) such that cutter (40) may extend distally from cutter collar (1214). In the present version, cutter (40) may be fixedly secured to cutter collar (1214). Alternatively, in other versions, cutter collar (1214) may be threaded, keyed, or otherwise structured to permit cutter (40) to be removably secured to cutter collar (1214). Cutter collar (1214) is generally of a hollow configuration to promote access to the proximal end of cutter (40) by piercer (22) and/or other structures.

Tissue manipulator (1216) is disposed between cutter collar (1214) and proximal receiving end (1220). Tissue manipulator (1216) is generally configured to direct tissue from piercer (22) into a tissue sample chamber or other structure during operation of drive assembly (1100). Thus, tissue manipulator (1216) is configured to receive at least a portion of piercer (22) such that piercer (22) may extend and move through tissue manipulator (1216). As will be described in greater detail below, in some versions, tissue manipulator (1216) may be used in connection with other features such as a flexible member, a wiper, or a blade feature.

Proximal receiving end (1220) of carriage body (1212) is generally configured to engage various components of drive assembly (1100) to drive movement of cutter (40) via movement of cutter carriage (1210). In particular, proximal receiving end (1220) defines a driver bore (1222), a shaft bore (1226), and a piercer bore (1240). Driver bore (1222) is generally circular and is configured to slidably receive at least a portion of cutter driver (1250). As best seen in FIG. 39, driver bore (1222) includes channels (1224) extending along the axis of driver bore (1222). As will be described in greater detail below, channels (1224) are generally configured to engage corresponding features of cutter driver (1250) such that cutter driver (1250) may be keyed relative to carriage body (1212). Although driver bore (1222) of the present versions includes a pair of channels (1224), it should be understood that in other versions, any other suitable number of channels (1224) may be used. Alternatively, in some versions, channels (1224) may take on a variety of other geometric configurations corresponding to features of cutter driver (1250).

Shaft bore (1226) is generally configured to receive one or more components of drive assembly (1100) to lock cutter carriage (1210) in one or more predetermined axial positions. As best seen in FIGS. 38 and 39, shaft bore (1226) defines a generally cylindrical shape that may correspond to other structures of drive assembly (1100). Additionally, shaft bore (1226) includes one or more channels (1228). As will be described in greater detail below, channels (1228) may be configured to receive one or more structures protruding from a shaft to release movement of cutter carriage (1210) when the shaft is in some positions and lock the position of cutter carriage (1210) when the shaft is in other positions.

Adjacent to shaft bore (1226), proximal receiving end (1220) further defines a hard stop protrusion (1230). Hard stop protrusion (1230) extends from a proximal face of proximal receiving end (1220) and is positioned proximate a channel (1228) of shaft bore (1226). As will be described in greater detail below, hard stop protrusion (1230) may be used in some versions for initialization of drive assembly (1100). In other words, in some versions, hard stop protrusion (1230) may be used to establish a known home position or initial position for one or more components of drive assembly (1100) associated with shaft bore (1226).

Piercer bore (1240) is configured to slidably receive at least a portion of piercer (22). Thus, piercer bore (1240) defines a size and shape corresponding to the cross-sectional size and shape of piercer (22). Additionally, piercer bore (1240) is aligned with an axis defined by cutter (40) and cutter collar (1214) such that piercer (22) may be directed into cutter (40).

Returning to FIG. 37, cutter driver (1250) a threaded portion (1252) and a sliding portion (1256). Threaded portion (1252) includes relatively fine threading (1254) in comparison to threading (1347) of outer lead screw (1340). Threading (1254) is also in an oppositely threaded configuration relative to threading (1347) of outer lead screw (1340). In other words, threading (1254) of cutter driver (1250) may be of a right-hand threaded configuration, while threading (1347) of outer lead screw (1340) may be of a left-hand threaded configuration. Of course, in other versions, the opposite configuration may be used with threading (1254) being of a left-hand threaded configuration and threading (1347) being of a right-hand threaded configuration.

Threading (1254) is generally configured to engage insert (1360) disposed within outer lead screw (1340) such that rotation of outer lead screw (1340) may be used to drive translation of cutter driver (1250). Moreover, such engagement between insert (1360) and threading (1254) may be configured to also convert translation of outer lead screw (1340) into corresponding translation of cutter driver (1250). As will be described in greater detail below, such engagement between insert (1360) and threading (1254) may be used to facilitate cocking and firing of cutter (40) in combination with other components of drive assembly (1100).

Sliding portion (1256) extends distally from threaded portion (1252) along a common longitudinal axis. Sliding portion (1256) defines a generally smooth cylindrical cross-section and includes one or more outwardly extending protrusions (1258) and a distal engagement end (1260). Protrusions (1258) in the present version are configured as keys that correspond to the shape of channels (1224) of driver bore (1222) in cutter carriage (1210). Thus, protrusions (1258) and channels (1224) may act cooperatively to fix the rotational position of cutter driver (1250) relative to cutter carriage (1210), yet still permit sliding of cutter driver (1250) relative to cutter carriage (1210). Although the present version uses a key-keyway configuration to promote such functionality, it should be understood that in other examples, various alternative alignment features may be used. For instance, in some versions, sliding portion (1256) may define an irregularly shaped cross-section such as hexagonal and driver bore (1222) may define a bore having a complementary shape. Still other configurations for protrusions (1258) and channels (1224) will be apparent to those of ordinary skill in the art in view of the teachings herein.

Distal engagement end (1260) is disposed on the distal end of cutter driver (1250). In the present version, distal engagement end (1260) is configured to engage the distal face of receiving end (1220) of cutter carriage (1210). Thus, distal engagement end (1260) is generally configured as a flange having a greater diameter relative to the diameter defined by sliding portion (1256) and/or threaded portion (1252). As will be described in greater detail below, such engagement between distal engagement end (1260) and receiving end (1220) may be used as a stop to prevent at least some relative movement between cutter carriage (1210) and cutter driver (1250).

Cutter spring (1280) of the present version is a coil spring that is configured to receive cutter driver (1250) such that cutter driver (1250) may extend through cutter spring (1280). Thus, cutter spring (1280) may be guided by cutter driver (1250) for compression of cutter spring (1280) by cutter carriage (1210). As will be described in greater detail below, cutter spring (1280) is generally configured to drive distal translation of cutter carriage (1210) to fire cutter (40). Thus, the distal end of cutter spring (1280) is configured to engage receiving end (1220) of cutter carriage (1210). Meanwhile, the proximal end of cutter spring (1280) is configured to engage a journal, protrusion, or other structure of outer housing (14) such that cutter spring (1280) may be compressed between cutter carriage (1210) and outer housing (14).

Figure 40:
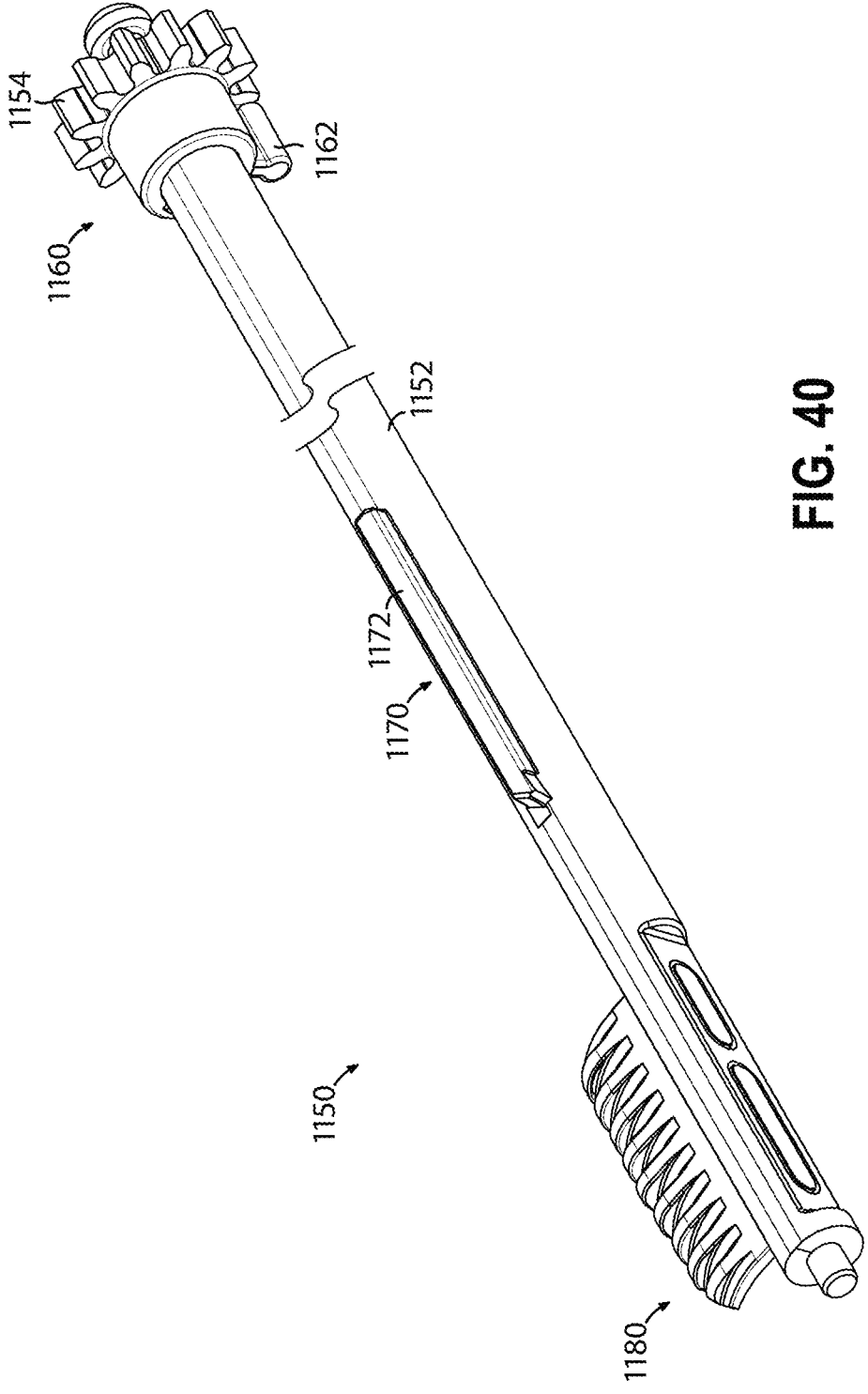
FIG. 40 depicts a perspective view of a control shaft of the drive assembly of FIG. 26.

Drive assembly (1100) further includes a control shaft (1150) (also referred to as an actuation mechanism, control, or trip mechanism), which may be configured to interact with cutter drive assembly (1200) and piercer drive assembly (1300) to initiate movement of cutter (40) and piercer (22) through a predetermined sequence of motion. As best seen in FIG. 40, control shaft (1150) includes an elongate shaft (1152) having a drive gear (1154), a latch portion (1160), a release portion (1170), and a tissue manipulation portion (1180). Elongate shaft (1152) defines a generally cylindrical cross-section and is configured to extend from piercer drive assembly (1300) to cutter drive assembly (1200).

Drive gear (1154) is configured to engage a gear associated with a motor or other drive mechanism to drive rotation of control shaft (1150). In some versions, drive gear (1154) may be driven by the same motor used to drive gear (1318) of piercer drive assembly (1300) using a transmission, gearing, and/or other mechanisms. In other versions, drive gear (1154) may be driven by a dedicated motor. In still other versions, drive gear (1154) may be driven manually by a knob, thumbwheel, crank, or other manual drive mechanism.

Latch portion (1160) is proximate drive gear (1154) and the proximal end of control shaft (1150). Latch portion (1160) is generally configured to engage piercer drive assembly (1300) to control one or more operations of piercer drive assembly (1300). In particular, latch portion (1160) includes an actuator (1162) protruding outwardly from elongate shaft (1152). As will be described in greater detail below, actuator (1162) is configured to engage actuation protrusion (1324) of lead screw latch (1320) to selectively release lead screw latch (1320) from lead screw drive shaft (1310).

Actuator (1162) extends outwardly from a specific point on elongate shaft (1152) such that engagement of actuator (1162) with piercer drive assembly (1300) may occur at a specific rotational position of control shaft (1150). As will be described in greater detail below, the specific point of extension for actuator (1162) may correspond to the particular position of other features of control shaft (1150). Such a relationship between features of control shaft (1150) may be desirable to promote sequential control of cutter drive assembly (1200) and piercer drive assembly (1300) via continuous rotation of control shaft (1150).

Release portion (1170) is disposed along elongate shaft (1152) between latch portion (1160) and tissue manipulation portion (1180) and includes a pair of wings (1172). Wings (1172) extend outwardly in opposite directions from elongate shaft (1152) and define a square or rectangular cross-section. Wings (1172) further extend along the length of elongate shaft (1152) for a predetermined distance. As will be described in greater detail below, the particular length of wings (1172) may correspond to a travel distance of cutter carriage (1210).

Each wing (1172) is configured to be received within a corresponding channel (1228) of shaft bore (1226) of cutter carriage (1210). Thus, the shape of each wing (1172) is complementary to the shape of each channel (1228). Although a square or rectangular shape is used in the present version for wings (1172) and channels (1228), it should be understood that in other examples, various alternative shapes may be used in other versions.

The particular position of release portion (1170) along elongate shaft (1152) is generally configured to permit release portion (1170) to engage one or more portions of cutter drive assembly (1200). In particular, elongate shaft (1152) is sized to fit within shaft bore (1226) of cutter carriage (1210). Similarly, and as described above, wings (1172) are sized to fit within channels (1228) of shaft bore (1226). As will be described in greater detail below, control shaft (1150) may be used to rotate release portion (1170) to selectively lock on unlock the position of cutter carriage (1210) relative to the length of control shaft (1150). As will be understood, such functionality may be used to facilitate releasing of cutter carriage (1210) to fire cutter (40).

Tissue manipulation portion (1180) is disposed proximate the distal end of elongate shaft (1152). Tissue manipulation portion (1180) is generally configured to manipulate a tissue sample out of piercer (22) and into a tissue chamber in response to rotation of control shaft (1150).

FIGS. 41 through 51 show a version of a use of biopsy device (10) in connection with drive assembly (1100) described above. In particular, in such a use, drive assembly (1100) is generally used to cock and then fire piercer (22) and cutter (40) in a predetermined sequence to penetrate a suspicious lesion and then sever a tissue sample thereof. Once piercer (22) and cutter (40) are fired, piercer (22) is retracted relative to cutter (40) to permit collection of the severed tissue by an operator. The cocking and firing process may then be repeated as many times as desired to collect as many tissue samples as desired by the user.

Figure 41:
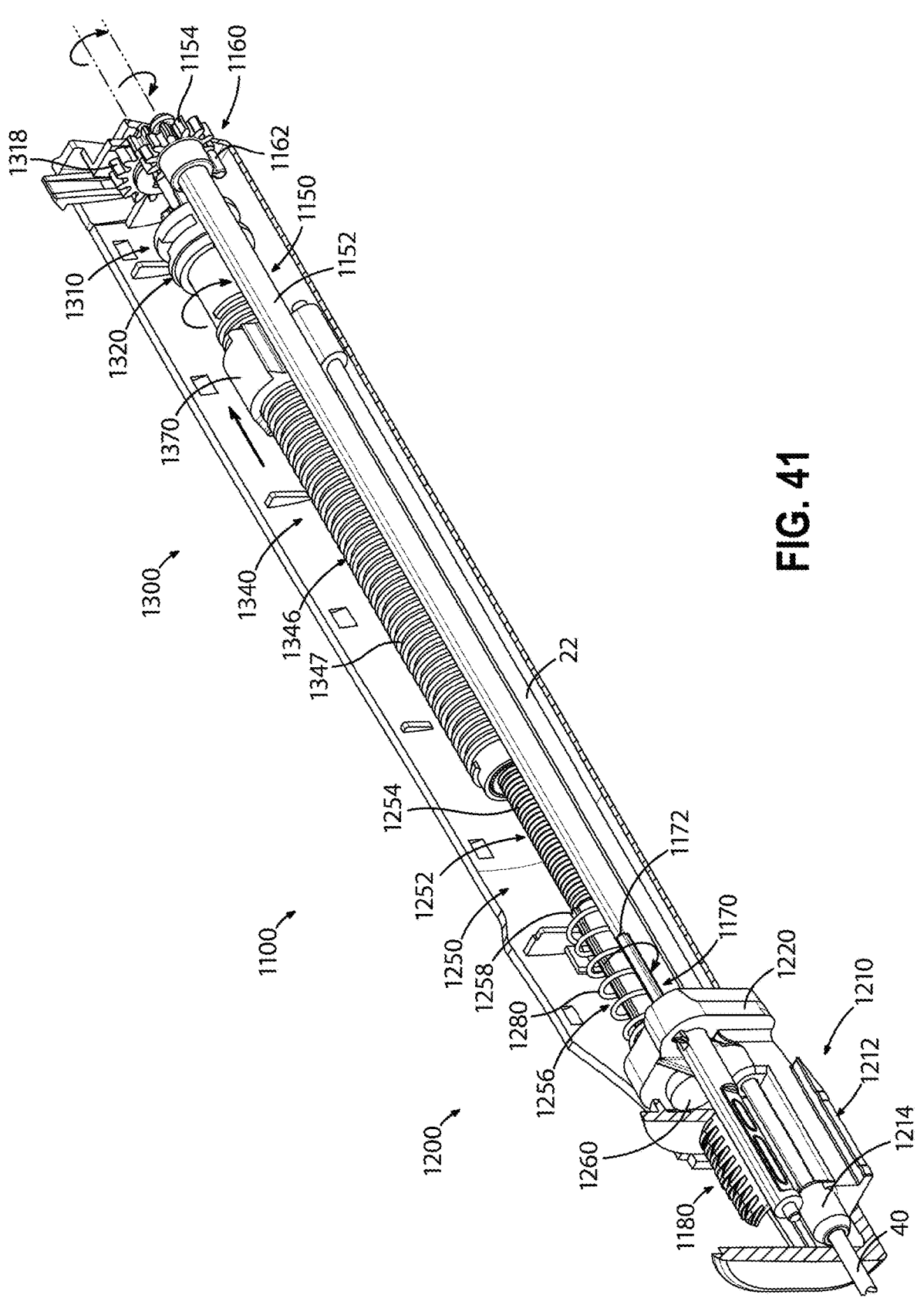
FIG. 41 depicts a perspective cutaway view of the drive assembly of FIG. 26 in use with the core needle biopsy device of FIG. 1, the drive assembly in an initialization configuration.
Figure 42:
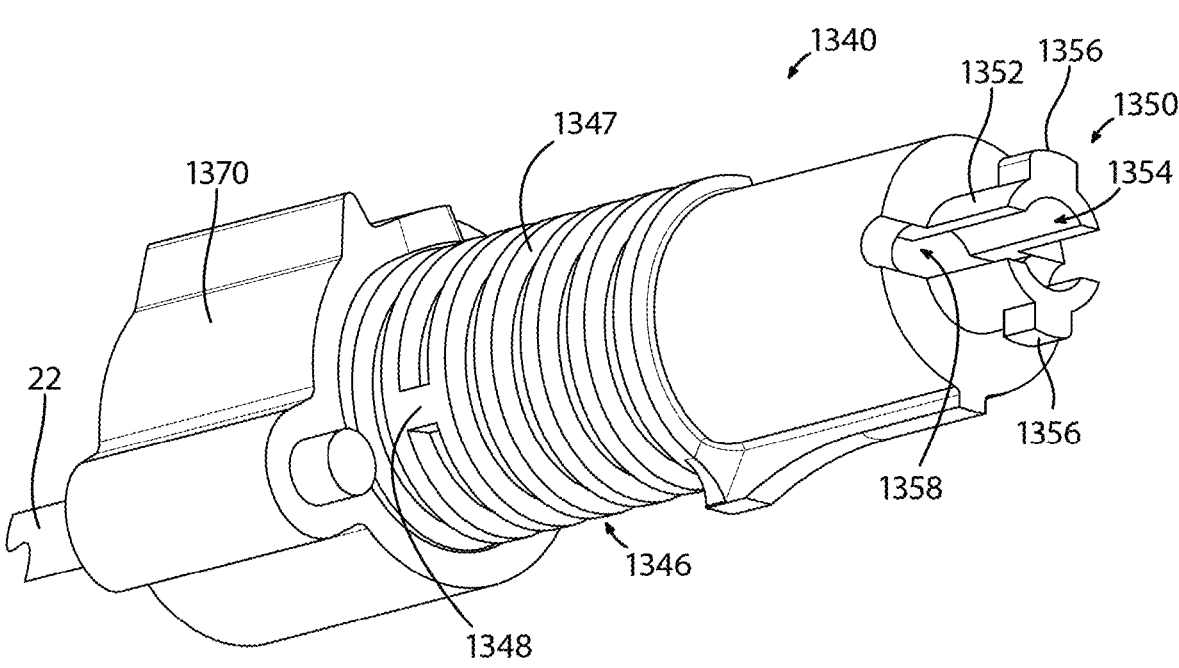
FIG. 42 depicts a detailed perspective view of the piercer drive assembly of FIG. 27 with a piercer carriage engaging a hard stop of the outer lead screw of FIG. 32.
Figure 43:
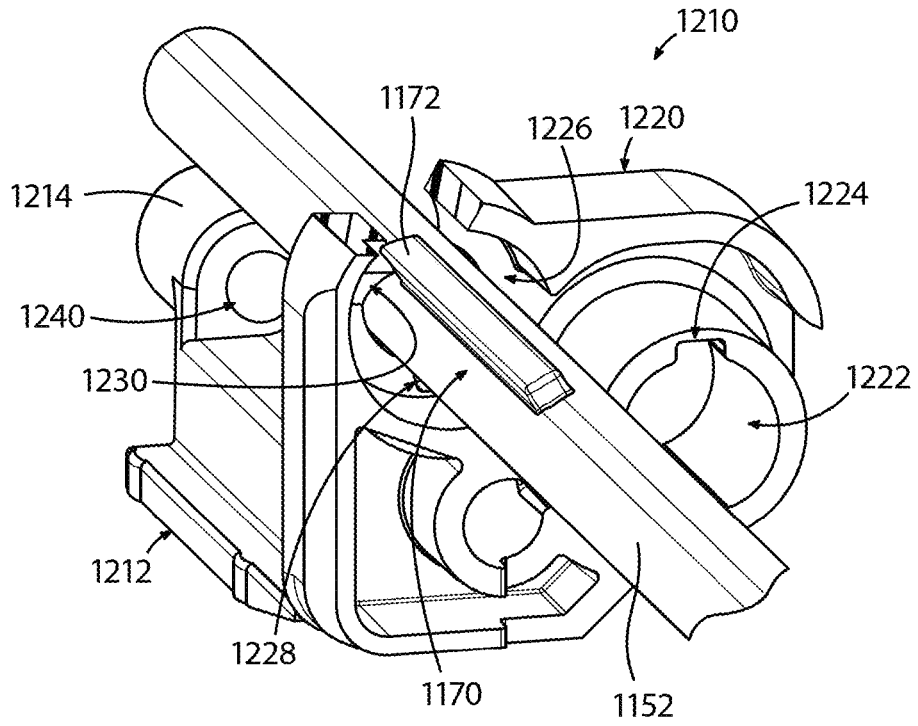
FIG. 43 depicts a detailed perspective view of the cutter dive assembly of FIG. 37 with the control shaft of FIG. 40 engaging a hard stop protrusion of the cutter drive assembly.

FIGS. 41 through 43 show an initial operation of drive assembly (1100) to initialize drive assembly (1100). During initialization, a home position is established for various components such as outer lead screw (1340), piercer carriage (1370), control shaft (1150), and cutter carriage (1210). Initialization may be used in the present version to establish a common initial position for drive assembly (1100) before beginning other operational procedures so that such operational procedures proceed sequentially based on predetermined movements performed in concert.

As best seen in FIG. 41, initialization begins with rotation of lead screw drive shaft (1310) in a clockwise direction (relative to the view in FIG. 41), which results in corresponding rotation of outer lead screw (1340). During rotation of outer lead screw (1340) in the clockwise direction, engagement between threading (1347) of outer lead screw (1340) and piercer carriage (1370) results in piercer carriage (1370) translating proximally down the length of outer lead screw (1340), which results in corresponding translation of piercer (22). Also during rotation of outer lead screw (1340) in the clockwise direction, engagement between threading (1254) of cutter driver (1250) and insert (1360) disposed within outer lead screw (1340) results in distal translation of cutter driver (1250) relative to outer lead screw (1340). Distal translation of cutter driver (1250) may permit corresponding distal movement of cutter carriage (1210) via cutter spring (1280), resulting in corresponding distal translation of cutter (40).

Rotation of outer lead screw (1340) may continue until piercer carriage (1370) reaches hard stop (1348) of outer lead screw (1340) as shown in FIG. 42. At this stage, further clockwise rotation of outer lead screw (1340) is physically prevented by hard stop (1348) of outer lead screw (1340). In some versions, this point may be identified by control circuitry associated with the motor or other driver of drive gear (1318) by a current spike or other electrical property responsive to an increased mechanical load applied to drive gear (1318). Once hard stop (1348) is reached, piercer (22) is in its furthest proximal position, which corresponds to the home position for piercer (22). Similarly, cutter (40) is in its furthest distal position, which corresponds to the home position for cutter (40).

In some versions, the home position of outer lead screw (1340) identified by hard stop (1348) may be slightly offset from the true initialization position identified by hard stop (1348). In other words, the home position of outer lead screw (1340) may be separate from the initialization position of outer lead screw (1340). Such an offset may be facilitated by control circuitry and/or motor control described above. This offset may be desirable in some versions to reduce wear on motors used to drive outer lead screw (1340). However, as described above, hard stop (1348) may be of a more robust configuration in some versions to facilitate control directly via hard stop (1348) rather than via motor control. In such versions, the initialization position of outer lead screw (1340) may be substantially similar to the home position of outer lead screw (1340).

Also during initialization, the home position for control shaft (1150) may be established. In particular, as seen in FIG. 41, control shaft (1150) may be rotated in a clockwise direction. Such clockwise rotation of control shaft (1150) may continue until one or more wings (1172) of release portion (1170) engage hard stop protrusion (1230) of cutter carriage (1210). Once one or more wings (1172) engage hard stop protrusion (1230), further clockwise rotation may be physically prevented by hard stop protrusion (1230). In some versions, this point may be identified by control circuitry associated with the motor or other driver of drive gear (1154) by a current spike or other electrical property responsive to an increased mechanical load applied to drive gear (1154).

After the home position of control shaft (1150) is established by rotation to engage one or more wings (1172) with hard stop protrusion (1230), the rotation of control shaft (1150) may be reversed to rotate in a counterclockwise direction. In some versions, this reversing of rotation may be used to ensure lead screw latch (1320) is positioned to couple to outer lead screw (1340). In particular, control shaft (1150) may rotate through a complete 360° rotation. During this rotation, actuator (1162) of control shaft (1150) may engage lead screw latch (1320) to rotate lead screw latch (1320) into a predetermined position. Versions of such actuation are described in greater detail below in connection with FIGS. 46 and 50.

In some versions, the initialization operation described above may be performed in a predetermined sequence. For instance, as noted above, wings (1172) of control shaft (1150) may engage channels (1228) of shaft bore (1226) depending on the position of cutter carriage (1210) relative to control shaft (1150). Thus, in the present example, initialization of control shaft (1150) may be performed after initialization of piercer (22) and cutter (40) to establish a position of cutter carriage (1210) that may permit rotation of control shaft (1150) and engagement between one or more wings (1172) and hard stop protrusion (1230). In the present version, drive assembly (1100) is configured such that cutter carriage (1210) is in the furthest distal position when control shaft (1150) initialization may occur. However, in other versions, various alternative initialization sequences may be used.

Figure 44:
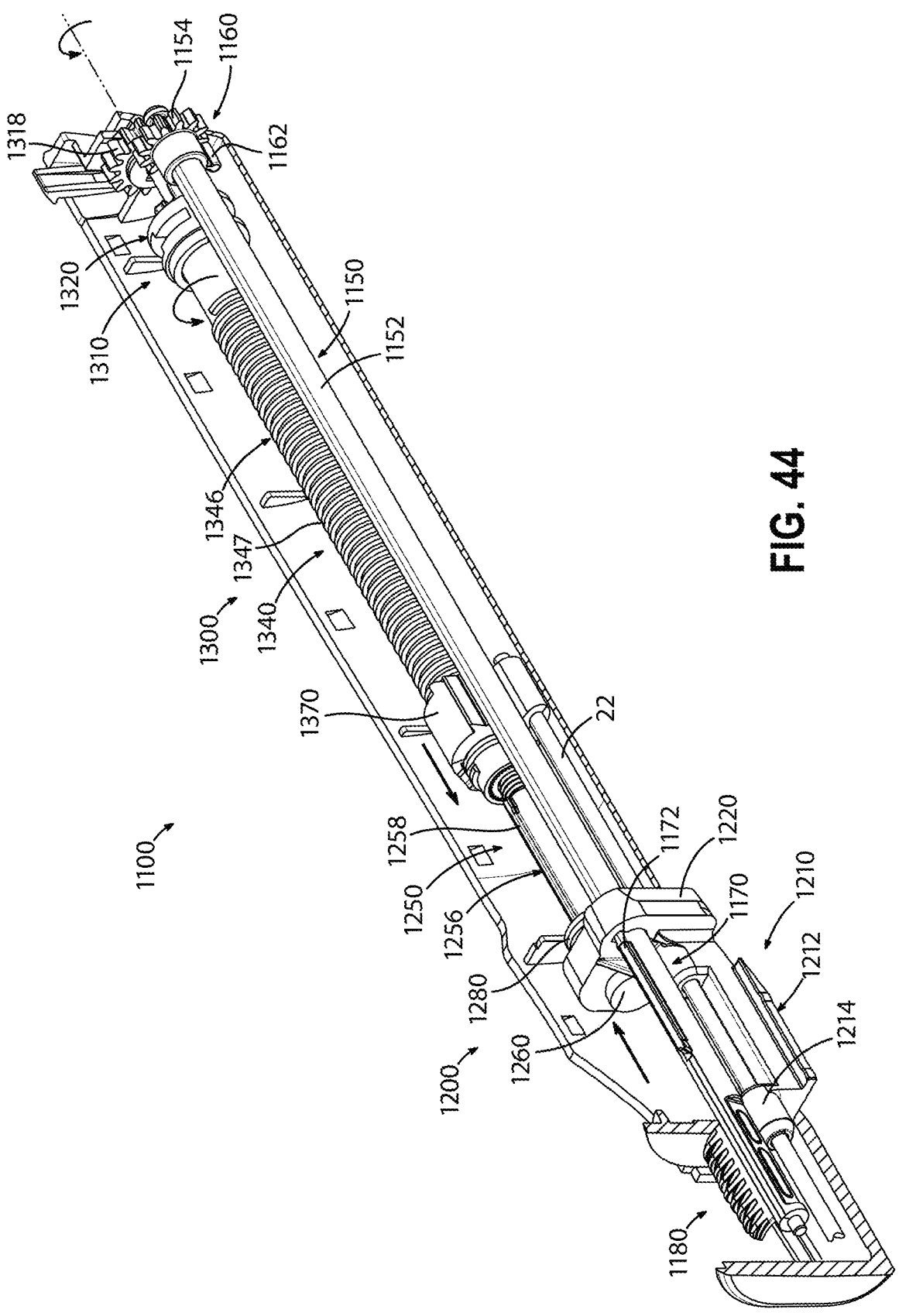
FIG. 44 depicts another perspective cutaway view of the drive assembly of FIG. 26 in use with the core needle biopsy device of FIG. 1, the drive assembly in a cocked configuration.

After initialization is performed, both piercer (22) and cutter (40) may be cocked for firing. As seen in FIG. 44, cocking is performed by rotating lead screw drive shaft (1310) in a counterclockwise direction (relative to the view in FIG. 44). Rotation of lead screw drive shaft (1310) may result in a corresponding counterclockwise rotation of outer lead screw (1340). As outer lead screw (1340) is rotated in the counterclockwise direction, piercer carriage (1370) is translated distally by engagement between threading (1347) of outer lead screw (1340) and piercer carriage (1370). This movement advances piercer (22) from the home position described above to a cocked or pre-fired position.

Counterclockwise rotation of outer lead screw (1340) also results in proximal translation of cutter driver (1250) relative to outer lead screw (1340) by engagement between threading (1254) of cutter driver (1250) and insert (1360) disposed within outer lead screw (1340). This translation of outer lead screw (1340) retracts at least a portion of cutter driver (1250) into the hollow interior of outer lead screw (1340) to compress piercer spring (1364) between cutter driver (1250) and lead screw drive shaft (1310). Such compression of piercer spring (1364) may load piercer spring (1364) for subsequent firing of piercer (22).

Translation of cutter driver (1250) relative to outer lead screw (1340) may also result in corresponding proximal translation of cutter carriage (1210) via engagement between distal engagement end (1260) of cutter driver (1250) and receiving end (1220) of cutter carriage (1210). Such proximal translation of cutter carriage (1210) results in compression of cutter spring (1280) between cutter carriage (1210) and a portion of outer housing (14). Such compression of cutter spring (1280) may load cutter spring (1280) for subsequent firing of cutter (40).

Figure 45:
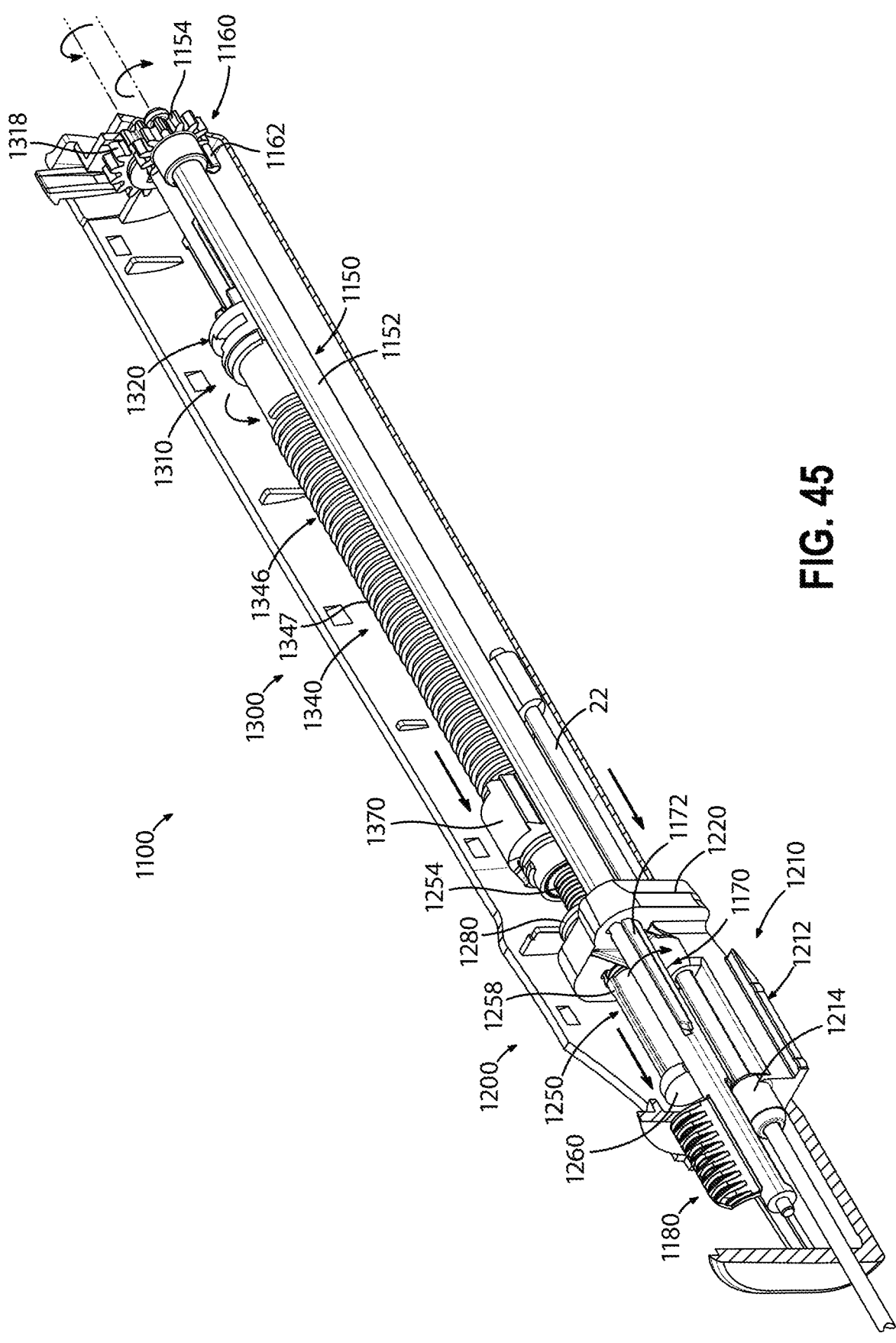
FIG. 45 depicts yet another perspective cutaway view of the drive assembly of FIG. 26 in use with the core needle biopsy device of FIG. 1, the drive assembly in a piercer firing configuration.

Once cocking is complete, drive assembly (1100) may be used to fire piercer (22) and cutter (40) sequentially. As shown in FIG. 45, firing may be initiated by rotating control shaft (1150) in a counterclockwise direction (relative to the view in FIG. 45). As control shaft (1150) is rotated, engagement between elements of control shaft (1150), lead screw latch (1320), and cutter carriage (1210) may cause sequential firing of piercer (22) followed by cutter (40).

Figure 46:
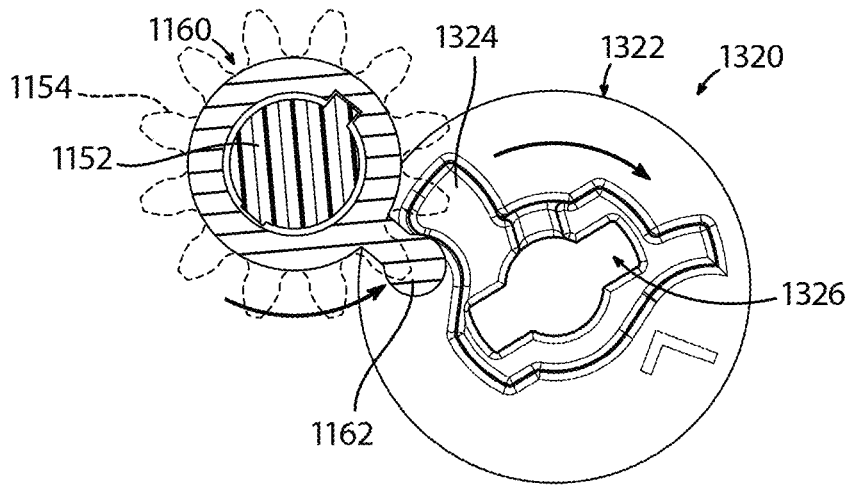
FIG. 46 depicts a rear elevational view of the piercer drive assembly of FIG. 27 with the control shaft of FIG. 40 being rotated to actuate the lead screw latch of FIG. 29.

As best seen in FIG. 46, during rotation of lead screw latch (1320), actuator (1162) first engages actuation protrusion (1324) of lead screw latch (1320). Such engagement results in at least some rotation of lead screw latch (1320) to align drive shaft bore (1326) with lead screw drive shaft (1310) to permit keyed portion (1314) of lead screw drive shaft (1310) to slide through drive shaft bore (1326). Once suitable alignment is achieved, the compression of piercer spring (1364) may force leadscrew drive shaft (1310) out of outer lead screw (1340), thereby projecting lead screw latch (1320), outer lead screw (1340), piercer carriage (1370), piercer (22) and cutter driver (1250) distally to fire piercer (22).

Figure 47:
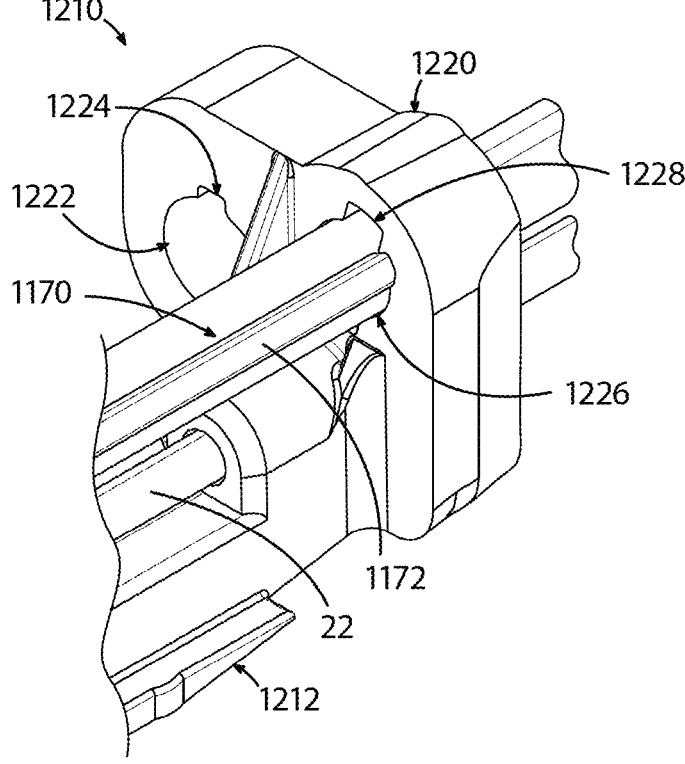
FIG. 47 depicts a detailed perspective view of the cutter drive assembly of FIG. 37 with the control shaft of FIG. 40 being rotated to hold the cutter carriage of FIG. 38 in a predetermined axial position.

As best seen in FIGS. 45 and 47, rotation of control shaft (1150) in the clockwise direction also results in movement of wings (1172) of release portion (1170) out of alignment with channels (1228) of shaft bore (1226). Such misalignment may occur prior to engagement between actuator (1162) and actuation protrusion (1324). As a result, distal advancement of cutter carriage (1210) may be prevented by wings (1172) of release portion (1170) despite the distal movement of cutter driver (1250) described above.

Figure 48:
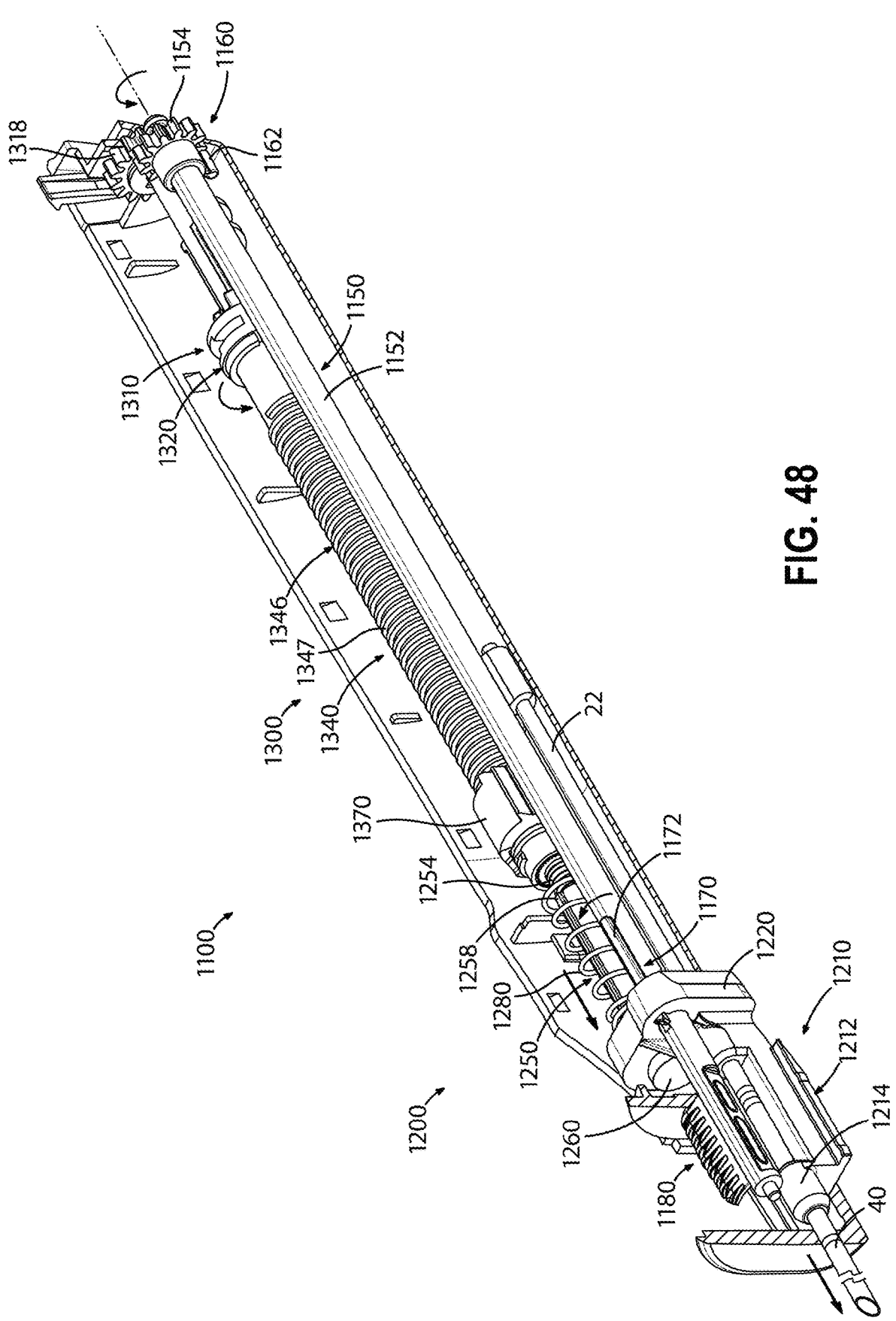
FIG. 48 depicts still another perspective cutaway view of the drive assembly of FIG. 26 in use with the core needle biopsy device of FIG. 1, the drive assembly in a cutter firing configuration.

As shown in FIG. 48, after firing of piercer (22) is complete, firing of cutter (40) may be initiated by reversing the rotation of control shaft (1150) to a counterclockwise direction (relative to the view shown in FIG. 48). Such counterclockwise rotation of control shaft (1150) may result in wings (1172) of release portion (1170) being realigned with channels (1228) of shaft bore (1226) in cutter carriage (1210). Once such realignment occurs, distal movement of cutter carriage (1210) is released so that cutter carriage (1210) may be driven distally by cutter spring (1280) to fire cutter (40).

Figure 49:
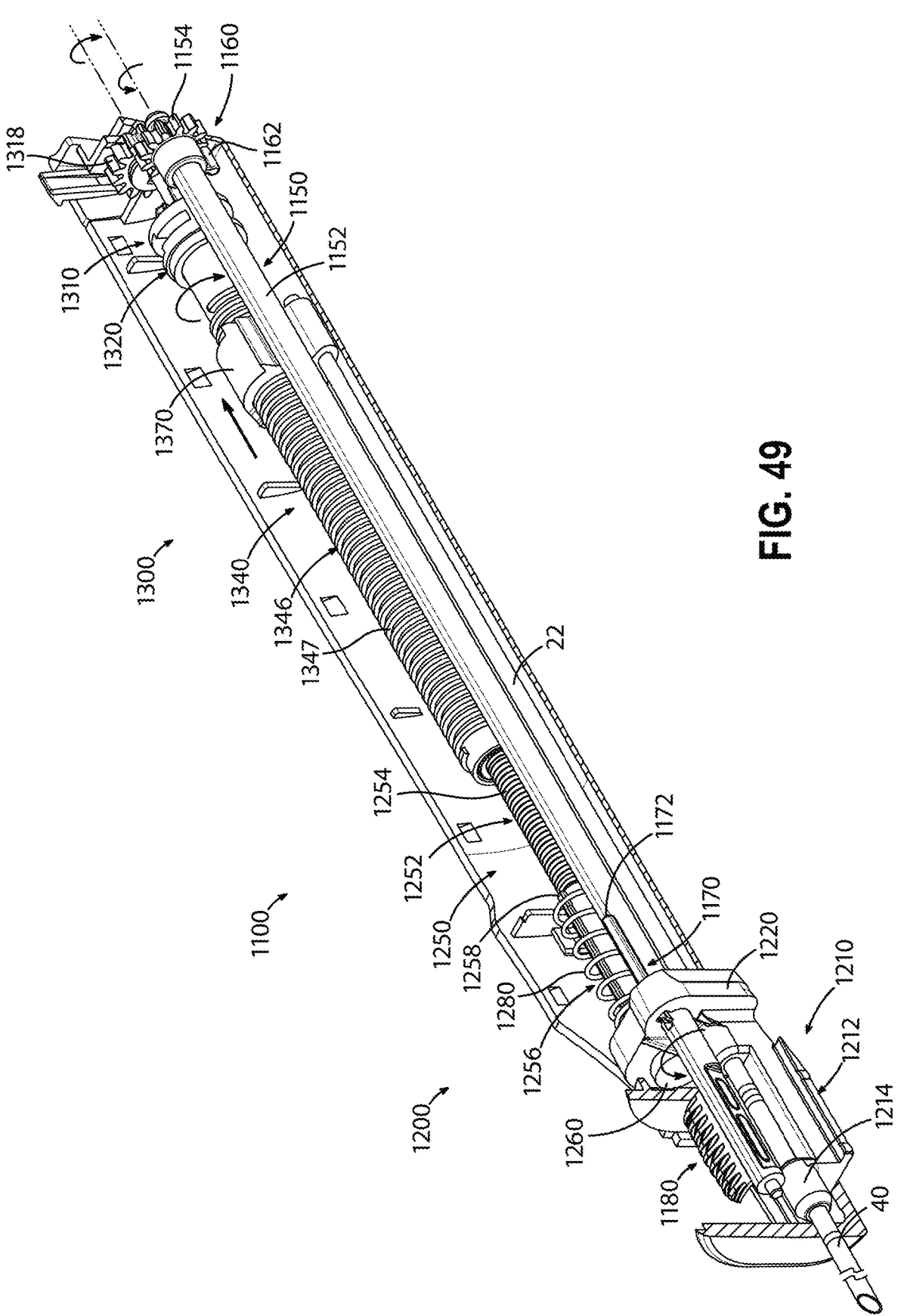
FIG. 49 depicts still another perspective cutaway view of the drive assembly of FIG. 26 in use with the core needle biopsy device of FIG. 1, the drive assembly in a piercer retraction configuration.

After firing of piercer (22) and cutter (40), a tissue collection sequence may be used to both collect a tissue sample from piercer (22) and reset drive assembly (1100) for subsequent tissue collection. Specifically, as best seen in FIG. 49, lead screw drive shaft (1310) may be rotated in the clockwise direction (relative to the view in FIG. 49). Due to the length of lead screw drive shaft (1310), such rotation may also result in clockwise rotation of outer lead screw (1340). Clockwise rotation of outer lead screw (1340) results in proximal translation of piercer carriage (1370) via engagement with threading (1347) of outer lead screw (1340) to retract piercer (22) proximally.

Simultaneously with restriction of piercer (22) via rotation of outer lead screw (1340), outer lead screw (1340) itself is also retracted or translated proximally to further retract piercer (22). In particular, as outer lead screw (1340) rotates, insert (1360) also rotates relative to cutter driver (1250), forcing a portion of cutter driver (1250) out of the hollow interior of outer lead screw (1340). At this stage, cutter driver (1250) is in its distal-most position, so cutter driver (1250) pushes outer lead screw (1340) proximally. This proximal movement of outer lead screw (1340) returns outer lead screw (1340) to the initial home position described above.

Figure 50:
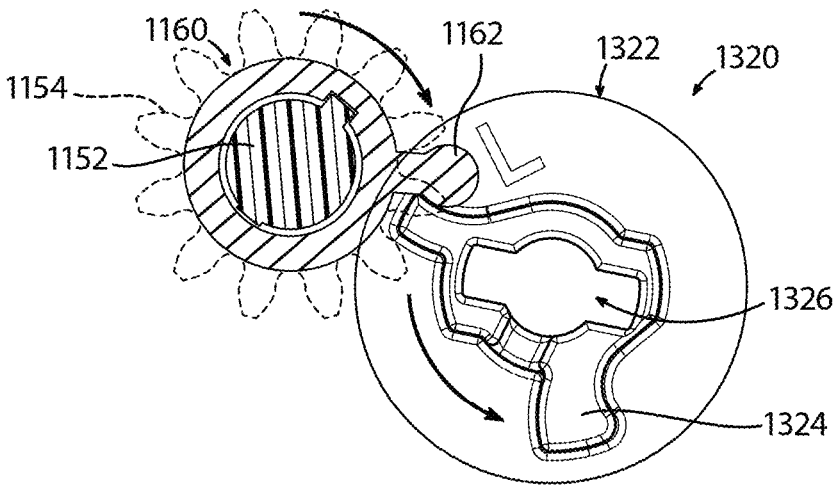
FIG. 50 depicts another rear elevational view of the piercer drive assembly of FIG. 27 with the control shaft of FIG. 40 being rotated to actuate the lead screw latch of FIG. 29.

During the tissue collection sequence, control shaft (1150) may also be rotated in a counterclockwise direction (relative to the view in FIG. 49). As shown in FIG. 50, this rotation of control shaft (1150) may be used to actuate lead screw latch (1320) to recouple lead screw latch (1320) with lead screw drive shaft (1310). In particular, rotation of control shaft (1150) may result in rotation of actuator (1162) of latch portion (1160). Actuator (1162) may then engage actuation protrusion (1324) of lead screw latch (1320) to rotate lead screw latch (1320). Upon rotation of lead screw latch (1320), drive shaft bore (1326) may be moved relative to keyed portion (1314) of lead screw drive shaft (1310) to engage keyed portion (1314) with internal proximal face (1328) of lead screw latch (1320).

Figure 51:
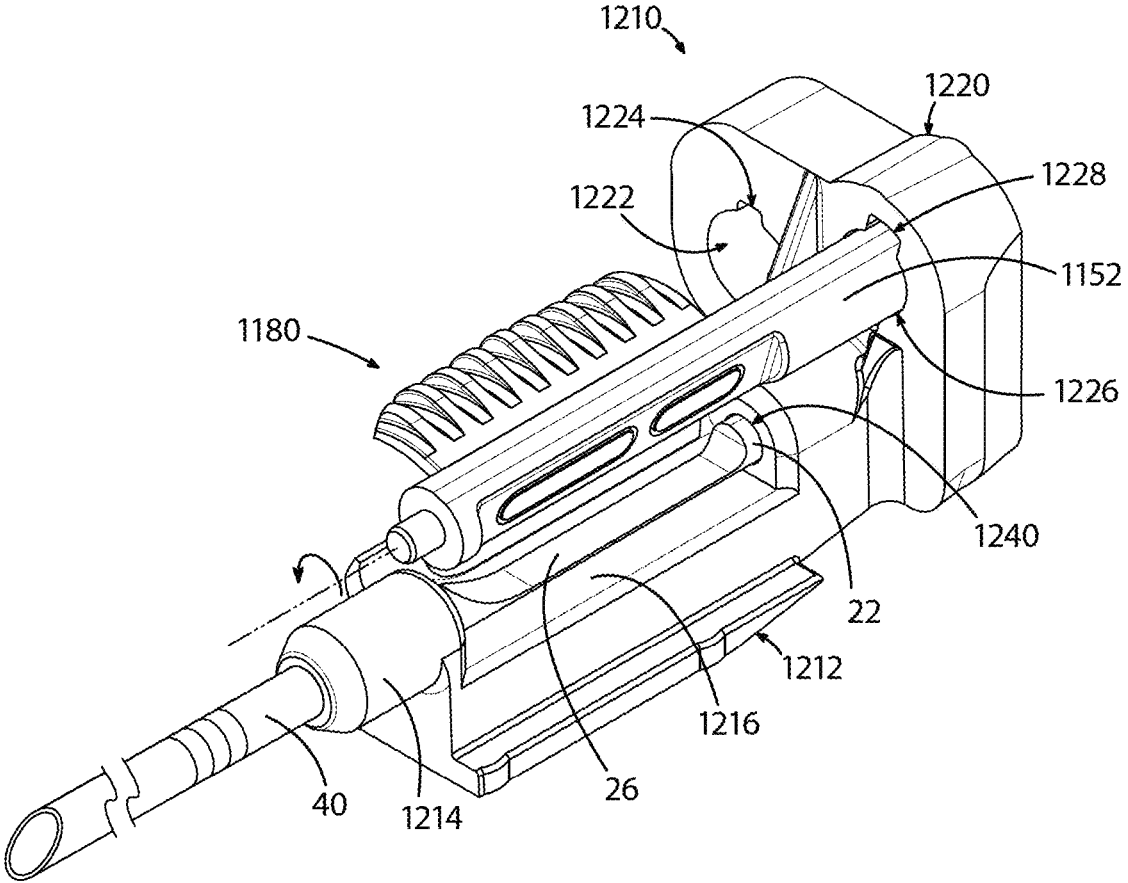
FIG. 51 depicts another detailed perspective view of the cutter drive assembly of FIG. 37 with the control shaft of FIG. 40 being rotated to extract a tissue sample from a notch in the piercer of FIG. 20.

Further counterclockwise rotation of control shaft (1150) may also result in rotation of tissue manipulation portion (1180). AS shown in FIG. 51, rotation of tissue manipulation portion (1180) may result in engagement with tissue manipulator (1216) of cutter carriage (1210) to move a severed tissue sample from notch (26) of piercer (22) and into a tissue chamber.

After the tissue collection sequence is complete, drive assembly (1100) may be returned to the home position described above with respect to initialization. Collection of one or more additional tissue samples may then optionally be performed by repeating the cocking, firing, and tissue collection sequences described above. Such sequences may be repeated as many times as desired to collect any suitable number of tissue samples.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A core needle biopsy device, comprising: a needle assembly including a piercer and a hollow cutter, the piercer including a sharp distal tip and a notch proximal to the distal tip, the piercer being slidably disposed within the cutter to sever a tissue sample into the notch of the piercer; a cutter drive assembly configured to move the cutter; a piercer drive assembly configured to move the piercer, the piercer drive assembly including a lead screw, the lead screw being configured to move both a portion of the cutter drive assembly and a portion of the piercer drive assembly; and an actuation mechanism configured to engage both the cutter drive assembly and the piercer drive assembly to initiate firing of the piercer and the cutter sequentially using the cutter drive assembly and the piercer drive assembly.

Example 2

The core needle biopsy device of Example 1, the piercer drive assembly further including a drive shaft configured to rotate the lead screw, the lead screw being configured to translate relative to the drive shaft to fire the piercer.

Example 3

The core needle biopsy device of Examples 1 or 2, the lead screw including a first threaded portion and a second threaded portion, the first threaded portion including threads having a first pitch, the second threaded portion including threads having a second pitch, the first pitch being different relative to the second pitch.

Example 4

The core needle biopsy device of Example 3, the first threaded portion being configured to engage the cutter drive assembly, the second threaded portion being configured to engage a piercer carriage coupled to the piercer.

Example 5

The core needle biopsy device of any one or more of Examples 1 through 4, the lead screw of the piercer drive assembly including an outer lead screw, the cutter drive assembly including an inner lead screw, the outer lead screw of the piercer drive assembly being configured to threadably receive the inner lead screw of the cutter drive assembly.

Example 6

The core needle biopsy device of Example 5, rotation of the outer lead screw relative to the inner lead screw being configured to simultaneously compress a cutter spring and a piercer spring.

Example 7

The core needle biopsy device of Example 6, the inner lead screw being configured to compress the piercer spring within a hollow interior of the outer leadscrew between a proximal end of the inner lead screw and a portion of the piercer drive assembly disposed within the outer lead screw.

44

Example 8

The core needle biopsy device of any one or more of Examples 5 through 7, the cutter drive assembly including a cutter carriage coupled to the cutter, the inner lead screw being configured to translate the cutter via cutter carriage.

Example 9

The core needle biopsy device of any one or more of Examples 5 through 8, the piercer drive assembly further comprising a latch mechanism, the latch mechanism being configured to selectively release from a portion of the piercer drive assembly to permit translation of the outer lead screw.

Example 10

The core needle biopsy device of Example 9, the latch mechanism being axially secured to the outer lead screw such that the latch mechanism is configured to translate with the outer lead screw.

Example 11

The core needle biopsy device of Examples 9 or 10, the actuation mechanism including an elongate shaft, the elongate shaft defining latch portion and a release portion, the latch portion being configured to actuate the latch mechanism selectively fire the piercer using the outer lead screw, the release portion being configured to engage a portion of the cutter drive assembly to selectively fire the cutter.

Example 12

The core needle biopsy device of Example 11, the actuation mechanism further including a tissue manipulation portion, a portion of the tissue manipulation portion being configured to manipulate tissue into a tissue chamber from the notch of the piercer.

Example 13

The core needle biopsy device of Examples 11 or 12, the latch portion including a protrusion configured to drive rotation of the latch mechanism, the release portion including a pair of wings.

Example 14

The core needle biopsy device of any one or more of Examples 1 through 13, at least a portion of the piercer drive assembly being driven by a motor.

Example 15

The core needle biopsy device of any one or more of Examples 1 through 14, the piercer drive assembly being configured to retract at least a portion of the cutter drive assembly when retracting the piercer.

Example 16

A core needle biopsy device, comprising: a body; a cutter extending from the body, the cutter including an open distal end defined by a sharp edge; a piercer disposed within the cutter, the piercer defining a notch, the piercer being movable relative to the cutter to sever a tissue sample into the notch via the sharp edge; and a drive assembly, including; a cutter drive assembly having a cutter carriage and a cutter driver extending from the cutter carriage; a piercer drive assembly having piercer carriage, a lead screw, and a release mechanism, the release mechanism being configured to release axial translation of the lead screw relative to the body to fire the piercer; and an actuation mechanism, the actuation mechanism being configured to selectively engage the cutter carriage and the release mechanism.

Example 17

The core needle biopsy device of Example 16, the cutter driver being configured for receipt within a portion of the lead screw to communication translation of the lead screw to the cutter drive assembly.

Example 18

The core needle biopsy device of Examples 17 or 18, the piercer drive assembly further including a drive shaft, the drive shaft being configured to rotate the lead screw.

Example 19

The core needle biopsy device of Example 17, the release mechanism being configured to engage the drive shaft to selectively couple the lead screw to the drive shaft.

Example 20

The core needle biopsy device of Examples 18 or 19, the drive shaft including an elongate shaft, the lead screw having a hollow interior configured to receive a portion of the elongate shaft of the drive shaft.

Example 21

The core needle biopsy device of Example 20, the elongate shaft including a keyed portion, the keyed portion being configured to communicate rotary motion from the drive shaft to the lead screw.

Example 22

The core needle biopsy device of Examples 20 or 21, the lead screw being configured to drive compression of a piercer spring between the cutter driver and the drive shaft.

Example 23

A method for collecting a tissue sample using a core needle biopsy device, the method comprising: translating a lead screw distally to fire a piercer distally from a cocked position to a distal position, the piercer being disposed within a hollow cutter, the piercer including a notch that is movable relative to a distal end of the cutter; firing the cutter distally from a cocked position to a distal position after firing the piercer to sever a first tissue sample into the notch of the piercer; rotating the lead screw to retract the piercer while the cutter remains in the distal position to collect the first tissue sample severed into the notch of the piercer; and collecting the first tissue sample from the notch of the piercer.

Example 24

The method of Example 23, the step of translating the lead screw distally including rotating a control shaft a first distance to release the lead screw from a drive shaft.

Example 25

The method of Example 24, the step of firing the cutter distally including rotating the control shaft a second distance to release a cutter carriage from a portion of the control shaft.

Example 26

The method of Example 25, the step of collecting the first tissue sample including rotating the control shaft a third distance to remove the first tissue sample from the notch of the piercer.

Example 27

The method of any one or more of Examples 23 through 26, repeating steps (a)-(d) to collect a second tissue sample.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

We claim:

1. A core needle biopsy device, comprising:
   (a) a needle assembly including a piercer and a hollow cutter, the piercer including a sharp distal tip and a notch proximal to the distal tip, the piercer being slidably disposed within the cutter to thereby collectively be configured to sever a tissue sample into the notch of the piercer;
   (b) a cutter drive assembly configured to move the cutter;
   (c) a piercer drive assembly configured to move the piercer, the piercer drive assembly including a lead screw, the lead screw being configured to move both a portion of the cutter drive assembly and a portion of the piercer drive assembly, the lead screw of the piercer drive assembly including an outer lead screw, the cutter drive assembly including an inner lead screw, the outer lead screw of the piercer drive assembly being configured to threadably receive the inner lead screw of the cutter drive assembly, the piercer drive assembly further comprising a latch mechanism, the latch mechanism being configured to selectively release from a portion of the piercer drive assembly to permit translation of the outer lead screw; and
   (d) an actuation mechanism configured to engage both the cutter drive assembly and the piercer drive assembly to initiate firing of the piercer and the cutter sequentially using the cutter drive assembly and the piercer drive assembly.

2. The core needle biopsy device of claim 1, the piercer drive assembly including a drive shaft configured to rotate the outer lead screw, the outer lead screw being configured to translate relative to the drive shaft to fire the piercer.

3. The core needle biopsy device of claim 1, the outer lead screw including a first threaded portion and a second threaded portion, the first threaded portion including threads having a first pitch, the second threaded portion including threads having a second pitch, the first pitch being different relative to the second pitch.

4. The core needle biopsy device of claim 3, the first threaded portion being configured to engage the cutter drive assembly, the second threaded portion being configured to engage a piercer carriage coupled to the piercer.

5. The core needle biopsy device of claim 1, rotation of the outer lead screw relative to the inner lead screw being configured to simultaneously compress a cutter spring and a piercer spring.

6. The core needle biopsy device of claim 5, the inner lead screw being configured to compress the piercer spring within a hollow interior of the outer lead screw between a proximal end of the inner lead screw and a portion of the piercer drive assembly disposed within the outer lead screw.

7. The core needle biopsy device of claim 1, the cutter drive assembly including a cutter carriage coupled to the cutter, the inner lead screw being configured to translate the cutter via the cutter carriage.

8. The core needle biopsy device of claim 1, the latch mechanism being axially secured to the outer lead screw such that the latch mechanism is configured to translate with the outer lead screw.

9. The core needle biopsy device of claim 1, the actuation mechanism including an elongate shaft, the elongate shaft defining a latch portion and a release portion, the latch portion being configured to actuate the latch mechanism to selectively fire the piercer using the outer lead screw, the release portion being configured to engage a portion of the cutter drive assembly to selectively fire the cutter.

10. The core needle biopsy device of claim 9, the actuation mechanism further including a tissue manipulation portion, a portion of the tissue manipulation portion being configured to manipulate tissue into a tissue chamber from the notch of the piercer.

11. The core needle biopsy device of claim 9, the latch portion including a protrusion configured to drive rotation of the latch mechanism, the release portion including a pair of wings.

12. The core needle biopsy device of claim 1, at least a portion of the piercer drive assembly being driven by a motor.

13. The core needle biopsy device of claim 1, the piercer drive assembly being configured to retract at least a portion of the cutter drive assembly when retracting the piercer.

14. The core needle biopsy device of claim 1, the outer lead screw being further configured to move the distal tip distal to the hollow cutter.

15. A core needle biopsy device, comprising:
   (a) a needle assembly including a piercer and a hollow cutter, the piercer including a sharp distal tip and a notch proximal to the distal tip, the piercer being slidably disposed within the cutter to thereby collectively be configured to sever a tissue sample into the notch of the piercer;
   (b) a cutter drive assembly configured to move the cutter;
   (b)
   (c) a piercer drive assembly configured to move the piercer, the piercer drive assembly including a lead screw having a longitudinal axis laterally offset from the piercer, the lead screw including a first external thread configured to move a portion of the cutter drive assembly, the lead screw including a second external thread configured to move a portion of the piercer drive assembly, the first and second external threads being separate and discrete from one another; and
   (d) an actuation assembly configured to engage both the cutter drive assembly and the piercer drive assembly to initiate firing of the piercer and the cutter sequentially using the cutter drive assembly and the piercer drive assembly.

16. The core needle biopsy device of claim 15, the piercer drive assembly further including a drive shaft configured to rotate the lead screw, the lead screw being configured to translate relative to the drive shaft to fire the piercer.

17. The core needle biopsy device of claim 15, the first external thread threaded portion including threads having a first pitch, the second external thread having a second pitch, the first pitch being different relative to the second pitch.

18. The core needle biopsy device of claim 17, the first external thread being configured to engage the cutter drive assembly, the second external thread being configured to engage a piercer carriage coupled to the piercer.

* * * * *